United States Patent

Kato et al.

[11] Patent Number: 5,633,248
[45] Date of Patent: May 27, 1997

[54] AMINE COMPOUNDS, THEIR PRODUCTION AND USE

[75] Inventors: Kaneyoshi Kato, Hyogo; Yoshihiro Sugiura, Nara; Koichi Kato, Ibaraki, all of Japan

[73] Assignee: Takeda Chemical Industries, Ltd., Osaka, Japan

[21] Appl. No.: 561,282

[22] Filed: Nov. 21, 1995

[30] Foreign Application Priority Data

Nov. 21, 1994 [JP] Japan ................................. 6-286245

[51] Int. Cl.$^6$ .................. C07D 221/00; C07D 211/00; C07D 295/00; C07D 241/00; A61K 31/44; A61K 31/47; A61K 31/40; A61K 31/41

[52] U.S. Cl. .................. 514/212; 514/278; 514/252; 514/253; 514/255; 514/227.5; 514/228.8; 514/231.2; 514/231.5; 514/231.8; 514/234.5; 514/234.8; 514/307; 514/311; 514/314; 514/316; 514/317; 514/331; 514/213; 514/218; 514/357; 514/290; 514/430; 514/465; 514/466; 546/16; 546/17; 546/18; 546/148; 544/396; 544/360; 544/361; 544/362; 544/363; 544/364; 544/365; 544/366; 544/367; 544/379; 544/112; 544/113; 544/114; 544/115; 544/116; 544/118; 544/119; 544/121; 544/123; 544/126; 544/127; 544/129; 544/130; 544/135; 544/136; 544/144

[58] Field of Search .................. 514/212, 213, 514/218, 278, 252, 253, 255, 227.5, 316, 228.8, 317, 231.2, 331, 231.5, 231.8, 357, 234.5, 290, 234.8, 430, 307, 311, 314, 445, 466; 546/16, 17, 18, 148, 149, 186, 192, 207, 208, 209, 210, 211, 212, 213, 219, 329, 111; 549/74, 80, 434; 540/609; 544/106, 11, 101, 70, 396, 360-367, 379, 112-144

[56] References Cited

U.S. PATENT DOCUMENTS 4,650,900 3/1987 Lassen et al. ................. 564/56

FOREIGN PATENT DOCUMENTS 0026989 4/1981 European Pat. Off. .
0187700 7/1986 European Pat. Off. .
1335831 12/1963 France .

OTHER PUBLICATIONS

Journal of Medicinal Chemistry, vol. 34, No. 1 (1991) pp. 12–19.
Arch. Int. Pharmacodyn., vol. CVII, No. 2 (1956) pp. 194–201.

Primary Examiner—Matthew V. Grumbling
Attorney, Agent, or Firm—Fitzpatrick, Cella, Harper & Scinto

[57] ABSTRACT

A compound of the formula:

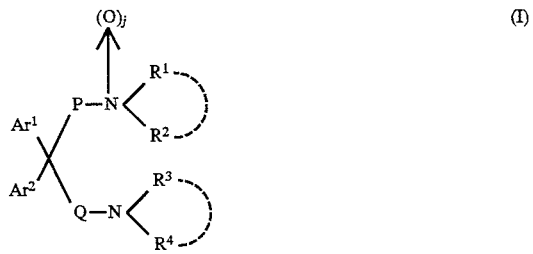

wherein $Ar^1$ and $Ar^2$ independently represent an optionally substituted aromatic group; P and Q independently represent a divalent aliphatic hydrocarbon group having at least 2 carbon atoms and optionally having either oxygen or sulfur in the carbon chain; $R^1$ and $R^3$ independently represent —CO—R, —CONH—R (R represents a hydrocarbon group or a heterocyclic group) or a hydrocarbon group; $R^2$ and $R^4$ independently represent hydrogen or an alkyl group; $R^2$ and $R^4$ independently represent hydrogen or an alkyl group; $R^1$ and $R^2$ or $R^3$ and $R^4$, taken together with the adjacent nitrogen atom, may form a nitrogen-containing heterocyclic group; and j represents 0 or 1, or a salt thereof, has excellent GnRH-receptor antagonizing activity and is useful as a prophylactic and therapeutic agent for hormone-dependent and other diseases.

18 Claims, No Drawings

AMINE COMPOUNDS, THEIR PRODUCTION AND USE

BACKGROUND OF THE INVENTION

1. Field of the Invention

This invention relates to a novel amine compound or a salt thereof having excellent gonadotropin releasing hormone (GnRH) receptor antagonizing activity, a process for producing it, and a pharmaceutical composition containing it.

GnRH, which is a decapeptide consisting of 10 amino acids, is produced in the hypothalamus. It is known that GnRH regulates secretion of various hormones such as luteinizing hormone and follicle stimulating hormone through receptors which may be present in the anterior pituitary to thereby play a multi-pronged physiological role including induction of ovulation. Therefore, an antagonist or an agonist that is specific and selective for these receptors would modulate secretion of the anterior pituitary hormones. Therefore, such an antagonist or agonist can be expected to be useful for the prevention and treatment of anterior pituitary hormone-dependent diseases.

Since 1971 when GnRH was first discovered, a large number of its analogs have been synthesized in hopes of exploiting their agonistic or antagonistic activity. For example, leuprolerin acetate is a compound known to have a higher affinity for GnRH receptors than native GnRH and is less liable to be metabolized than the latter.

It is known that, when administered repeatedly, leuprolerin acetate, which is 20 to 50-fold as active as native GnRH, causes a receptor down-regulation to suppress the release and production of gonadotropin in the pituitary gland and in the testis, for it decreases the response to gonadotropin so that its testosterone producing capacity is diminished to the castrated level. It is known that, as a consequence, the drug displays antitumoral effects in hormone-dependent neoplastic diseases such as cancer of the prostate. In fact, leuprolerin acetate is clinically in broad use as a therapeutic drug for prostatic cancer and endometriosis, among other diseases.

However, these GnRH agonists are peptides which are poorly absorbed after oral administration and, hence, restricted in compatible dosage form. Moreover, there are cases in which they transiently manifest agonistic activity after the beginning of use and before the expected efficacy begins to appear, thus causing elevation of serum steroid hormone levels and transitory exacerbation of ostealgia.

Against this background, a great deal of research synthesis of GnRH antagonists which would show therapeutic efficacy and yet be free from the above-mentioned adverse effects has been eagerly undertaken.

2. Related Background Art

Today, as compounds having GnRH receptor antagonizing activity, a large number of cyclic hexapeptide derivatives (JP-A-61-191698) and bicyclic peptide derivatives [J. Med. Chem., 36, 3265–3273, 1993], all conceived from the steric structure of GnRH, have been designed and are known. However, since they all are peptides, these compounds still have the drawbacks of poor absorption after oral administration and poor in vivo stability.

Meanwhile, synthesis of non-peptide compounds having GnRH receptor antagonizing activity has also been attempted. By way of illustration, a benzazepine compound of the formula:

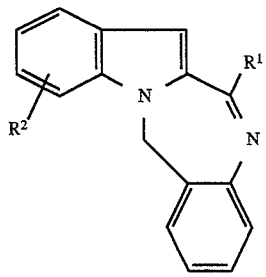

[wherein $R^1$ represents the amino function of an amine of the formula $-NR^3R^4$, 4-morpholino,

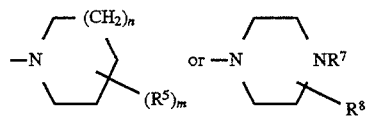

$R^2$ represents hydrogen, alkoxy, alkyl, trifluoromethyl, halogen, nitro, hydroxyl, or dialkylamino; $R^3$ and $R^4$ independently represent hydrogen, alkyl, or alkyl substituted by hydroxyl, halogen or alkoxy; m is equal to 0 or 1; n is equal to 0, 1 or 2; $R^5$ represents hydroxyl, alkyl, halogen, carboxyl, alkoxycarbonyl, or alkyl substituted by hydroxyl, halogen, alkoxy or phenyl; $R^6$ represents hydrogen, alkyl, carboxyl, alkoxycarbonyl, or phenyl; and $R^7$ represents hydrogen, alkyl, alkoxycarbonyl, or alkyl substituted by hydroxyl, halogen, alkoxy, phenoxy or alkoxycarbonyl] is reported in JP-A-62-116514. A compound of the formula:

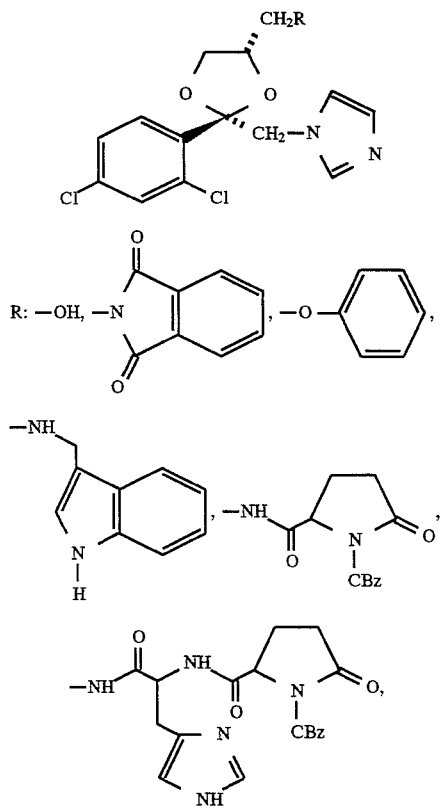

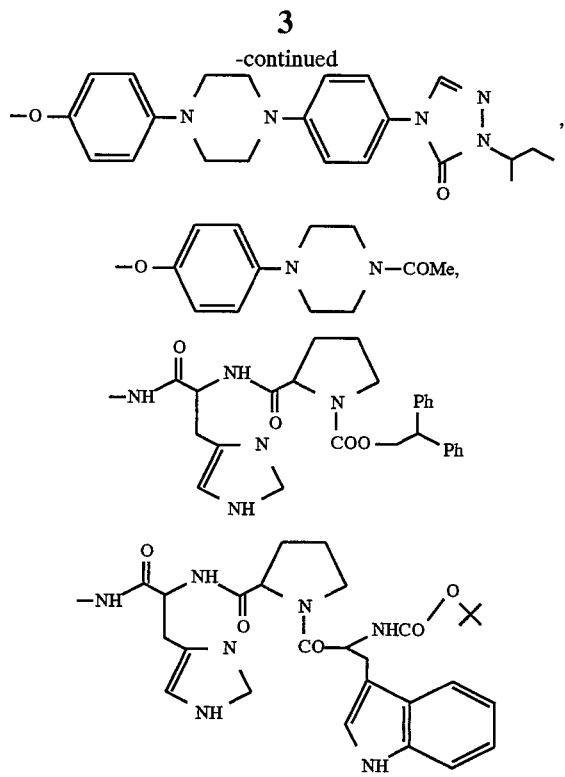

which has LHRH (luteinizing hormone-releasing hormone) antagonizing activity is reported in Journal of Medicinal Chemistry, 32, 2036–2038, 1989.

Meanwhile, it is described in JP-A-4-253970 corresponding to U.S. Pat. No. 5,393,959 that a compound of the formula:

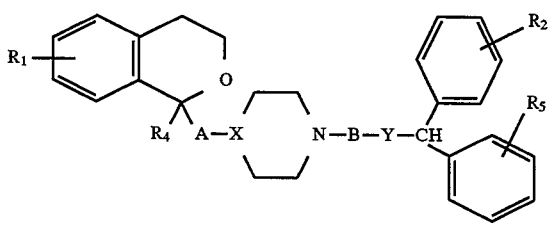

[wherein $R_1$, $R_2$ and $R_3$ each represents hydrogen, hydroxyl, $C_{1-4}$ alkyl, $C_{1-4}$ alkoxy, halogen, $CF_3$, or methylenedioxy; $R_4$ represents hydrogen or $C_{1-4}$ alkyl; A represents a bond or $C_{1-6}$ alkylene or alkylidene; B is $C_{1-6}$ alkylene or alkylidene when Y is a bond, or B is $C_{2-6}$ alkylene when Y is O, S or $NR^5$; X represents CH or N; $R_5$ represents hydrogen or $C_{1-4}$ alkyl] has intracellular calcium antagonizing activity and can be used as a therapeutic drug for angina pectoris and myocardial infarction.

Furthermore, Journal of Medicinal Chemistry, 34, 12–19 (1991) mentions that a compound of the formula:

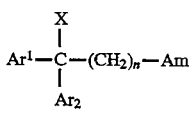

[wherein $Ar^1$ and $Ar^2$ each represents H, phenyl, or 2-, 3- or 4-pyridyl; Am represents 2,6-dimethyl-1-piperidinyl, 1-piperidinyl, or 2,5-dimethyl-1-pyrrolidinyl; n is equal to 1–4; X represents OH, H, cyano, aminomethyl, acetolaminomethyl or carbamoyl] has antiarrhythmic activity.

Archives of International Pharmacodynamics, 107, 194–201, 1956 describes that a compound of the formula:

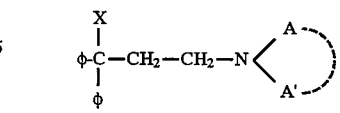

[wherein R represents —$CONH_2$, —$NH_2$, —$NHCOCH_3$, —$NHCOC_6H_5$, —$CH_2NH_2$, —$CH_2NHCOCH_3$, —$CH_2NHCOC_6H_5$ or —CN; NAA' represents $N(CH_3)_2$, $N(C_2H_5)_2$, $N(i—C_3H_7)_2$, $NC_4H_8$, $NC_5H_{10}$ or $NC_4H_8O$] has parasympathomimetic activity.

JP-A-62-123164 mentions that a compound of the formula:

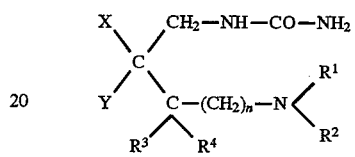

[wherein X and Y, which may be the same or different, are selected from the class consisting of phenyl groups which may respectively be substituted by 1 or 2 substituents selected from among halogen, $CF_3$, OH and $C_{1-4}$ alkoxy; $R^1$ and $R^2$ are the same or different and each is selected from the class consisting of lower alkyl groups of 1–4 carbon atoms, or $R^1$ and $R^2$, taken together with the nitrogen atom, form a saturated 5- or 6-membered ring; $R^3$ and $R^4$ are selected from among hydrogen, lower alkyl or alkenyl of 1–6 carbon atoms, cyclopentyl and cyclohexyl; n is equal to 0 or 1] has antitumoral activity.

However, a non-peptide compound having sufficiently high GnRH receptor antagonizing activity for use as a medicine has not been discovered. Therefore, an aromatic amine derivative structurally different from the abovementioned known compounds and having GnRH receptor antagonizing activity with a high clinical potential and safety has been awaited in earnest.

SUMMARY OF THE INVENTION

An object of the present invention is to provide a compound of the formula:

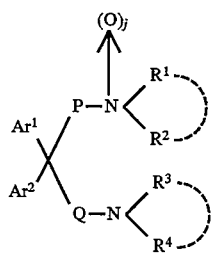

wherein $Ar^1$ and $Ar^2$ independently represent an optionally substituted aromatic group;

P and Q independently represent a divalent aliphatic hydrocarbon group having at least 2 carbon atoms, which may have either oxygen or sulfur within the carbon chain;

$R^1$ and $R^3$ independently represent i) an acyl group of —CO—R or —CONH—R wherein R represents an optionally substituted hydrocarbon group or an optionally substituted heterocyclic group, or ii) an optionally substituted hydrocarbon group;

$R^2$ and $R^4$ independently represent hydrogen or an optionally substituted alkyl group;

$R^1$ and $R^2$ or $R^3$ and $R^4$, taken together with the adjacent nitrogen atom, may form an optionally substituted nitrogen-containing heterocyclic group; and j represents 0 or 1, or a salt thereof.

A further object of the invention is to provide a gonadotropin-releasing hormone receptor antagonistic composition which comprises a compound of the formula:

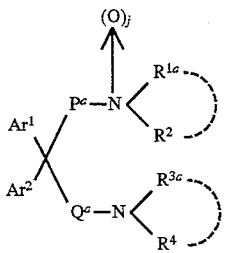

wherein $Ar^1$ and $Ar^2$ independently represent an optionally substituted aromatic group;

$P^a$ and $Q^a$ independently represent a divalent aliphatic hydrocarbon group which may have either oxygen or sulfur within the carbon chain;

$R^{1a}$ and $R^{3a}$ independently represent an acyl group or an optionally substituted hydrocarbon group;

$R^2$ and $R^4$ independently represent hydrogen or an optionally substituted alkyl group;

$R^{1a}$ and $R^2$ or $R^{3a}$ and $R^4$, taken together with the adjacent nitrogen atom, may form an optionally substituted nitrogen-containing heterocyclic group; and j represents 0 or 1, or a salt thereof, and a pharmaceutically acceptable carrier.

A further object of the invention is to provide a method for treating diseases related to gonadotropin-releasing hormone in mammals which comprises the steps of selecting a compound of the formula:

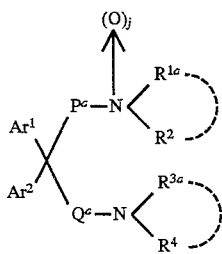

wherein $Ar^1$ and $Ar^2$ independently represent an optionally substituted aromatic group;

$P^a$ and $Q^a$ independently represent a divalent aliphatic hydrocarbon group which may have either oxygen or sulfur within the carbon chain;

$R^{1a}$ and $R^{3a}$ independently represent an acyl group or an optionally substituted hydrocarbon group;

$R^2$ and $R^4$ independently represent hydrogen or an optionally substituted alkyl group;

$R^{1a}$ and $R^2$ or $R^{3a}$ and $R^4$, taken together with the adjacent nitrogen atom, may form an optionally substituted nitrogen-containing heterocyclic group; and j represents 0 or 1, or a salt thereof, and administering to a subject a therapeutically effective amount of said compound.

A further object of the invention is to provide a method of manufacturing a pharmaceutical composition for treating diseases related to gonadotropin-releasing hormone, comprising the steps of selecting a compound of the formula:

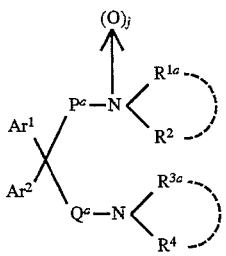

wherein $Ar^1$ and $Ar^2$ independently represent an optionally substituted aromatic group;

$P^a$ and $Q^a$ independently represent a divalent aliphatic hydrocarbon group which may have either oxygen or sulfur within the carbon chain;

$R^{1a}$ and $R^{3a}$ independently represent an acyl group or an optionally substituted hydrocarbon group;

$R^2$ and $R^4$ independently represent hydrogen or an optionally substituted alkyl group;

$R^{1a}$ and $R^2$ or $R^{3a}$ and $R^4$, taken together with the adjacent nitrogen atom, may form an optionally substituted nitrogen-containing heterocyclic group; and j represents 0 or 1, or a salt thereof, and admixing said compound with a pharmaceutically acceptable carrier.

The inventors discovered a non-peptide compound activity, Compound (I) or Compound (I'), of the formula:

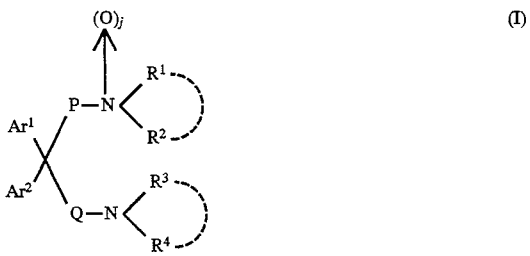

wherein $Ar^1$ and $Ar^2$ independently represent an optionally substituted aromatic group;

P and Q independently represent a divalent aliphatic hydrocarbon group having at least 2 carbon atoms, which may have either oxygen or sulfur within the carbon chain;

$R^1$ and $R^3$ independently represent i) an acyl group of —CO—R or —CONH—R wherein R represents an optionally substituted hydrocarbon group or an optionally substituted heterocyclic group, or ii) an optionally substituted hydrocarbon group;

$R^2$ and $R^4$ independently represent hydrogen or an optionally substituted alkyl group;

$R^1$ and $R^2$ or $R^3$ and $R^4$, taken together with the adjacent nitrogen atom, may form an optionally substituted nitrogen-containing heterocyclic group; and j represents 0 or 1, [Compound (I)] or a salt thereof, and the compound of the formula:

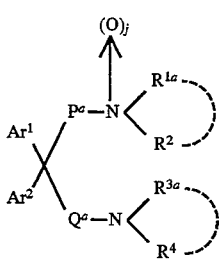

(I')

wherein $P^a$ and $Q^a$ independently represent a divalent aliphatic hydrocarbon group which may have either oxygen or sulfur within the carbon chain;

$R^{1a}$ and $R^{3a}$ independently represent an acyl group or an optionally substituted hydrocarbon group;

$R^{1a}$ and $R^2$ or $R^{3a}$ and $R^4$, taken together with the adjacent nitrogen atom, may form an optionally substituted nitrogen-containing heterocyclic group; and the other symbols are defined as above, [Compound (I')]. The compounds of the invention or a salt thereof, exhibit excellent GnRH receptor antagonizing activity and low toxicity without being materially influenced by the presence or absence or kinds of substituents on the rings, thus being of great clinical use.

DETAILED DESCRIPTION OF THE INVENTION

This invention is, therefore, directed to:
(1) a compound (I) or a salt thereof,
(2) a process for producing compound (1), which comprises reacting a compound of the formula:

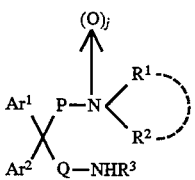

wherein all symbols have the same meanings as defined above, or a salt thereof, with a compound of the formula:

$R^4$—L wherein L represents a leaving group and $R^4$ is as defined above or a salt thereof, and (3) a gonadotropin-releasing hormone receptor antagonistic composition which comprises a compound (I') or a salt thereof.

In a compound (1), preferably, $Ar^1$ and $Ar^2$ are independently $C_{6-14}$ aryl group which may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl, $C_{6-10}$ aryl and $C_{6-10}$ aryloxy, P and Q are independently divalent $C_{2-6}$ aliphatic hydrocarbon group which may have either oxygen or sulfur within the carbon chain, $R^1$ and $R^3$ are independently i) an acyl group of —CO—$R^a$ or —CONH—$R^a$ wherein $R^a$ is a) a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group which may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl, and 5- or 6-membered heterocyclic group, or b) a 5- to 10-membered heterocyclic group containing, besides carbon atom, 1 to 4 hetero atoms selected from nitrogen atom, oxygen atom and sulfur atom, which may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl, $C_{6-10}$ aryl and $C_{6-10}$ aryloxy, or ii) a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group which may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl and 5- or 6-membered heterocyclic group, and $R^2$ and $R^4$ are independently hydrogen or a $C_{1-6}$ alkyl group which may be substituted by 1 to 5 substituents selected from the group consisting of halogen, nitro, cyano, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl, $C_{6-10}$ aryl and $C_{6-10}$ aryloxy, or $R^1$ and $R^2$ or $R^3$ and $R^4$, taken together with the adjacent nitrogen atom, form a nitrogen-containing heterocyclic group of the formula:

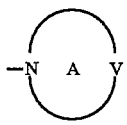

i)

wherein ring A is a 4- to 8-membered ring which may be substituted by hydroxyl or oxo group; and V is >O, >C=O,

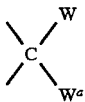

or >N—W in which W is a) hydrogen, b) a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group which may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl and 5- or 6-membered heterocyclic group, or c) a 5- to 10-membered heterocyclic group containing, besides carbon atom, 1 to 4 hetero atoms selected from nitrogen atom, oxygen atom and sulfur atom, which may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl, $C_{6-10}$ aryl and $C_{6-10}$ aryloxy, and $W^a$ is hydrogen or hydroxyl,

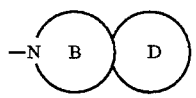

ii)

wherein ring B is a 4- to 12-membered mono- or bicyclic ring optionally having an oxo group and optionally substituted by 1 to 5 $C_{1-6}$ alkyl groups; and ring D is a 4- to 12-membered aromatic ring which may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl, $C_{6-10}$ aryl and $C_{6-10}$ aryloxy, or

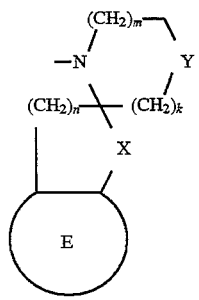

wherein ring E is a 5- to 10-membered aromatic ring which may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl, $C_{6-10}$ aryl and $C_{6-10}$ aryloxy;

X is —$CH_2$—, —CO— or —CH(OH)—;

Y is —$CH_2$—, —O— or —$NW^b$— in which $W^b$ is hydrogen or a $C_{1-6}$ alkyl group which may be substituted by 1 to 5 substituents selected from the group consisting of halogen, $C_{1-3}$ alkylenedioxy, nitro, cyano, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl, $C_{6-10}$ aryl, $C_{6-10}$ aryloxy and 5- or 6-membered heterocyclic group;

k+m is an integer of 1 to 4; and n is an integer of 1 to 3.

In a compound (I), $R^1$ is preferably a $C_{7-16}$ aralkyl, $C_{3-6}$ cycloalkyl or benzo-$C_{3-6}$ cycloalkyl group which may be substituted by 1 to 5 substituents selected from the group consisting of halogen, optionally halogenated $C_{1-6}$ alkyl, optionally halogenated $C_{1-6}$ alkoxy and $C_{1-6}$ alkoxy-carbonyl.

In a compound (I), $R^3$ is preferably an acyl group of —CO—$R^b$ wherein $R^b$ is a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group which may be substituted by 1 to 5 substituents selected from the group consisting of halogen, $C_{1-3}$ alkylenedioxy, nitro, cyano, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl and 5- or 6-membered heterocyclic group.

In a compound (I),

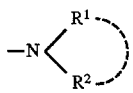

is preferably the formula:

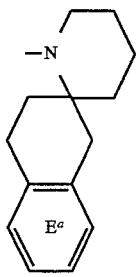

wherein ring $E^a$ is a benzene ring which may be substituted by 1 to 4 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl, $C_{6-10}$ aryl and $C_{6-10}$ aryloxy.

In a compound (1), P and Q are preferably independently a $C_{2-6}$ alkylene or $C_{2-6}$ alkenylene group.

In a compound (1), P and Q are preferably independently a $C_{3-5}$ alkylene group.

In a compound (1), $R^4$ is preferably hydrogen.

In a compound (1), j is preferably O.

In a compound (1), preferable is the compound of the formula:

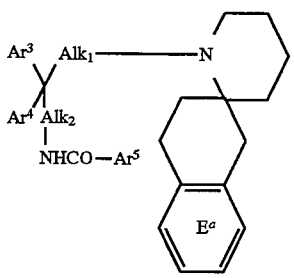

wherein $Ar^3$ and $Ar^4$ are independently an optionally halogenated phenyl group; $Alk_1$ and $Alk_2$ are independently a $C_{2-6}$ alkylene group; $Ar^5$ is a $C_{7-16}$ aralkyl group which may be substituted by halogen or optionally halogenated $C_{1-3}$ alkoxy; and ring $E^a$ is a benzene ring which may be substituted by 1 to 3 substituents selected from the group consisting of optionally halogenated $C_{1-3}$ alkoxy, $C_{1-3}$ alkyl-carbonyl and amino.

In a compound (1), more preferable is (+)-3,4-Dihydro-6-methoxy-1'-{4,4-diphenyl-7-{[(4-methoxyphenyl)acetyl]amino}heptyl}spiro[naphthalene-2(1H),2'-piperidine], (−)-3,4-Dihydro-6-methoxy-1'-{4,4-diphenyl-7-{[(4-methoxyphenyl)acetyl]amino}heptyl}spiro[naphthalene-2(1H),2'-piperidine], (−)-3,4-Dihydro-6,7-dimethoxy-1'-{4,4-diphenyl-7-{[(4-methoxyphenyl)acetyl]amino}heptyl}spiro [naphthalene-2(1H),2'-piperidine]-1-one, (−)-3,4-Dihydro-6,7-dimethoxy-1'-{4,4-diphenyl-7-{[(4-fluorophenyl)acetyl]amino}heptyl}spiro [naphthalene-2(1H),2'-piperidine], (+)-3,4-Dihydro-6,7-dimethoxy-1'-{4,4-diphenyl-7-{[(4-fluorophenyl)acetyl]amino}heptyl}spiro [naphthalene-2(1H),2'-piperidine], (−)-3,4-Dihydro-6,7-dimethoxy-1'-{4,4-diphenyl-7-{[3-(4-fluorophenyl)propionyl]amino}heptyl}spiro [naphthalene-2(1H),2'-piperidine], (+)-3,4-Dihydro-6,7-dimethoxy-1'-{4,4-diphenyl-7-{[3-(4-fluorophenyl)propionyl]amino}heptyl}spiro [naphthalene-2(1H),2'-piperidine], (+)-3,4-Dihydro-6,7-dimethoxy-1'-{7-{[3-(4-chlorophenyl)propionyl]amino}-4,4-diphenylheptyl}spiro [naphthalene-2(1H),2'-piperidine], (−)-3,4-Dihydro-6,7-dimethoxy-1'-{7-{[3-(4-chlorophenyl)propionyl]amino}-4,4-diphenylheptyl}spiro [naphthalene-2(1H),2'-piperidine], (−)-3,4-Dihydro-6,7-dimethoxy-1'-{4,4-diphenyl-7-{[3-(4-methoxyphenyl)propionyl]amino}heptyl}spiro [naphthalene-2(1H),2'-piperidine], (+)-3,4-Dihydro-6,7-dimethoxy-1'-{4,4-diphenyl-7-{[3-(4-methoxyphenyl)propionyl]amino}heptyl}spiro [naphthalene-2(1H),2'-piperidine], 3,4-Dihydro-4'-{4,4-diphenyl-7-{[3-(4-methoxyphenyl)propionyl]amino}heptyl}spiro[naphthalene-2(1H),3'-morpholine], 3,4-Dihydro-7-methoxy-4'-{4,4-diphenyl-7-{[3-(4-methoxyphenyl)propionyl]amino}heptyl}spiro [naphthalene-2(1H),3'-morpholine], 3,4-Dihydro-6,7-dimethoxy-4'-{4,4-diphenyl-7-{[3-(4-methoxyphenyl)propionyl]amino}heptyl}spiro [naphthalene-2(1H),3'-morpholine], or a salt thereof.

In a composition (3), preferred is composition for treating a sex hormone-dependent disease.

In a composition (3), more preferred is a composition for treating tumor, prostatic hypertrophy, endometriosis, precocious puberty or premenstrual syndrome.

The aromatic group of the "optionally substituted aromatic group" for $Ar^1$ and $Ar^2$ includes, for example, aromatic hydrocarbon groups and heteroaromatic groups. Preferred is an aromatic hydrocarbon group.

The "aromatic hydrocarbon group" mentioned above includes, for example, monocyclic or fused polycyclic aromatic hydrocarbon groups of 6 to 14 carbon atoms. Thus, $C_{6-14}$ aryl groups such as phenyl, 1-naphthyl, 2-naphthyl, indenyl, anthryl, etc. can be mentioned, among other groups. Particularly preferred is phenyl in many instances.

The "heteroaromatic group" mentioned above includes, for example, 5- to 14-membered monocyclic, bicyclic or tricyclic heteroaromatic groups containing 1 or 2 kinds of and preferably 1 to 3 hetero atoms selected from among nitrogen, oxygen and sulfur in addition to carbon as ring members. Thus, 5- to 10-membered (monocyclic or bicyclic) heteroaromatic groups containing 1-3 hetero atoms selected from among nitrogen, oxygen and sulfur in addition to carbon as ring members, such as 2-thienyl, 3-thienyl, 2-pyridyl, 4-pyridyl, 2-furyl, 3-furyl, 4-quinolyl, 8-quinolyl, 4-isoquinolyl, pyrazinyl, 2-pyrimidinyl, 3-pyrrolyl, 2-imidazolyl, 3-pyridazinyl, 3-isothiazolyl, 3-isoxazolyl, 1-indolyl, 2-isoindolyl, etc. can be mentioned.

Particularly preferred in many instances are 5- or 6-membered heteroaromatic groups containing 1-3 hetero atoms selected from among nitrogen, oxygen and sulfur in addition to carbon as ring members (e.g. 2-pyridyl, 4-pyridyl, etc.).

The substituent that may be present on the "optionally substituted aromatic group" for $Ar^1$ and $Ar^2$ includes, for example, halogen (e.g. fluorine, chlorine, bromine, iodine), $C_{1-3}$ alkylenedioxy (e.g. methylenedioxy, ethylenedioxy, etc), nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino (e.g. methylamino, ethylamino, etc.), di-$C_{1-6}$ alkylamino (e.g. dimethylamino, diethylamino, etc.), $C_{1-6}$ alkyl-carbonylamino (e.g. methylcarbonylamino, ethylcarbonylamino, etc.), $C_{1-6}$ alkyl-carbonyl (e.g. acetyl, ethylcarbonyl, etc.), carboxyl, $C_{1-6}$ alkoxy-carbonyl (e.g. methoxycarbonyl, ethoxycarbonyl, propoxycarbonyl, butoxycarbonyl, etc.), carbamoyl, mono-$C_{1-6}$ alkylcarbamoyl (e.g. methylcarbamoyl, ethylcarbamoyl, etc.), di-$C_{1-6}$ alkylcarbamoyl (e.g. dimethylcarbamoyl, diethylcarbamoyl, etc.), sulfo, $C_{1-6}$ alkylsulfonyl (e.g methylsulfonyl, ethylsulfonyl, etc.), $C_{1-6}$ alkylsulfinyl (e.g. methylsulfinyl, ethylsulfinyl, etc.), $C_{6-10}$ aryl (e.g. phenyl, etc.) and $C_{6-10}$ aryloxy (e.g. phenyloxy, etc.)

The aromatic group of the "optionally substituted aromatic group" may have 1 to 5, preferably 1 to 3, suitable substituent groups selected from among those mentioned above in substitutable positions of the ring structure, and where the number of such substituents is 2 or more, the substituent groups may be the same or different.

The "optionally halogenated $C_{1-6}$ alkyl" as the term is used in this specification includes, for example, $C_{1-6}$ alkyl groups optionally having 1-3 halogen atoms (e.g. F, Cl, Br, I) (e.g. methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc.).

The "optionally halogenated $C_{3-6}$ cycloalkyl" as the term is used in this specification includes, for example, $C_{3-6}$ cycloalkyl groups optionally having 1–3 halogen atoms (e.g. F, Cl, Br, I) (e.g. cyclopropyl, cyclobutyl, cyclopentyl, cyclohexyl, 2,2,3,3-tetrafluorocyclopentyl, 4-chlorocyclohexyl, etc.).

The "optionally halogenated $C_{1-6}$ alkoxy" as the term is used in this specification includes, for exmaple, $C_{1-6}$ alkoxy groups optionally having 1–3 halogen atoms (e.g. F, Cl, Br, I) (e.g. methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, etc.).

The "optionally halogenated $C_{1-6}$ alkylthio" as the term is used in this specification includes, for example, $C_{1-6}$ alkylthio groups optionally having 1–3 halogen atoms (e.g. F, Cl, Br, I) (for example, methylthio, difluoromethylthio, trifluoromethylthio, ethylthio, propylthio, isopropylthio, butylthio, 4,4,4-trifluorobutylthio, pentylthio, hexylthio, etc.).

The hydrocarbon group of the "optionally substituted hydrocarbon group" as the term is used for R, $R^1$ and $R^3$ in this specification includes groups available upon elimination of one hydrogen atom each from hydrocarbon compounds, such as alkyl, alkenyl, cycloalkyl, aryl, aralkyl and other groups. Preferred are acyclic or cyclic hydrocarbon groups of 1–16 carbon atoms such as the following.

a) $C_{1-6}$ alkyl (e.g. methyl, ethyl, propyl, isopropyl, butyl, isobutyl, sec-butyl, tert-butyl, pentyl, hexyl, etc.)

b) $C_{2-6}$ alkenyl (e.g. vinyl, allyl, isopropenyl, butenyl, isobutenyl, sec-butenyl, etc.)

c) $C_{2-6}$ alkynyl (e.g. propargyl, ethynyl, butynyl, 1-hexynyl, etc.)

d) optionally halogenated $C_{3-6}$ cycloalkyl; cyclohexyl may be fused to a benzene ring which may have 1–3 $C_{1-6}$ alkoxy (e.g. methoxy) groups.

e) $C_{6-14}$ aryl (e.g. phenyl, tolyl, xylyl, 1-naphthyl, 2-naphthyl, biphenyl, 2-indenyl, 2-anthryl, etc.); $C_{6-10}$ aryl (e.g. phenyl, etc.) in particular.

f) $C_{7-16}$ aralkyl (e.g. benzyl, phenethyl, diphenylmethyl, triphenylmethyl, 1-naphthylmethyl, 2-naphthylmethyl, 2-diphenylethyl, 3-phenylpropyl, 4-phenylbutyl, 5-phenylpentyl, etc.); benzyl in particular.

The substituent which may be present on the "optionally substituted hydrocarbon group" for R, $R^1$ and $R^3$ includes, for example, halogen (e.g. fluorine, chlorine, bromine, iodine), $C_{1-3}$ alkylenedioxy (e.g. methylenedioxy, ethylenedioxy, etc), nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino (e.g. methylamino, ethylamino, etc.), di-$C_{1-6}$ alkylamino (e.g. dimethylamino, diethylamino, etc.), $C_{1-6}$ alkylcarbonylamino (e.g. methylcarbonylamino, ethylcarbonylamino, etc.), $C_{1-6}$ alkyl-carbonyl (e.g. acetyl, ethylcarbonyl, etc.), carboxyl, $C_{1-6}$ alkoxy-carbonyl (e.g. methoxycarbonyl, ethoxycarbonyl, propoxycarbonyl, butoxycarbonyl, etc.), carbamoyl, mono-$C_{1-6}$ alkylcarbamoyl (e.g. methylcarbamoyl, ethylcarbamoyl, etc.), di-$C_{1-6}$ alkylcarbamoyl (e.g. dimethylcarbamoyl, diethylcarbamoyl, etc.), sulfo, $C_{1-6}$ alkylsulfonyl (e.g. methylsulfonyl, ethylsulfonyl, etc.), $C_{1-6}$ alkylsulfinyl (e.g. methylsulfinyl, ethylsulfinyl, etc.), $C_{6-10}$ aryl (e.g. phenyl, etc.), $C_{6-10}$ aryloxy (e.g. phenyloxy, etc.), 5- or 6-membered heterocyclic groups (e.g. rings containing 1–3 hetero atoms selected from among N, O and S in addition to C as ring members, such as 1-, 2- or 3-pyrrolidinyl, 2- or 4-imidazolidinyl, 2-, 3- or 4-pyrazolidinyl, 1-, 2-, 3- or 4-piperidyl, 1- or 2-piperazinyl, morpholinyl, 2-thienyl, 3-thienyl, 2-pyridyl, 4-pyridyl, 2-furyl, 3-furyl, pyrazinyl, 2-pyrimidinyl, 3-pyrrolyl, 2-imidazolyl, 3-pyridazinyl, 3-isothiazolyl, 3-isoxazolyl, etc.).

The hydrocarbon group of the "optionally substituted hydrocarbon group" may have 1–5, preferably 1–3, suitable substituents such as those mentioned above in substitutable positions, and where the number of substituents is 2 or more, the substituent groups may be the same or different.

The heterocyclic group of the "optionally substituted heterocyclic group" for R includes, for example, 5- to 10-membered (monocyclic or bicyclic) heterocyclic groups containing 1 to 3 hetero atoms of one or two kinds selected from among nitrogen, oxygen and sulfur in addition to carbon as ring members (e.g. non-aromatic heterocyclic groups such as 1-, 2- or 3-pyrrolidinyl, 2- or 4-imidazolidinyl, 2-, 3- or 4-pyrazolidinyl, 1-, 2-, 3- or 4-piperidyl, 1- or 2-piperazinyl, morpholinyl, etc. and aromatic heterocyclic (heteroaromatic) groups such as 2-thienyl, 3-thienyl, 2-pyridyl, 4-pyridyl, 2-furyl, 3-furyl, 4-quinolyl, 8-quinolyl, 4-isoquinolyl, pyrazinyl, 2-pyrimidinyl, 3-pyrrolyl, 2-imidazolyl, 3-pyridazinyl, 3-isothiazolyl, 3-isoxazolyl, 1-indolyl, 2-isoindolyl, etc.). Preferred are "heteroaromatic groups that may have a substituent or substituents". Thus, for example, 5- to 10-membered (monocyclic or bicyclic) heteroaromatic groups containing 1–3 hetero atoms of one or two kinds selected from among N, O and S in addition to C as ring members (e.g. 2-thienyl, 3-thienyl, 2-pyridyl, 4-pyridyl, 2-furyl, 3-furyl, 4-quinolyl, 8-quinolyl, 4-isoquinolyl, pyrazinyl, 2-pyrimidinyl, 3-pyrrolyl, 2-imidazolyl, 3-pyridazinyl, 3-isothiazolyl, 3-isoxazolyl, 1-indolyl, 2-isoindolyl, etc.) are preferred in many instances. Particularly, 5- or 6-membered heteroaromatic groups containing 1–3 hetero atoms selected from among N, O and S in addition to C (e.g. 2-thienyl, 3-thienyl, 2-pyridyl, 4-pyridyl, etc.) are selected in many instances.

The substituent that may be present on the heterocyclic group of the "optionally substituted heterocyclic group" typically includes the substituents mentioned for the optionally substituted aromatic group for $Ar^1$ and $Ar^2$.

The alkyl group for the "optionally substituted alkyl" for $R^2$ and $R^4$ includes, for example, straight-chain or branched lower($C_{1-6}$)alkyl groups (e.g. methyl, ethyl, propyl, isopropyl, butyl, isobutyl, sec-butyl, tert-butyl, pentyl, hexyl, etc.).

The substituent which may be present on the "alkyl" may for example be any of the substituent groups mentioned for the "optionally substituted hydrocarbon group" for R, $R^1$ and $R^3$, and $C_{6-10}$ aryl groups (e.g. phenyl etc).

The divalent aliphatic hydrocarbon group of at least 2 carbon atoms of the "divalent aliphatic hydrocarbon group containing at least 2 carbon atoms, which may have either oxygen or sulfur within the carbon chain" for P and Q includes a divalent group of at least 2 carbon atoms which is available on elimination of hydrogen atoms from the same or different carbon atoms of saturated or unsaturated aliphatic hydrocarbon and is preferably a hydrocarbon group containing 6 or fewer carbon atoms. More particularly, examples of the hydrocarbon group include:

(i) alkylene groups (e.g.

$-(CH_2)_2-$, $-(CH_2)_3-$, $-(CH_2)_4-$,

-continued

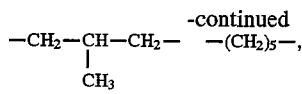

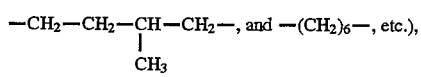

(ii) alkenylene groups (e.g.

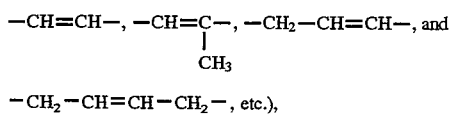

$-CH_2-CH=CH-CH_2-$, etc.), (iii) alkynylene groups (e.g. $-C\equiv C-$, $-CH_2-C\equiv C-$ and $-CH_2-C\equiv C-CH_2-$, etc.).
Preferred are $C_{2-6}$ alkylene groups (e.g. ethylene, propylene, trimethylene, tetramethylene, pentamethylene, etc.), $C_{2-6}$ alkenylene (e.g. vinylene, propenylene, etc.), and $C_{2-6}$ alkynylene groups (e.g. ethynylene, propynylene, etc.)

The "aliphatic hydrocarbon group of at least 2 carbon atoms" may have either oxygen or sulfur within the carbon chain. Thus, for example,

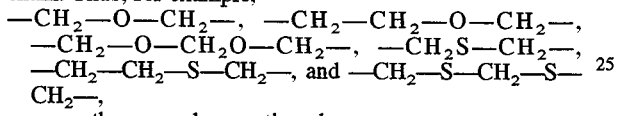

among others, can be mentioned.

The divalent aliphatic hydrocarbon group of the "divalent aliphatic hydrocarbon group which may have either oxygen or sulfur within the carbon chain" for $P^a$ and $Q^a$ includes a divalent group of one or more carbon atoms which is available on elimination of hydrogen atoms from the same or different carbon atoms of saturated or unsaturated aliphatic hydrocarbon and is preferably a group of 6 or fewer carbon atoms. More particularly, examples of the hydrocarbon group mentioned just above include:

(i) alkylene groups (e.g.

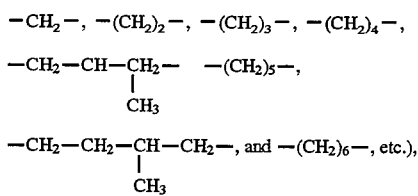

(ii) alkenylene groups (e.g.

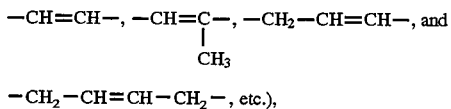

$-CH_2-CH=CH-CH_2-$, etc.), (iii) alkinylene groups (e.g. $-C\equiv C-$, $-CH_2-C\equiv C-$, and $-CH_2-C\equiv C-CH_2-$, etc.).
Preferred are $C_{2-6}$ alkylene (e.g. ethylene, propylene, trimethylene, tetramethylene, pentamethylene, etc.), $C_{2-6}$ alkenylene (e.g. vinylene, propenylene, etc.), and $C_{2-6}$ alkynylene (e.g. ethynylene, propynylene, etc.) in many instances.

The above "divalent aliphatic hydrocarbon group" may contain either oxygen or sulfur within the carbon chain. Thus, for example,

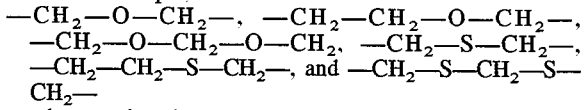

can be mentioned.

The "acyl group" for $R^{1a}$ and $R^{3a}$ includes, for example, $-CO-R$, $-CONH-R$, $-SO-R$, and $-SO_2-R$ wherein R represents an optionally substituted hydrocarbon group or an optionally substituted heterocyclic group. Particularly preferred is $-CO-R$ in many instances.

The nitrogen-containing heterocyclic group of the "optionally substituted nitrogen-containing heterocyclic group" for $R^1$ and $R^2$, $R^3$ and $R^4$, $R^{1a}$ and $R^2$, or $R^{3a}$ and $R^4$ means a fused or non-fused nitrogen-containing heterocyclic group that may contain 1 to 3 hetero atoms of one or two kinds selected from among nitrogen, oxygen and sulfur.

The substituent which may be present on the "nitrogen-containing heterocyclic group" includes the substituents which may be present on $Ar^1$ and $Ar^2$, among other groups. The "optionally substituted nitrogen-containing heterocyclic group" includes, for example, the following.

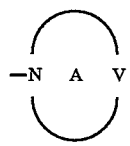

wherein ring A represents a 4- to 8-membered ring which may be substituted by 1 or 2 hydroxyl or oxo groups; V represents $>O$, $>C=O$,

or $>N-W$; W represents hydrogen, an optionally substituted hydrocarbon group or an optionally substituted heterocyclic group; and $W^a$ represents hydrogen or hydroxyl;

(ii)

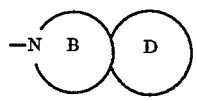

wherein ring B represents a 4- to 12-membered ring which may be substituted by 1 or 2 oxo groups; ring D represents an optionally substituted 4- to 12-membered aromatic ring; preferably

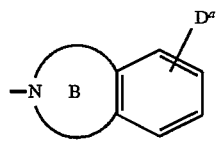

wherein ring B represents a 4- to 12-membered ring which may be substituted by 1 or 2 oxo groups; $D^a$ represents halogen (e.g. fluorine, chlorine, bromine, iodine), $C_{1-6}$ alkyl (e.g. methyl, ethyl, propyl, isopropyl, etc.), $C_{1-6}$ alkoxy (e.g. methoxy, ethoxy, propoxy, isopropoxy, etc.), $C_{1-3}$ alkylenedioxy (e.g. methylenedioxy, ethylenedioxy, etc.), nitro, amino or $C_{1-6}$ alkyl-carbonyl (e.g. acetyl, propionyl, etc.);

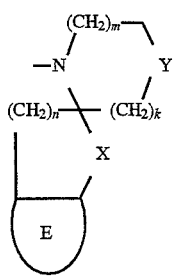

wherein ring E represents an optionally substituted 5- to 10-membered aromatic ring; X represents —CH₂—, —CO— or —CH(OH)—; Y represents —CH₂—, —O— or —NW$^b$— in which W$^b$ represents hydrogen or an optionally substituted C$_{1-6}$alkyl group; k+m represents an integer of 1 to 4; and n represents an integer of 1 to 3;

(iv) optionally substituted nitrogen-containing heteroaromatic groups. Among others, (i), (ii) and (iii) are preferred. More preferred are (i) and (iii). Particularly (iii) is preferred.

The "4- to 8-membered ring which may be substituted by 1 or 2 hydroxyl or oxo groups" for A includes, for example, the following.

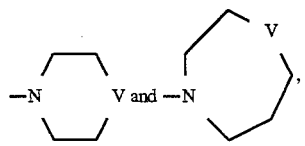

among others.

Preferred in many instances are

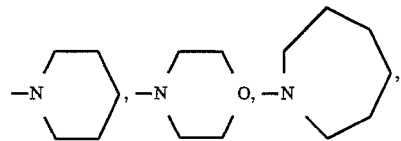

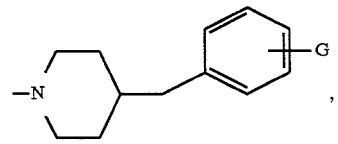

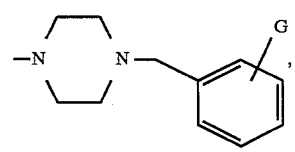

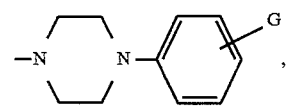

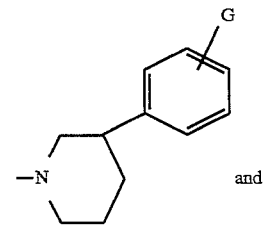

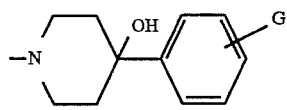

wherein V is as defined above and G represents halogen such as fluorine, chlorine, etc.; C$_{1-6}$ alkyl such as methyl, ethyl, propyl, isopropyl, etc.; or C$_{1-6}$ alkoxy such as methoxy, ethoxy, propoxy, isopropoxy, etc.

The "optionally substituted hydrocarbon group" for W includes the groups mentioned hereinbefore for the "optionally substituted hydrocarbon group" for R, R$^1$ and R$^3$. Particularly preferred are C$_{6-14}$ aryl (e.g. phenyl) and C$_{7-16}$ aralkyl (e.g. benzyl) groups. The substituent which may be present on this hydrocarbon group includes, for example, the substituents mentioned for the "hydrocarbon group" for R, R$^1$ and R$^3$.

The "optionally substituted heterocyclic group" for W includes, for example, 5- to 10-membered (monocyclic or bicyclic) heterocyclic groups containing 1 to 3 hetero atoms of 1 or 2 kinds selected from among nitrogen, oxygen and sulfur in addition to carbon as ring members. Specifically, 1-, 2- or 3-pyrrolidinyl, 2- or 4-imidazolidinyl, 2-, 3- or 4-pyrazolidinyl, 1-, 2-, 3- or 4-piperidyl, 1- or 2-piperazinyl, morpholinyl, 2-thienyl, 3-thienyl, 2-pyridyl, 4-pyridyl, 2-furyl, 3-furyl, 4-quinolyl, 8-quinolyl, 4-isoquinolyl, pyrazinyl, 2-pyrimidinyl, 3-pyrrolyl, 2-imidazolyl, 3-pyridazinyl, 3-isothiazolyl, 3-isoxazolyl, 1-indolyl, 2-isoindolyl, etc. can be mentioned. Preferred, among them, are aromatic groups. Particularly, 5- or 6-membered heteroaromatic groups containing 1 to 3 hetero atoms selected from among nitrogen, oxygen and sulfur in addition to carbon (e.g. 2-thienyl, 3-thienyl, 2-pyridyl, 4-pyridyl, etc.) are preferred in many instances.

The substituent which may be present on the heterocyclic group of the "optionally substituted heterocyclic group" typically includes the same substituents as mentioned for the "optionally substituted aromatic group" for Ar$^1$ and Ar$^2$.

The 4- to 12-membered ring which may be substituted by 1 or 2 oxo groups for B includes, for example, the following:

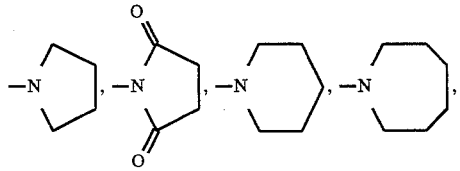

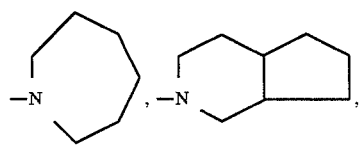

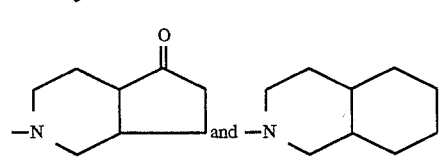

The aromatic ring of the "optionally substituted 4- to 12-membered aromatic ring" for D and E includes, for example, benzene ring, naphthalene ring, and 4- to 12-membered, preferably, 5- to 10-membered heteroaromatic rings (e.g. rings containing 1 to 3 hetero atoms selected from among N, O and S in addition to C as ring members, such as pyridine, pyrazine, pyrimidine, pyridazine, pyrrole, imidazole, pyrazole, thiophene, furan, thiazole, isothiazole, oxazole, isoxazole, quinoline, isoquinoline, indole, isoindole and other rings). Specifically, the following rings can be mentioned.

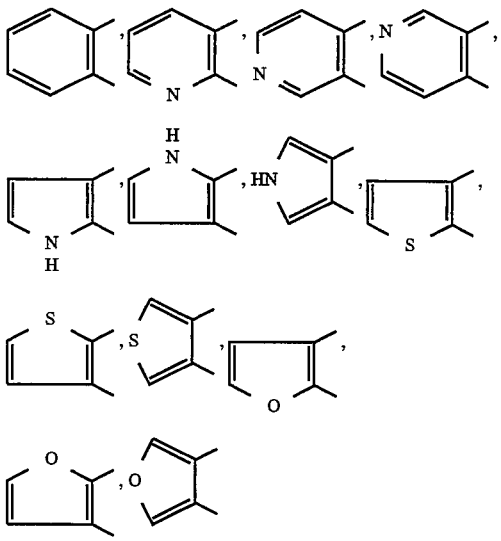

Ring D is preferably a benzene ring or a pyridine ring and more preferably is a benzene ring. Ring E is preferably a benzene ring.

The substituent which may be present on the "optionally substituted aromatic ring" includes the same substituents as mentioned hereinbefore for the "optionally substituted aromatic group" for $Ar^1$ and $Ar^2$.

The "optionally substituted alkyl groups" for $W^b$ includes, for example, $C_{1-6}$ alkyl groups which may be substituted by 1 to 5 substituents selected from the group consisting of halogen, $C_{1-3}$ alkylenedioxy, nitro, cyano, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl, $C_{6-10}$ aryl, $C_{6-10}$ aryloxy and 5- or 6-membered heterocyclic group.

The nitrogen-containing heteroaromatic group of the "optionally substituted nitrogen-containing heteroaromatic group" includes, for example, 5- to 10-membered (monocyclic or bicyclic) heteroaromatic groups containing one nitrogen atom other than carbon atom and optionally having preferably 1 to 3 hetero atoms of 1 or 2 kinds selected from among N, O and S as ring members. Specifically,

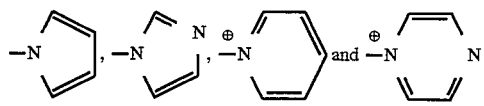

can be mentioned as examples. Where a counter ion is required, typically a halide ion (e.g. chloride ion, bromide ion or iodide ion) is employed.

The substituent which may be present on the "optionally substituted nitrogen-containing heteroaromatic group" can be the same substituents as those mentioned for the "optionally substituted aromatic group" for $Ar^1$ and $Ar^2$.

Referring to the formulae shown hereinbefore, $Ar^1$ and $Ar^2$ independently represent an optionally substituted aromatic group. The aromatic groups for $Ar^1$ and $Ar^2$ may each be a $C_{6-10}$ aryl group (e.g. phenyl), for instance.

The preferred "optionally substituted aromatic group" for $Ar^1$ and $Ar^2$ includes, for example, (i) $C_{6-14}$ aryl groups and (ii) 5- to 10-membered (monocyclic or bicyclic) heteroaromatic groups containing 1 to 3 hetero atoms selected from among nitrogen, oxygen and sulfur in addition to carbon as ring members, which groups may optionally have 1–3 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, amino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl, $C_{6-10}$ aryl and $C_{6-10}$ aryloxy.

In the same formula, P and Q independently represent a divalent aliphatic hydrocarbon group of at least 2 carbon atoms which may have either oxygen or sulfur within the carbon chain.

Preferred examples of P and Q are $C_{2-6}$ alkylene and $C_{2-6}$ alkenylene groups which may have either oxygen or sulfur within the carbon chain. Among them, $C_{2-6}$ alkylene and $C_{2-6}$ alkenylene groups are preferred, and $C_{3-5}$ alkylene groups (e.g. trimethylene, tetramethylene, etc.) are the more preferred in many instances.

In the formula (I') shown hereinbefore, $P^a$ and $Q^a$ independently represent a divalent aliphatic hydrocarbon group which may have either oxygen or sulfur within the carbon chain.

Preferred examples of $P^a$ and $Q^a$ are $C_{2-6}$ alkylene and $C_{2-6}$ alkenylene groups which may have either oxygen or sulfur within the carbon chain. Particularly preferred are $C_{2-6}$ alkylene and $C_{2-6}$ alkenylene groups. Among them, $C_{3-5}$ alkylene groups (e.g. trimethylene, tetramethylene, etc.) are more preferred.

In the formula shown hereinbefore, $R^1$ and $R^3$ independently represent i) an acyl group of —CO—R— or —CONH—R wherein R represents an optionally substituted hydrocarbon group or an optionally substituted heterocyclic group or ii) an optionally substituted hydrocarbon group.

$R^1$ preferably represents an optionally substituted hydrocarbon group.

$R^3$ preferably represents an acyl group of —CO—R or —CONH—R.

The "optionally substituted hydrocarbon group" for R, $R^1$ and $R^3$ includes (i) $C_{1-6}$ alkyl, (ii) $C_{2-6}$ alkenyl, (iii) $C_{2-6}$ alkinyl, (iv) $C_{3-6}$ cycloalkyl which may be fused with a phenyl ring, (v) $C_{6-14}$ aryl, and (vi) $C_{7-16}$ aralkyl, each optionally substituted by 1–3 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl, $C_{6-10}$ aryl, $C_{6-10}$ aryloxy and 5- or 6-membered heterocyclic groups.

$R^1$ is preferably a $C_{7-16}$ aralkyl, $C_{3-6}$ cycloalkyl or benzo-$C_{3-6}$ cycloalkyl group which may be substituted by 1 to 5 substituents selected from the group consisting of halogen, optionally halogenated $C_{1-6}$ alkyl, optionally halogenated $C_{1-6}$ alkoxy and $C_{1-6}$ alkoxy-carbonyl.

The preferred "optionally substituted heterocyclic group" for R includes, for example, 5- to 10-membered heterocyclic group which may have 1–3 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkyl-carbamoyl, sulfo, $C_{1-6}$ alkylsulfonyl, $C_{1-6}$ alkylsulfinyl, $C_{6-10}$ aryl and $C_{6-10}$ aryloxy.

A preferred example of $R^3$ is —CO—R. $R^3$ is preferably an acyl group of —CO—$R^b$ wherein $R^b$ is a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group which may be substituted by 1 to 5 substituents selected from the group consisting of halogen, $C_{1-3}$ alkylenedioxy, nitro, cyano, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl and 5- or 6-membered heterocyclic group. More preferred for $R^b$ is a $C_{7-16}$ aralkyl group which may have 1–3 substituents selected from among halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl, $C_{6-10}$ aryl and $C_{6-10}$ aryloxy. Particularly preferred is $C_{7-16}$ aralkyl group which may have 1–3 substituents selected from among halogen and $C_{1-6}$ alkoxy.

In the formula shown hereinbefore, $R^{1a}$ and $R^{3a}$ independently represent an acyl group or an optionally substituted hydrocarbon group. $R^{1a}$ is preferably an optionally substituted hydrocarbon group. $R^{3a}$ is preferably an acyl group.

In the formula, $R^2$ and $R^4$ independently represent hydrogen or an optionally substituted alkyl group.

The "optionally substituted alkyl" for $R^2$ and $R^4$ includes, for example, $C_{1-6}$ alkyl having 1 to 3 substituents selected from among halogen, nitro, cyano, $C_{3-6}$ cycloalkyl, $C_{1-6}$ alkoxy, $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl and $C_{6-10}$ aryl.

Preferably $R^2$ is, for example, (i) hydrogen or (ii) $C_{1-6}$ alkyl which may be substituted by phenyl (e.g. benzyl).

Preferably $R^4$ is hydrogen.

In the formula shown hereinbefore, j represents 0 or 1. Preferably, j is 0.

$R^1$ and $R^2$, $R^3$ and $R^4$, $R^{1a}$ and $R^2$, or $R^{3a}$ and $R^4$, taken together with the adjacent nitrogen atom, may form a nitrogen-containing heterocyclic group. This group

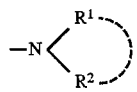

may for example be:

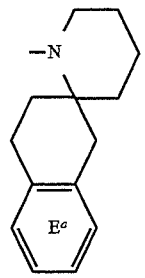

wherein Ring $E^a$ represents an optionally substituted benzene ring, preferably a benzene ring optionally having 1–4 substituents selected from among halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$alkylcarbamoyl, di-$C_{1-6}$ alkyl-carbamoyl, sulfo, $C_{1-6}$ alkylsulfonyl, $C_{1-6}$ alkylsulfinyl, $C_{6-10}$ aryl and $C_{6-10}$ aryloxy, or

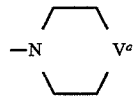 (ii)

wherein $V^a$ represents

or >N—W, in which W is a) hydrogen, b) a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group which may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl and 5- or 6-membered heterocyclic group, or c) a 5- to 10-membered heterocyclic group, containing, besides carbon atom, 1 to 4 hetero atoms selected from nitrogen atom, oxygen atom and sulfur atom, which may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl, $C_{6-10}$ aryl and $C_{6-10}$ aryloxy, and $W^a$ is hydrogen or hydroxyl. W preferably is phenyl group optionally having 1–3 substituents selected from among halogen and optionally halogenated $C_{1-6}$ alkoxy.

The following is a partial listing of some preferred compounds of formula (I).

(1) A compound of the formula:

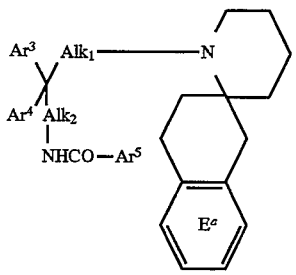

wherein $Ar^3$ and $Ar^4$ independently represent an optionally substituted phenyl; $Alk_1$ and $Alk_2$ independently represent a $C_{2-6}$ alkylene group; $Ar^5$ represents an optionally substituted aralkyl group; ring $E^a$ represents an optionally substituted benzene ring or a salt thereof.

Preferably, $Ar^3$ and $Ar^4$ are independently phenyl optionally having 1–3 substituents selected from among halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl, $C_{6-10}$ aryl and $C_{6-10}$ aryloxy. More preferably they are optionally halogenated phenyl.

$Ar^5$ is preferably a $C_{7-16}$ aralkyl group (e.g. benzyl) optionally having 1–3 substituents selected from among halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl, $C_{6-10}$ aryl and $C_{6-10}$ aryloxy. More preferably $Ar^{5'}$ is a $C_{7-16}$ aralkyl group optionally having 1–3 halogen or optionally halogenated $C_{1-3}$ alkoxy substituents.

Ring $E^a$ is preferably a benzene ring optionally having 1–3 substituents selected from among halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl, $C_{6-10}$ aryl and $C_{6-10}$ aryloxy. Preferably ring $E^a$ is a benzene ring which may be substituted by 1–3 substituents selected from among optionally halogenated $C_{1-3}$ alkoxy, $C_{1-3}$ alkyl-carbonyl and amino.

(2) A compound of the formula

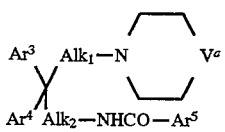

wherein $V^a$ represents

or >N—$W^a$, in which W is a) hydrogen, b) a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group which may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl and 5- or 6-membered heterocyclic group, or c) a 5- to 10-membered heterocyclic group, containing, besides carbon atom, 1 to 4 hetero atoms selected from nitrogen atom, oxygen atom and sulfur atom, which may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl, $C_{6-10}$ aryl and $C_{6-10}$ aryloxy, and $W^a$ is hydrogen or hydroxyl; the other symbols have the meanings defined hereinbefore or a salt thereof.

(3) A compound of the formula

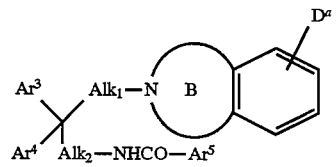

wherein ring B represents a 4- to 12-membered ring which may be substituted by 1 or 2 oxo groups; $D^a$ represents halogen, $C_{1-6}$ alkyl, $C_{1-6}$ alkoxy, $C_{1-3}$ alkylenedioxy, nitro, cyano or $C_{1-6}$ alkyl-carbonyl; the other symbols have the meanings defined hereinbefore, or a salt thereof.

Referring to the above-mentioned compounds (1) to (3), $Ar^3$ and $Ar^4$ each is preferably phenyl optionally having 1–3 substituents selected from among halogen and optionally halogenated $C_{1-6}$ alkoxy.

Referring, again, to the compounds (1) to (3), each of $Alk_1$ and $Alk_2$ is preferably a $C_{3-5}$ alkylene group (e.g. trimethylene, tetramethylene, etc.).

Referring, further, to the compounds (1) to (3), $Ar^5$ is preferably a $C_{7-16}$ aralkyl group which may be substituted by 1–3 substituents selected from among halogen and optionally halogenated $C_{1-6}$ alkoxy.

Referring to the compound (1), ring $E^a$ is preferably a benzene ring which may optionally be substituted by $C_{1-6}$ alkoxy optionally having 1–3 halogen atoms.

Referring to the compound (2), $W^a$ is preferably phenyl which may be substituted by halogen (preferably one halogen atom).

The following compounds can be mentioned as further preferred examples, although this is not an exhaustive listing, of course.

(1) 7-Acetylamino-1-{N-benzyl-N-[2-(6,7-dimethoxy-1,2,3,4-tetrahydronaphthyl)]amino}-4,4-diphenylheptane dihydrochloride, (2) 1'-(7-Acetylamino-4,4-diphenylheptyl)-3,4-dihydro-8-methoxyspiro[naphthalene-2(1H),2'-piperidine] dihydrochloride, (3) 1'-(7-Acetylamino-4,4-diphenylheptyl)-3,4-dihydro-6-methoxyspiro[naphthalene-2(1H),2'-piperidine] dihydrochloride, (4) 1'-(7-Acetylamino-4,4-diphenylheptyl)-3,4-dihydro-6,7-dimethoxyspiro[naphthalene-2(1H),2'-piperidine] dihydrochloride, (5) 3,4-Dihydro-6-methoxy-1'-(6-acetylamino-4,4-diphenylhexyl)spiro[naphthalene-2(1H),2'-piperidine] dihydrochloride, (6) 3,4-Dihydro-6,7-dimethoxy-1'-{4,4-diphenyl-7-[(phenylacetyl)amino]heptyl}spiro[naphthalene-2(1H),2'-piperidine] hydrochloride, (7) 3,4-Dihydro-6,7-dimethoxy-1'-{4,4-diphenyl-7-[(4-fluorophenylacetyl)amino]heptyl}spiro[naphthalene-2(1H),2'-piperidine] hydrochloride, (8) 3,4-Dihydro-6,7-dimethoxy-1'-{4,4-diphenyl-7-[(4-chlorophenylacetyl)amino]heptyl}spiro[naphthalene-2(1H),2'-piperidine] hydrochloride, (9) 3,4-Dihydro-6,7-dimethoxy-1'-{4,4-diphenyl-7-[(4-nitrophenylacetyl)amino]heptyl}spiro[naphthalene-2(1H),2'-piperidine] hydrochloride,

(10) 3,4-Dihydro-6,7-dimethoxy-1'-{4,4-diphenyl-7-[(4-methoxyphenylacetyl)amino]heptyl}spiro[naphthalene-2(1H),2'-piperidine] hydrochloride,

(11) 3,4-Dihydro-6,7-dimethoxy-1'-{7-[(3,4-dimethoxyphenylacetyl)amino]-4,4-diphenylheptyl}spiro[naphthalene-2(1H),2'-piperidine] hydrochloride,

(12) 3,4-Dihydro-6,7-dimethoxy-1'-{4,4-diphenyl-7-[(3,4-methylenedioxyphenylacetyl)amino]heptyl}spiro[naphthalene-2(1H),2'-piperidine] hydrochloride,

(13) 3,4-Dihydro-6,7-dimethoxy-1'-{4,4-diphenyl-7-[(phenoxyacetyl)amino]heptyl}spiro[naphthalene-2(1H),2'-piperidine] hydrochloride,

(14) 3,4-Dihydro-6,7-dimethoxy-1'-{4,4-diphenyl-7-[(3-thienylacetyl)amino]heptyl}spiro[naphthalene-2(1H),2'-piperidine] hydrochloride,

(15) 3,4-Dihydro-6,7-dimethoxy-1'-{4,4-diphenyl-7-[(3-phenylpropionyl)amino]heptyl}spiro[naphthalene-2(1H),2'-piperidine] hydrochloride,

(16) 3,4-Dihydro-6,7-dimethoxy-1'-{4,4-diphenyl-7-{[3-(4-methoxyphenyl)propionyl]amino}heptyl}spiro[naphthalene-2(1H),2'-piperidine] hydrochloride,

(17) 3,4-Dihydro-6,7-dimethoxy-1'-{4,4-diphenyl-7-{[3-(4-chlorophenyl)propionyl]amino}heptyl}spiro[naphthalene-2(1H),2'-piperidine] hydrochloride,

(18) 3,4-Dihydro-6,7-dimethoxy-1'-{4,4-diphenyl-7-{[3-(4-fluorophenyl)propionyl]amino}heptyl}spiro[naphthalene-2(1H),2'-piperidine] hydrochloride,

(19) 3,4-Dihydro-6,7-dimethoxy-1'-{4,4-diphenyl-7-[(1-naphthylacetyl)amino]heptyl}spiro[naphthalene-2(1H),2'-piperidine] hydrochloride,

(20) 3,4-Dihydro-6,7-dimethoxy-1'-{4,4-bis(4-fluorophenyl)-7-[(4-methoxyphenylacetyl)amino]heptyl}spiro[naphthalene-2(1H),2'-piperidine] hydrochloride,

(21) N-(7-(6,7-Dimethoxy-1,2,3,4-tetrahydronaphthalene-2-spiro-2'-piperidin-1'-yl)-4,4-diphenyl-5-heptenyl)-3-(4-methoxyphenyl)propionamide hydrochloride,

(22) (+)-3,4-Dihydro-6-methoxy-1'-{4,4-diphenyl-7-{[(4-methoxyphenyl)acetyl]amino}heptyl}spiro[naphthalene-2(1H),2'-piperidine],

(23) (−)-3,4-Dihydro-6-methoxy-1'-{4,4-diphenyl-7-{[(4-methoxyphenyl)acetyl]amino}heptyl}spiro[naphthalene-2(1H),2'-piperidine],

(24) (−)-3,4-Dihydro-6,7-dimethoxy-1'-{[4,4-diphenyl-7-{[(4-methoxyphenyl)acetyl]amino}heptyl}spiro[naphthalene-2(1H),2'-piperidine]-1-one,

(25) (−)-3,4-Dihydro-6,7-dimethoxy-1'-{4,4-diphenyl-7-{[(4-fluorophenyl)acetyl]amino}heptyl}spiro[naphthalene-2(1H),2'-piperidine],

(26) (+)-3,4-Dihydro-6,7-dimethoxy-1'-{4,4-diphenyl-7-{[(4-fluorophenyl)acetyl]amino}heptyl}spiro [naphthalene-2(1H),2'-piperidine],

(27) (−)-3,4-Dihydro-6,7-dimethoxy-1'-{4,4-diphenyl-7-{[3-(4-fluorophenyl)propionyl]amino}heptyl}spiro[naphthalene-2(1H),2'-piperidine],

(28) (+)-3,4-Dihydro-6,7-dimethoxy-1'-{4,4-diphenyl-7-{[3-(4-fluorophenyl)propionyl]amino}heptyl}spiro[naphthalene-2(1H),2'-piperidine],

(29) (+)-3,4-Dihydro-6,7-dimethoxy-1'-{7-{[3-(4-chlorophenyl)propionyl]amino}-4,4-diphenylheptyl}spiro[naphthalene-2(1H),2'-piperidine],

(30) (−)-3,4-Dihydro-6,7-dimethoxy-1'-{7-{[3-(4-chlorophenyl)propionyl]amino}-4,4-diphenylheptyl}spiro[naphthalene-2(1H),2'-piperidine],

(31) (−)-3,4-Dihydro-6,7-dimethoxy-1'-{4,4-diphenyl-7-{[3-(4-methoxyphenyl)propionyl]amino}heptyl}spiro[naphthalene-2(1H),2'-piperidine],

(32) (+)-3,4-Dihydro-6,7-dimethoxy-1'-{4,4-diphenyl-7-{[3-(4-methoxyphenyl)propionyl]amino}heptyl}spiro[naphthalene-2(1H),2'-piperidine].

In case compound (I) forms a salt and the salt is to be used as a drug, it is preferably a pharmaceutically acceptable salt.

The pharmaceutically acceptable salt includes, for example, salts with inorganic acids, such as the hydrochloride, sulfate, phosphate, diphosphate, hydrobromide, nitrate, etc., and salts with organic acids, such as the acetate, malate, maleate, fumarate, tartrate, succinate, citrate, lactate, methanesulfonate, p-toluenesulfonate, palmitate, salicylate, stearate, and so on.

While many synthetic technologies are feasible for producing the compounds described in this specification, a typical production technology is illustrated in the following schema 1.

Scheme 1

Process 1

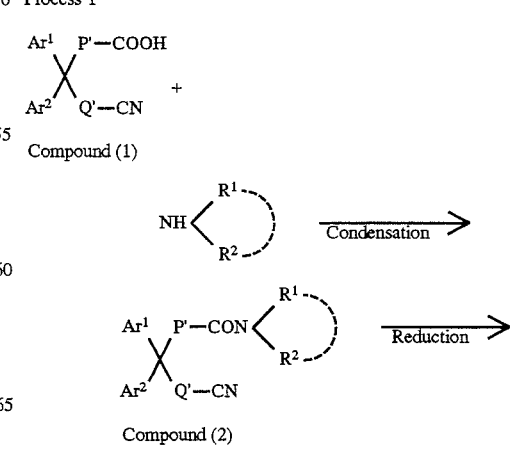

Compound (1)

Compound (2)

-continued
Scheme 1

Ar¹ P—N⟨R¹/R²⟩
    ╳
Ar² Q—NH₂

Compound (3)

$\xrightarrow{\text{Introduction of } R^3 \text{ and } R^4}$

Ar¹ P—N⟨R¹/R²⟩
    ╳
Ar² Q—N⟨R³/R⁴⟩

Compound (4)

Process 2

(In the above schema, P' and Q' correspond to P and Q, respectively, provided that the carbon number is reduced by one in each case; the other symbols have the meanings defined hereinbefore).

Ar¹ P—L
    ╳       + NH⟨R¹/R²⟩  $\xrightarrow{\text{Substitution}}$
Ar² Q'—CN

Compound (5)

Ar¹ P—N⟨R¹/R²⟩
    ╳                       $\xrightarrow{\text{Reduction}}$
Ar² Q'—CN Compound (6)

Compound (3) $\xrightarrow{\text{Introduction of } R^3 \text{ and } R^4}$ Compound (4)

Process 3

Ar¹ P—L
    ╳       + NH⟨R¹/R²⟩  $\xrightarrow{\text{Substitution}}$
Ar² Q—NHR⁵

Compound (7)

Ar¹ P—N⟨R¹/R²⟩
    ╳                       $\xrightarrow{\text{Deprotection}}$
Ar² Q—NHR⁵

Compound (4')

Ar¹ P—N⟨R¹/R²⟩
    ╳                       $\xrightarrow{\text{Introduction of } R^3 \text{ and } R^4}$ Compound (4)
Ar² Q—NH₂

The protective group of the acyl type, represented by $R^5$, may for example be formyl, acetyl, trifluoroacetyl, benzyloxycarbonyl, t-butoxycarbonyl or the like. The leaving group for L includes, for example, halogen such as chlorine, bromine or iodine.

The compound wherein $R^1$ is $R^{1a}$, $R^3$ is $R^{3a}$, P is $P^a$ and Q is $Q^a$ can also be produced by the above processes.

Process 1

The condensation reaction is carried out using 1–1.5 equivalents of a condensing agent, e.g. dicyclohexylcarbodiimide (DCC) or 1-ethyl-3-(3-dimethylaminopropyl) carbodiimide hydrochloride (WSC) or through a reactive intermediate of the carboxyl function. The reactive intermediate may for example be the acid anhydride, acid halide or activated ester.

The acid anhydride includes mixed acid anhydrides obtainable by reaction with lower-alkyl chlorocarbonate (e.g. ethyl chlorocarbonate, isopropyl chlorocarbonate, butyl chlorocarbonate, etc.) or with phenyl chlorocarbonate.

The acid halide may for example be the acid chloride or acid bromide. The acid chloride can be obtained by, for example, stirring the starting compound with at least 1 equivalent, preferably 3–10 equivalents, of oxalyl chloride, thionyl chloride or phosphorus pentachloride in the absence of a solvent or in an inert solvent such as dichloromethane at 0° C.–100° C., preferably 30° C.–60° C., for 0.5–3 hours.

The activated ester includes esters with 1-hydroxybenzotriazole (HOBT), pentafluorophenol and so on.

The condensation reaction is generally carried out by reacting the starting material with the corresponding amine in an inert solvent (e.g. dichloromethane, acetonitrile, etc.) stirring at 0°–80° C. for 0.5–20 hours. The reaction can be conducted more smoothly in the presence of a base. While the base that can be used includes both inorganic and organic bases, the preferred bases are triethylamine, diisopropylethylamine, 4-dimethylaminopyridine, N-methylmorpholine, 4-pyrrolidylpyridine, 1,8-diazabicyclo[5.4.0]-7-undecene (DBU), and DBN, among other bases.

The reduction reaction can be carried out by the known technology (as described in, for example, R. C. Larock, Comprehensive Organic Transformation, VCH Publishers Inc.), for example by using a metal hydride or the like. This reaction can be carried out in an inert solvent (e.g. ethers such as diethyl ether, diisopropyl ether, etc.) using at least one equivalent (preferably 4–10 equivalents) of a metal hydride at −20° C.–100° C., preferably 40° C.–80° C., for 5 minutes to 18 hours.

The preferred metal hydride includes lithium aluminum hydride, aluminum hydride, diborane and analogs thereof, among others.

Conversion to the objective compound of this invention can be achieved by utilizing per se known reactions (e.g. reduction, alkylation, acylation, sulfonylation, or reaction with an isocyanate) in combination.

The acylation and sulfonylation reactions can be carried out in substantially the same manner as the condensation reaction described above.

The reaction with an isocyanate can be carried out by reacting 1–1.5 equivalents of an isocyanate compound with the starting compound in an inert solvent at 0° C.–50° C. for 0.1–10 hours. The presence of a base (catalytic amount to 1 equivalent) such as triethylamine may assist in smooth progress of the reaction.

The alkylation reaction is conducted in an inert solvent at a temperature of 0° C.–100° C. for a time period of 5 minutes to 100 hours. The inert solvent includes alcoholic solvents (e.g. methanol, ethanol, propanol, etc.), ethereal solvents (e.g. diethyl ether, diisopropyl ether, etc.), halogen-containing solvents (e.g. dichloroethane, chloroform, etc.), aromatic solvents (e.g. toluene, xylene, etc.), acetonitrile, N,N-dimethylformamide (DMF), acetone, methyl ethyl ketone, dimethyl sulfoxide (DMSO) and so on. These solvents can be used singly or in combination. Particularly preferred are acetonitrile, DMF and acetone. The reaction can be conducted with greater efficiency in the presence of a base. For this purpose, both inorganic and organic bases are effective. The inorganic base that can be used includes the hydroxides, carbonates, hydrogen carbonates, and organic acid salts of alkali metals or alkaline earth metals and is preferably selected from among potassium carbonate, sodium carbonate, sodium hydroxide, potassium hydroxide, sodium hydrogen carbonate, and potassium hydrogen carbonate. The organic base is preferably a tertiary amine such as triethylamine.

The leaving group is preferably chloro, bromo, iodo, p-toluenesulfonyloxy, or methanesulfonyloxy. Depending upon conditions, monoalkylation and dialkylation can be selectively carried out.

Process 2

The substitution of the leaving group with an amine (HN—R$^1$R$^2$) can be carried out by the conventional technology used for alkylation of amines, for instance. For example, compound (5) is treated with the corresponding amine (HN—R$^1$R$^2$, 1–3 equivalents) in an inert solvent (e.g. DMF, acetone, or an ethereal solvent, used either alone or in combination), where necessary in the presence of 1–5 equivalents of a base (an inorganic base such as potassium carbonate or sodium hydroxide or an organic base such as triethylamine) stirring at a temperature of 0° C.–100° C., preferably 30° C.–60° C., for a time period of 30 minutes to 24 hours.

The reduction step of cyano group can be carried out by the per se known technology (as described in, for example, R. C. Larock, Comprehensive Organic Transformation, VCH Publishers Inc.). Among specific reactions are reduction by means of a metal hydride and catalytic hydrogenation.

The reaction with a metal hydride can be carried out in an inert solvent (e.g. an ethereal solvent such as diethyl ether, diisopropyl ether, etc.) at a temperature of –20° C.–100° C., preferably 40° C.–80° C., for a time period of 5 minutes to 18 hours.

The preferred metal hydride includes lithium aluminum hydride, aluminum hydride, diborane, and analogs thereof, among others.

The catalytic reduction can be carried out using a metal catalyst such as Raney nickel, platinum oxide, palladium metal, palladium-on-carbon or the like in an alcoholic or ethereal solvent at a temperature of 10° C.–100° C. and a pressure of 3–50 atmospheres for 1–18 hours. Where compound (6) contains a double bond, the bond may also be reduced by this catalytic reduction.

Process 3

Compound (7) can be transformed to compound (4') by a substitution reaction similar to the reaction of Process 2. If required, the protective group R$^5$ on the N atom can be eliminated by a conventional procedure and, then, R$^3$ and R$^4$ are introduced to give compound (4).

The procedure for the deprotection reaction is dependent on the kind of protective group but generally the deprotection can be easily carried out by the conventional hydrolysis reaction or catalytic reduction reaction.

The compound (4) thus obtained can be subjected to per se known reactions (e.g. hydrolysis, oxidation, reduction, alkylation, acylation, etc.) to introduce new substituent groups into R$^1$, R$^2$, R$^3$ and R$^4$.

The starting compounds necessary for the above production processes can be synthesized by various procedures. Typically, the following methods can be mentioned.

The amino compound (NH—R$^1$R$^2$) used in the above process 1 to 3 can be obtained by a per se known process. Spiro[naphthalene-2(1H),2'-piperidine], spiro[naphthalene-2(1H),2'-morpholine], and spiro[naphthalene-2(1H), 2'piperazine] can be synthesized according to the process described in the reference example. Spiro[indane-2(1H),2'-pyrrolidine] can be synthesized following the procedure written in Journal of Medicinal Chemistry, 21, 585(1978). Cis 1,2,3,4,4a,9,10,10a,-octahydrobenzo[f]quinoline was also obtained according to Synthesis, 494 (1986).

Among the compounds of compound (I), the compound wherein j is 1 can be obtained by standard procedures. For example, oxidation of the compound (4') in the above process 3 followed by deprotection and introduction of R$^3$ and R$^4$ can produce the compound (I) wherein j is 1.

Scheme 2

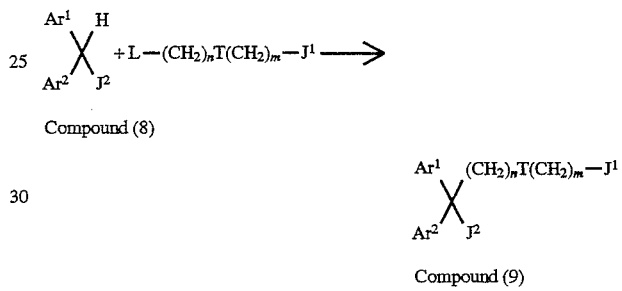

Compound (8)

Compound (9)

Compound (8) is reacted with an acrylate (e.g. methyl acrylate, ethyl acrylate, benzyl acrylate, etc.), acrylonitrile or L—(CH$_2$)$_n$T(CH$_2$)$_m$—J$^1$ (wherein T represents oxygen, sulfur, vinyl, or a chemical bond; n+m is an integer of 2 to 6; L represents a leaving group; J$^1$ represents lower alkoxycarbonyl or cyano) in a solvent, such as an ethereal solvent (e.g. diethyl ether, diisopropyl ether, etc.), DMF, DMSO, acetonitrile, an alcoholic solvent (e.g. methanol, ethanol, etc.) or an aromatic hydrocarbon (e.g. toluene, xylene, etc.), or a mixture of such solvents, in the presence of a base at a temperature of –20° C.–120° C. for 5 minutes–18 hours to provide compound (9).

The base that can be used includes strong bases such as sodium hydride, potassium hydride, potassium t-butoxide, lithium diisopropylamide, etc., inorganic bases such as the hydroxides, carbonates and hydrogencarbonates of alkali metals or alkaline earth metals such as sodium hydroxide, potassium hydroxide, potassium carbonate, etc., and organic bases such as triethylamine, DBU and so on.

When an acrylic ester or acrylonitrile is employed, the reaction is conducted in an alcoholic solvent, such as ethanol, in the presence of a catalytic amount to 5 equivalents of DBU under stirring at 40° C.–100° C. for 1–3 hours.

When L—(CH$_2$)$_n$T(CH$_2$)$_m$—J$^1$ is ethyl bromoacetate, ethyl iodopropionate, or ethyl 4-bromobutyrate, the reaction is conducted in an ethereal solvent, such as tetrahydrofuran (THF), in the presence of 1–3 equivalents of a strong base, such as sodium hydride, potassium hydride, etc., at a temperature of –20° C. to 20° C. for a time period of 5 minutes to 20 hours.

The substituent $J^2$ of compound (8) can be chain-extended by known technology. Taking the case in which $J^2$ is formyl, the carbon chain can be extended by means of, for example, Wittig reaction or Grignard reaction. For illustration, an example of synthesis of compound (I) starting from compound (10) is now presented.

The reaction with the Wittig reagent (e.g. ethyl triphenylphosphoranylideneacetate, ethyl diethylphosphonoacetate, etc.) can be conducted in an inert solvent (e.g. alcoholic solvents such as methanol, ethanol, propanol, etc.), ethereal solvents such as diethyl ether, diisopropyl ether, etc.) or a mixture of such solvents, if necessary in the presence of a base (e.g. potassium carbonate, sodium hydroxide, etc.; 1–2 equivalents), with stirring at 0° C.–80° C. for 10 minutes to 2 hours to give the unsaturated carboxylic acid derivative. The double bond in this compound (11) can be easily reduced by catalytic reduction.

The catalytic reduction reaction can be carried out using a catalytic amount of metal catalyst such as Raney nickel, platinum oxide, palladium metal, palladium-on-carbon, etc. in an alcoholic or ethereal solvent at 10° C.–100° C., preferably room temperature, preferably under a pressure of 1–5 atmospheres for 1–18 hours.

The hydrolysis reaction can be easily carried out under acidic or basic conditions.

The basic hydrolysis reaction can be typically conducted using at least one equivalent of an inorganic base such as sodium hydroxide, potassium hydroxide or lithium hydroxide in an alcoholic solvent such as ethanol or a mixture of such solvent with water at a temperature of 10° C.–100° C., preferably at ambient temperature, for 0.5–20 hours.

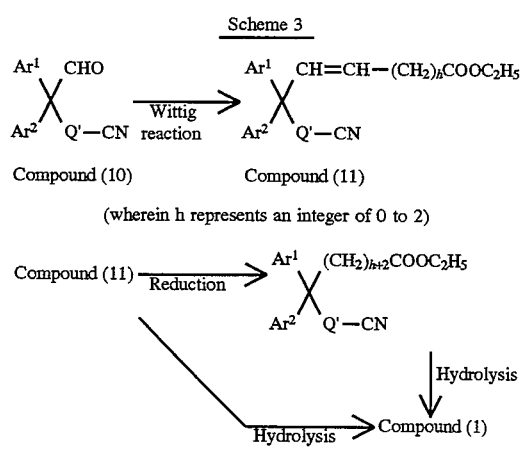

Scheme 3

Compound (10) → Wittig reaction → Compound (11)

(wherein h represents an integer of 0 to 2)

Compound (11) → Reduction → → Hydrolysis → Compound (1)

Compound (5), which is used in Process 2, can be prepared by subjecting compound (1) or an ester thereof [e.g. compound (11)] to selective reduction of the cyano group to give the alcohol (12) and, then, introducing a leaving group.

The reduction reaction can be carried out by known technology [as described in R. C. Larock, Comprehensive Organic Transformation, VCH Publishers Inc., and other literature]. Taking the reduction using a metal hydride as an example, the reaction can be conducted in an inert solvent (e.g. ethereal solvents such as diethyl ether, diisopropyl ether, etc.) at a temperature of –20° C. to 100° C., preferably 10° C. to 50° C., for 5 minutes to 18 hours.

The preferred metal hydride includes lithium aluminum hydride, aluminum hydride, diborane, lithium borohydride, sodium borohydride, and analogs thereof.

Introduction of a leaving group for the hydroxyl group can be carried out by per se known technology [as described in R. C. Larock, Comprehensive Organic Transformation, VCH Publishers Inc., among other literature]. The preferred leaving group is tosyloxy or iodo. Taking the transformation to tosyloxy as an example, the reaction can be conducted using p-toluenesulfonyl chloride (at least 1 equivalent, preferably 1–1.5 equivalents) in a halogenated hydrocarbon solvent (e.g. dichloromethane, dichloroethane, etc.) in the presence of a base (1–5 equivalents) such as triethylamine at a temperature of 0° C.–30° C. The transformation to iodo can be carried out either by reacting the tosyloxy compound with sodium iodide in an inert solvent (e.g. acetone) at 10° C.–100° C., preferably 30° C.–50° C., for 10 minutes to 6 hours or by reacting compound (12) with iodine (1–3 equivalents, preferably 1 equivalent) in an inert solvent in the presence of triphenylphosphine (1–5 equivalents, preferably 1 equivalent) at 10°–50° C. for 1–6 hours.

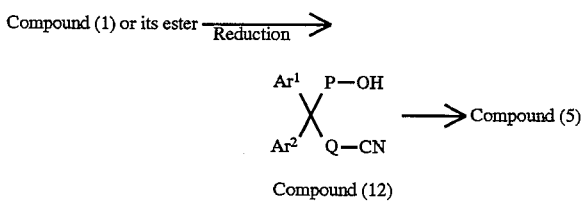

Scheme 4

Compound (1) or its ester → Reduction →

→ Compound (5)

Compound (12)

Compound (5'), which is compound (5) wherein P represents vinylene, can be derived from compound (9) by utilizing Grignard reaction.

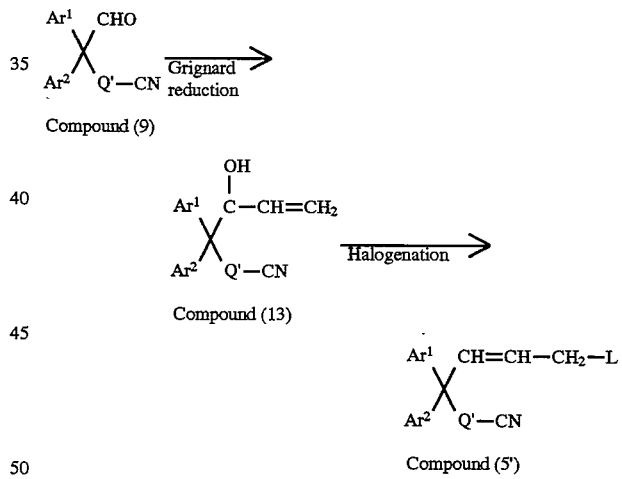

Scheme 5

Compound (9) → Grignard reduction →

Compound (13) → Halogenation →

Compound (5')

When the Grignard reaction is utilized, compound (9) is reacted with a vinylmetal reagent such as vinylmagnesium bromide, vinyllithium or the like in an ethereal solvent (e.g. THF, ethyl ether, etc.) at a temperature of –50° C. to 30° C., preferably –10° C. to 0° C., for 0.5–10 hours to give compound (13). This compound (13) can then be halogenated by reacting it with 1–5 equivalents of a suitable halogenating agent (e.g. thionyl chloride, phosphorus tribromide, etc.) in an inert solvent such as a halogenated hydrocarbon solvent (e.g. dichloroethane, chloroform, etc.) or an ethereal solvent (e.g. ethyl ether, THF, etc.) at a temperature of –20° C. to 30° C., preferably 0° C.–20° C., for 0.1–20 hours.

The starting compound (7) which is used in Process 3 can be typically synthesized from compound (1) or an ester thereof by way of reduction. The method of introducing an N-protective group is dependent on the kind of protective group but formyl, acetyl, benzyloxycarbonyl, etc., mentioned as preferred examples previously, can be introduced in the same manner as the acylation reaction described hereinbefore. Introduction of the leaving group L can be carried out by per se known technology (as described in R. C. Larock, Comprehensive Organic Transformation, VCH Publishers Inc., among other literature) or any technology analogous thereto.

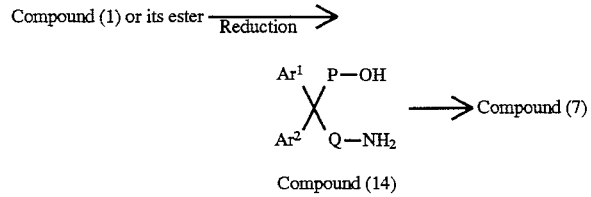

The objective compound of the invention and relevant starting materials as well as their salts can be separated and purified by known procedures such as solvent extraction, pH change, redistribution, salting-out, crystallization, recrystallization, chromatography, etc. The intermediate compounds need not be isolated but the reaction mixtures containing them can respectively be submitted to the next reaction steps.

Moreover, in case the starting compounds for any of the various reactions of the invention or for any of the reactions for synthesizing the various starting compounds, contain amino, carboxyl and/or hydroxyl groups, these functional groups may be previously protected with protective groups which are commonly used in peptide chemistry or related art. The desired compounds can then be obtained by removing such protective groups when needed.

The amino-protective group that can be used includes, for example, $C_{1-6}$ alkyl-carbonyl (e.g. formyl, acetyl, ethylcarbonyl, etc.), phenylcarbonyl, $C_{1-6}$ alkyloxycarbonyl (e.g. methoxycarbonyl, ethoxycarbonyl, etc.), benzoyl, $C_{7-10}$ aralkyl-carbonyl (e.g. benzylcarbonyl, etc), trityl, phthaloyl, and N,N-dimethylaminomethylene. These groups may respectively have 1-3 substituents selected from among, for example, halogen (e.g fluorine, chlorine, bromine, iodine, etc.) and nitro.

The carboxyl-protecting group which can be used includes, for example, $C_{1-6}$ alkyl (e.g. methyl, ethyl, n-propyl, isopropyl, butyl, tert-butyl, etc.), phenyl, trityl, and silyl. These groups may respectively have 1-3 substituents selected from among, for example, halogen (e.g. fluorine, chlorine, bromine, iodine), $C_{1-6}$ alkyl-carbonyl (e.g. formyl, acetyl, ethylcarbonyl, butylcarbonyl, etc.), and nitro.

The hydroxyl-protective group which can be used includes, for example, $C_{1-6}$ alkyl (e.g. methyl, ethyl, n-propyl, isopropyl, butyl, tert-butyl, etc.), phenyl, $C_{7-10}$ aralkyl (e.g. benzyl etc.), $C_{1-6}$ alkyl-carbonyl (e.g. formyl, acetyl, ethylcarbonyl, etc.), benzoyl, $C_{7-10}$ aralkyl-carbonyl (e.g. benzylcarbonyl), pyranyl, furanyl, and silyl. These groups may respectively have 1-3 substituents selected from among, for example, halogen (e.g. fluorine, chlorine, bromine, iodine), $C_{1-6}$ alkyl (e.g. methyl, ethyl, n-propyl, etc.), phenyl, $C_{7-10}$ aralkyl (e.g. benzyl), and nitro.

These protective groups can be removed by per se known procedures or any procedures analogous thereto. For example, a process using an acid or a base, reduction, or a process using ultraviolet radiation, hydrazine, phenylhydrazine, sodium N-methyldithiocarbamate, tetrabutylammonium fluoride, or palladium acetate can be utilized.

The compound (I) of this invention, as well as its pharmaceutically acceptable salt, inhibits secretion of gonadotropic hormone on the strength of its GnRH receptor antagonizing activity to control the blood steroid hormone concentrations. It therefore, can be safely used for the suppression of ovulation or prevention of implantation of ova or in the prevention and treatment of amenorrhea, prostatic cancer, prostatic hypertrophy, endometriosis, breast cancer, acne, precocious puberty, premenstrual syndrome, polycystic ovary syndrome, hyperandrogenism and other diseases in man. It is also effective in improving the quality of meat for food use.

The GnRH receptor antagonist composition of this invention, when used in judicious combination with a GnRH receptor agonist in mammals, especially in female persons, provides for adjustment and maintenance of endogenous gonadotropin at the proper level and is also useful for induction of ovulation.

The compound (I) of this invention, inclusive of its salt, has only a low toxic potential and a low risk of side effect. The oral acute toxicity ($LD_{50}$) of the compound of this invention in rats is not less than 100 mg/kg.

The compound (I) of this invention, inclusive of its salt, can be safely administered as it is or as a pharmaceutical composition containing a pharmaceutically acceptable carrier in various dosage forms such as tablets (inclusive of dragees and film-coated tablets), powders, granules, capsules (inclusive of soft capsules), solutions, injections, suppositories, controlled-release preparations, etc., by the oral route or by any other route. The dosage is dependent on the subject, route of administration, type and severity of disease, etc. but for the treatment of prostatic cancer, for instance, the recommended oral regimen for an adult patient (b.wt. 60 kg) is 0.1–500 mg/day, preferably 10–100 mg/day, to be administered once a day or in a few divided doses daily.

The pharmaceutically acceptable carrier includes a variety of organic and inorganic carriers or vehicles which are commonly used in the pharmaceutical field. Here, excipients, lubricants, binders, disintegrators, etc. are all subsumed in the concept of carrier for solid preparations, while solvents, solubilizers, suspending agents, isotonizing agents, buffers, smoothing agents (local analgesics), etc. can be used in the formulation of liquid preparations. Where necessary, various additives such as preservatives, antioxidants, coloring agents, sweeteners, etc. can also be added. The preferred excipient includes but is not limited to lactose, sucrose, D-mannitol, starch, crystalline cellulose, and light silicic anhydride. The preferred lubricant includes but is not limited to magnesium stearate, calcium stearate, talc, and colloidal silica. The preferred binder includes but is not limited to crystalline cellulose, sucrose, D-mannitol, dextrin, hydroxypropylcellulose, hydroxypropylmethylcellulose, and polyvinylpyrrolidone. The preferred disintegrator includes but is not limited to starch, carboxymethylcellulose, carboxymethylcellulose calcium, croscarmellose sodium, and carboxymethylstarch sodium. The preferred solvent includes but is not limited to water for injection, alcohol, propylene glycol, macrogols, sesame oil, and corn oil. The preferred solubilizer includes but is not limited to polyethylene glycol, propylene glycol, D-mannitol, benzyl benzoate, ethanol, trisaminomethane, cholesterol, triethanolamine, sodium carbonate, and sodium citrate. The preferred suspending agent includes surfactants such as stearyl triethanolamine, sodium lauryl sulfate, laurylaminopropionic acid, lecithin, glycerin monostearate, etc. and hydrophilic macromolecular substances such as polyvinyl alcohol, polyvinylpyrrolidone, carboxymethylcellulose sodium, methylcellulose, hydroxymethylcellulose, hydroxyethylcellulose, and hydroxypropylcellulose. The preferred isotonizing agent includes sodium chloride, glycerin and D-mannitol. The preferred buffer includes various buffer solutions such as phosphate, acetate, carbonate, and citrate buffers, to name but a few. The preferred soothing agent includes but is not limited to benzyl alcohol. The preferred preservative includes but is not limited to p-hydroxybenzoic esters, chlorobutanol, benzyl alcohol, phenethyl alcohol, dehydroacetic acid, and sorbic acid. The preferred antioxidant includes but is not limited to salts of sulfurous acid, and ascorbic acid.

EXAMPLES

The following reference, working and test examples are intended to describe this invention in further detail and should by no means be construed as defining the scope of the invention. Thus, various changes and modifications can be made without departing from the scope of the invention.

In the following reference and working examples, the term "room temperature" means any temperature within the range of 0° to 30° C. The other symbols have the following meanings.

| | |
|---|---|
| s: | singlet |
| d: | doublet |
| t: | triplet |
| q: | quartet |
| m: | multiplet |
| br: | broad |
| ABq: | AB quartet |
| dd: | double doublet |
| J: | coupling constant |
| Hz: | Herz |
| $CDCl_3$: | deuterochloroform |
| THF: | tetrahydrofuran |
| DMF: | N,N-dimethylformamide |
| DMSO: | dimethyl sulfoxide |
| $^1$H-NMR: | proton nuclear magnetic resonance |

Reference Example 1-1

3,3-Diphenyl-3-formylpropionitrile

To a solution of diphenylacetoaldehyde (1 g) in tetrahydrofuran (10 ml) was added a suspension of 60% sodium hydride (0.25 g) in tetrahydrofuran (5 ml) carefully dropwise under ice-cooling and stirring. After completion of dropwise addition, the mixture was further stirred for 20 minutes. Then, bromoacetonitrile (0.41 ml) was added and the mixture was further stirred for 30 minutes. The reaction mixture was poured in ice-water and the oil that had separated out was extracted into ethyl acetate. The organic layer was taken, washed with water, dried over anhydrous sodium sulfate, and concentrated to dryness. The group was purified by silica gel column chromatography to provide the title compound (0.85 g) as colorless oil.

Reference Example 1-2

4,4-Diphenyl-4-formylbutyronitrile

Diphenylacetaldehyde (25.6 g), acrylonitrile (12.5 ml), and 1,8-diazabicyclo[5,4,0]undec-7-ene (DBU:2.5 g) were stirred in isopropyl alcohol (250 ml) with warming at 70° C. for 6 hours. The reaction mixture was concentrated to dryness and the group was purified by silica gel column chromatography. The crude crystal crop obtained was washed with isopropyl ether to provide the title compound (19.8 g) as colorless crystals.

The structural formulas and NMR spectra of the respective compounds are shown in Table 1.

Reference Example 2-1

Ethyl 5-cyano-4,4-diphenyl-2-pentenoate 3,3-Diphenyl-3-formylpropionitrile (0.85 g) and (carbethoxymethylene)triphenylphosphorane (1.46 g) were heated in chloroform (20 ml) on reflux for 7 hours. The reaction mixture was then concentrated to dryness and the group was purified by silica gel column chromatography to provide the title compound (0.7 g) as colorless oil.

The compound of Reference Example 2-2 was synthesized in the same manner as Reference Example 2-1.

Reference Example 2-2

Ethyl 6-cyano-4,4-diphenyl-2-hexenoate

The structural formulas and NMR spectra of the above compounds are shown in Table 2.

Reference Example 3-1

(4-Chlorophenyl)phenylacetonitrile

To a mixture of mandelonitrile (5 g) and chlorobenzene (15.7 g) was added sulfuric acid (9.8 ml) dropwise while the temperature of the mixture was maintained at 5°–10° C. After completion of dropwise addition, the mixture was stirred for another 1.5 hours. This reaction mixture was poured in ice-water and the syrup that had separated out was extracted into ethyl acetate. The extract was washed with saturated aqueous sodium hydrogen carbonate solution, dried over anhydrous sodium sulfate, and concentrated to dryness. The group was purified by silica gel column chromatography to provide the title compound (3.6 g) as pale yellow syrup.

The compounds of Reference Examples 3-2 and 3 were synthesized in the same manner as Reference Example 3-1.

Reference Example 3-2

(4-Methoxyphenyl)phenylacetonitrile

Reference Example 3-3

Bis(4-chlorophenyl)acetonitrile

The structural formulas and NMR spectra of the respective compounds are shown in Table 3.

Reference Example 4-1

Ethyl 4-cyano-4,4-diphenylbutyrate

To a solution of diphenylacetonitrile (28 g) in ethanol (100 ml) were added DBU (6 ml) and ethyl acrylate (30 ml), and the mixture was heated and stirred at 80° C. for 16 hours. After cooling, 2N-hydrochloric acid (200 ml) was added and the mixture was extracted with isopropyl ether. The organic layer was washed with water, dried over anhydrous magnesium sulfate, and concentrated under reduced pressure. The crude crystal crop was recrystallized from hexaneisopropyl ether to provide the title compound (34 g).

The compounds of Reference Example 4-2 through 4-4 were synthesized in the same manner as Reference Example 4-1.

Reference Example 4-2

Ethyl 4-(4-chlorophenyl)-4-cyano-4-phenylbutyrate

Reference Example 4-3

Ethyl 4-cyano-4-(4-methoxyphenyl)-4-phenylbutyrate

Reference Example 4-4

Ethyl 4,4-bis(4-chlorophenyl)-4-cyanobutyrate

Reference Example 4-5

Ethyl 5-cyano-5,5-diphenylpentanoate

To a stirring solution of diphenylacetonitrile (1-g) in tetrahydrofuran (10 ml) was added 60% sodium hydride (0.25 g) in small portions under ice-cooling. After completion of dropwise addition, the mixture was stirred for 20 minutes. Then, ethyl 4-bromobutyrate (0.94 ml) was added dropwise under ice-cooling and the mixture was further stirred at room temperature for 15 minutes. This reaction mixture was poured into ice-water and the organic layer that had separated out was extracted with ethyl acetate. The extract was washed with water, dried over anhydrous sodium sulfate, and concentrated to dryness. The group was purified by silica gel column chromatography to provide the title compound (0.87 g) as colorless oil.

Reference Example 4-6

Ethyl 5-cyano-4,4-diphenylpentanoate

To a solution of ethyl 5-cyano-4,4-diphenyl-2-pentenoate (0.7 g) in ethanol (20 ml) was added 10% palladium-on-carbon (0.24 g), and the mixture was subjected to catalytic hydrogenation at atmospheric pressure and temperature. The catalyst in the reaction mixture was filtered off and the filtrate was concentrated to dryness. The group was purified by silica gel column chromatography to provide the title compound (0.6 g) as colorless oil.

The compound of Reference Example 4-7 was synthesized in same manner as Reference Example 4-6.

Reference Example 4-7

Ethyl 6-cyano-4,4-diphenylhexanoate

The structural formulas and NMR spectra of the respective compounds are shown in Table 4.

Reference Example 5-1

5-Amino-4,4-diphenylpentanol

To a stirred solution of ethyl 4-cyano-4,4-diphenylbutyrate (1.2 g) in tetrahydrofuran (30 ml) was added lithium aluminum hydride (0.44 g) in small portion under ice-cooling. After completion of dropwise addition, the mixture was heated and stirred at 60° C. for 3 hours. The reaction mixture was then cooled with ice again, and water (1 ml), 15% aqueous sodium hydroxide (3 ml) and water (1 ml) were added in succession. The insoluble matter that had separated out was filtered off and the filtrate was extracted with ethyl acetate and saturated aqueous sodium hydrogen carbonate. The organic layer was taken, washed with water, dried over anhydrous sodium sulfate, and concentrated to dryness. The group was washed with isopropyl ether to provide the title compound (0.82 g) as colorless powder.

The compounds of Reference Examples 5-2 through 5-7 were synthesized in the same manner as Reference Example 5-1.

Reference Example 5-2

5-Amino-4-(4-chlorophenyl)-4-phenylpentanol

Reference Example 5-3

5-Amino-4-(4-methoxyphenyl)-4-phenylpentanol

Reference Example 5-4

5-Amino-4,4-bis(4-chlorophenyl)pentanol

Reference Example 5-5

6-Amino-5,5-diphenylhexanol

Reference Example 5-6

6-Amino-4,4-diphenylhexanol

Reference Example 5-7

7-Amino-4,4-diphenylheptanol

The structural formulas and NMR spectra of the respective compounds are shown in Table 5.

Reference Example 6-1

5-Formylamino-4,4-diphenylpentanol

In formic acid (80 ml) was dissolved 5-amino-4,4-diphenylpentanol (10 g) followed by addition of acetic anhydride (13 ml) and the mixture was stirred at room temperature for 4 hours. This reaction mixture was concentrated to dryness and the group was partitioned into chloroform and water. The water layer was made basic by aqueous ammonia and extracted with chloroform. The extract was dried over anhydrous sodium sulfate and concentrated to dryness. The group was dissolved in ethanol (30 ml) and the solution was stirred in 1N-aqueous sodium hydroxide (20 ml) at room temperature for 20 minutes. This reaction mixture was diluted with water and the crystals that separated out were harvested by filtration. This crystal crop was washed serially with water and ethyl acetate to provide the title compound (9 g) as colorless powder.

The compounds of Reference Example 6-2 through 6-7 were synthesized in the same manner as Reference Example 7-1.

Reference Example 6-2

4-(4-Chlorophenyl)-5-formylamino-4-phenylpentanol

Reference Example 6-3

5-Formylamino-4-(4-methoxyphenyl)-4-phenylpentanol

Reference Example 6-4

4,4-Bis(4-chlorophenyl)-5-formylaminopentanol

Reference Example 6-5

6-Formylamino-5,5-diphenylhexanol

Reference Example 6-6

6-Formylamino-4,4-diphenylhexanol

Reference Example 6-7

7-Acetylamino-4,4-diphenylheptanol

The structural formulas, physical properties, and NMR spectra of the above compounds are shown in Table 6.

Reference Example 7-1

5-Formylamino-1-iodo-4,4-diphenylpentane

To a solution of 5-formylamino-4,4-diphenylpentanol (38.3 g) in methylene chloride (600 ml) were added p-toluenesulfonyl chloride (29.2 g), triethylamine (15 g), and 4-(dimethylamino)pyridine (catalytic amount), and the mixture was stirred at room temperature for 4 hours. The reaction mixture was concentrated to dryness, and sodium iodide (46.6 g) and acetone (600 ml) were added to the group. The reaction mixture was heated and stirred at 50° C. for 2 hours, after which it was concentrated to dryness. The group was extracted with ethyl acetate and water. The organic layer was taken, washed with an aqueous solution of sodium thiosulfate, dried over anhydrous sodium sulfate, and concentrated to dryness. The group was purified by silica gel column chromatography to provide the title compound (46.5 g) as yellow syrup. The compounds of Reference Example 7-3, 7-4, 7-6, 7-7, and 7-9 were respectively synthesized in the same manner as Reference Example 7-1.

Reference Example 7-3

4-(4-Chlorophenyl)-5-formylamino-1-iodo-4-phenylpentane

Reference Example 7-4

5-Formylamino-1-iodo-4-(4-methoxyphenyl)-4-phenylpentane

Reference Example 7-6

6-Formylamino-1-iodo-5,5-diphenylhexane

Reference Example 7-7

6-Formylamino-1-iodo-4,4-diphenylhexane

Reference Example 7-9

7-Acetylamino-1-iodo-4,4-diphenylheptane

Reference Example 7-2

1-Iodo-4,4-diphenyl-5-(tosylamino)pentane

5-Amino-4,4-diphenylpentanol (1 g), p-toluenesulfonyl chloride (1.65 g), triethylamine (1.2 ml), and 4-(dimethylamino)pyridine (catalytic amount) were stirred in methylene chloride (20 ml) at room temperature overnight. This reaction mixture was concentrated to dryness and the group was stirred with sodium iodide (0.7 g) in acetone (25 ml) at 50° C. for 24 hours. The reaction mixture was concentrated to dryness and the group was extracted using ethyl acetate and water. The organic layer was dried over anhydrous sodium sulfate and concentrated to dryness to provide the title compound (1 g) as light-yellow powder.

The compounds of Reference Example 7-8 and 7-5 were synthesized in the same manner as Reference Example 7-2.

Reference Example 7-8

1-Iodo-4,4-diphenyl-6-(tosylamino)hexane

Reference Example 7-5

4,4-Bis(4-chlorophenyl)-5-(formylamino)pentyl tosylate

The structural formulas, physical properties, and NMR spectra of the respective compounds are shown in Table 7.

Reference Example 8

5-Cyano-4,4-diphenylpentanol

To a stirred solution of ethyl 5-cyano-4,4-diphenylpentanoate (2 g) in tetrahydrofuran (25 ml) was added lithium aluminum hydride (0.37 g) in small portions under ice-cooling. After completion of addition, the mixture was further stirred for 30 minutes. While the reaction mixture was stirred under ice-cooling, water (0.9 ml), 15% aqueous sodium hydroxide (2.7 ml), and water (0.9 ml) were added in the order mentioned. The insoluble matter that separated out was filtered off and the filtrate was extracted with ethyl acetate and saturated aqueous sodium hydrogen carbonate. The organic layer was washed with saturated aqueous sodium chloride, dried over anhydrous sodium sulfate, and concentrated to dryness. The group was purified by silica gel column chromatography to provide the title compound (1.3 g) as colorless syrup.

$^1$H-NMR(CDCl$_3$, δ): 1.25–1.40(2H,m), 2.34–2.43(2H, m), 3.12(2H,s), 3.61(2H,t), 7.15–7.37(10H,m)

Reference Example 9

3,3-Diphenyl-6-iodohexanenitrile

To a solution of triphenylphosphine (1.68 g) in methylene chloride (30 ml) and imidazole (0.44 g) was added iodine (1.62 g). To this mixture was added a solution of 5-cyano-4,4-diphenylpentanol (1.3 g) in methylene chloride (5 ml) dropwise. After completion of dropwise addition, the mixture was stirred at room temperature overnight. The reaction mixture was washed with a saturated aqueous solution of sodium thiosulfate, dried over anhydrous sodium sulfate, and concentrated to dryness. To the group was added isopropyl ether, and the insoluble matter was filtered off. The filtrate was concentrated to dryness to provide the title compound (1.5 g) as colorless syrup.

$^1$H-NMR(CDCl$_3$, δ): 1.49–1.64(2H,m), 2.38–2.47(2H, m), 3.11(2H,s), 3.12(2H,t), 7.13–7.39(10H,m)

Reference Example 10

6-Cyano-4,4-diphenylhexanoic Acid

To a solution of ethyl 6-cyano-4,4-diphenylhexanoate (25.5 g) in ethanol (400 ml) was added 1N-aqueous sodium hydroxide solution (120 ml) and the mixture was heated and stirred at 60° C. for 1 hour. After completion of the reaction, the reaction mixture was concentrated under reduced pressure and the group was made acidic to with 1N-hydrochloric acid and extracted with ethyl acetate (200 ml×2). The extract was washed with saturated aqueous sodium chloride solution, dried over anhydrous sodium sulfate, and concentrated to dryness. The group (25 g) was recrystallized from chloroform-hexane to provide the title compound (22 g) as white powder.

m.p. 119°–120° C. $^1$H-NMR(CDCl$_3$, δ): 1.95–2.10(4H, m), 2.37–2.50(4H,m), 7.10–7.40(10H,m)

Reference Example 11

3,4-Dihydro-6,7-dimethoxy-1'-(6-cyano-4,4-diphenylhexanoyl)spiro[naphthalene-2(1H),2'-piperidine]

To a stirred solution of 6-cyano-4,4-diphenylhexanoic acid (1.6 g) in chloroform (20 ml) was added thionyl chloride (0.79 ml) dropwise under ice-cooling. After completion of dropwise addition, the mixture was further stirred at room temperature for 1 hour. This reaction mixture was concentrated to dryness under reduced pressure and the group was dissolved in methylene chloride (5 ml). This solution was added dropwise to a solution of 3,4-dihydro-6,7-dimethoxyspiro[naphthalene-2(1H),2'-piperidine] hydrochloride (1.96 g) and triethylamine (1.33 g) in methylene chloride (25 ml) under ice-cooling and stirring. After completion of dropwise addition, the mixture was further stirred at room temperature for 30 minutes. This reaction mixture was concentrated to dryness and the group was purified by silica gel column chromatography to provide the title compound (1.29 g) as light-yellow syrup.

$^1$H-NMR(CDCl$_3$, δ): 1.52–1.68(6H,m), 1.91–2.09(4H, m), 2.34–2.60(5H,m), 2.62–2.98(4H,m), 3.08–3.16 (2H,m), 3.83(6H,s), 3.96(1H,d), 6.55,6.58 (1H,each,s), 7.11–7.37 (10H,m)

Reference Example 12

3,4-Dihydro-6-methoxy-1'-(5-cyano-4,4-diphenylpentyl)spiro[naphthalene-2(1H),2'-piperidine]hydrochloride 3,3-Diphenyl-6-iodohexanenitrile (1.5 g), 3,4-dihydro-6-methoxyspiro[naphthalene-2(1H),2'-piperidine] hydrochloride (1.39 g), triethylamine (0.53 g), and potassium carbonate (0.72 g) were stirred in acetonitrile (25 ml) at 70° C. overnight. The insoluble matter in the reaction mixture was filtered off and the filtrate was concentrated to dryness. The group was purified by silica gel column chromatography to provide the hydrochloride salt of the title compound (0.7 g) as light-yellow powder.

$^1$H-NMR(CDCl$_3$, δ): 1.09–1.25(2H,m), 1.38–1.70(7H, m), 1.78–1.95(1H,m), 2.13–2.80(10H,m), 3.08(2H,s), 3.77 (3H,s), 6.62–6.71(2H,m), 6.95(1H,d), 7.12–7.37(10H,m)

Elemental analysis: C$_{33}$H$_{38}$N$_2$O.HCl.H$_2$O. Calcd. C 74.38; H 7.88; N 5.38. Found C 74.34; H 7.75; N 5.25

TABLE 1

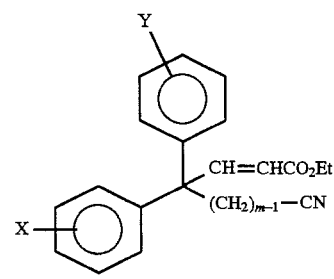

| Reference Example | X | Y | m | $^1$H-NMR (δ ppm, CDCl$_3$) |
|---|---|---|---|---|
| 1-1 | H | H | 2 | 3.24(2H, s), 7.19–7.50(10H, m), 9.79(1H, s) |
| 1-2 | H | H | 3 | 2.04–2.13(2H, m), 2.64–2.74(2H, m), 7.11–7.45(10H, m), 9.79(1H, s) |

TABLE 2

| Reference Example | X | Y | m | $^1$H-NMR (δ ppm, CDCl$_3$) |
|---|---|---|---|---|
| 2-1 | H | H | 2 | 1.29(3H, t), 3.28(2H, s), 4.21(2H, q), 5.71, 7.52(1H each, d), 7.14–7.41(10H, m) |
| 2-2 | H | H | 3 | 1.29(3H, t), 2.09–2.18(2H, m), 2.65–2.77(2H, m), 4.20(2H, q), 5.63, 7.47(1H each, d), 7.09–7.19(4H, m), 7.22–7.40(6H, m) |

TABLE 3

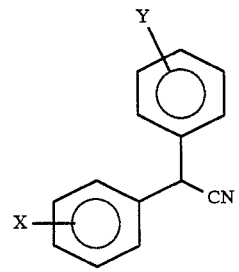

| Reference Example | X | Y | $^1$H-NMR (δ ppm, CDCl$_3$) |
|---|---|---|---|
| 3-1 | 4-Cl | H | 5.11(1H, s), 7.23–7.42(9H, m) |
| 3-2 | 4-MeO | H | 3.80(3H, s), 5.10(1H, s), 6.85–6.94(2H, m), 7.20–7.40(7H, m) |
| 3-3 | 4-Cl | 4-Cl | 5.10(1H, s), 7.20–7.40(8H, m) |

TABLE 4

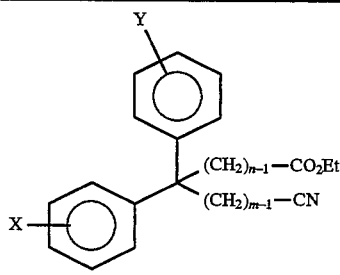

| Reference Example | X | Y | m | n | $^1$H-NMR ($\delta$ ppm, $CDCl_3$) |
|---|---|---|---|---|---|
| 4-1 | H | H | 1 | 3 | 1.23(3H, t), 2.40–2.51(2H, m), 2.71–2.82(2H, m), 4.11(2H, q), 7.26–7.43(10H, m) |
| 4-2 | 4-Cl | H | 1 | 3 | 1.23(3H, t), 2.38–2.48(2H, m), 2.78–2.88(2H, m), 4.10(2H, q), 7.29–7.40(9H, m) |
| 4-3 | 4-MeO | H | 1 | 3 | 1.60–1.85(2H, m), 2.23–2.50(2H, m), 3.69(2H, t), 3.79(3H, s) 6.88–6.90(2H, m), 7.10–7.40(7H, m) |
| 4-4 | 4-Cl | 4-Cl | 1 | 3 | 1.23(3H, t), 2.41(2H, m), 2.70(2H, m), 4.10(2H, q), 7.20–7.40(8H, m) |
| 4-5 | H | H | 1 | 4 | 1.24(3H, t), 1.69–1.86(2H, m), 2.38(2H, t), 2.38–2.48(2H, m), 4.12(2H, q), 7.23–7.43(10H, m) |
| 4-6 | H | H | 2 | 3 | 1.21(3H, t), 2.09, 2.66(2H each, t), 3.09(2H, s), 4.06(2H, q), 7.16–7.39(10H, m) |
| 4-7 | H | H | 3 | 3 | 1.22(3H, t), 1.95–2.06(4H, m), 2.36–2.48(4H, m), 4.07(2H, q), 7.09–7.37(10H, m) |

TABLE 5

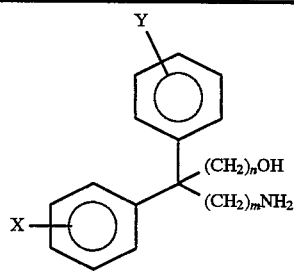

| Reference Example | X | Y | m | n | Melting Point(°C.) | $^1$H-NMR ($\delta$ ppm, $CDCl_3$) |
|---|---|---|---|---|---|---|
| 5-1 | H | H | 1 | 3 | syrup | |
| 5-2 | 4-Cl | H | 1 | 3 | syrup | 1.17–1.33(2H, m), 1.55(2H, br s), 2.14–2.44(2H, m) 3.31(2H, s), 3.56(2H, t), 7.07–7.38(9H, m) |
| 5-3 | 4-MeO | H | 1 | 3 | syrup | 1.20–1.35(2H, m), 2.15–2.25(2H, m), 3.31(2H, s), 3.57(2H, t), 3.79(3H, s), 6.78–6.85(2H, m), 7.05–7.35(7H, m) |
| 5-4 | 4-Cl | 4-Cl | 1 | 3 | syrup | 1.10–1.30(2H, m), 1.55(2H, br s), 2.14–2.24(2H, m), 3.29(2H, s), 3.55(2H, t), 7.00–7.30(8H, m) |
| 5-5 | H | H | 1 | 4 | syrup | 1.01–1.18(2H, m), 1.42–1.65(4H, m), 2.09–2.20(2H, m), 3.33(2H, s), 3.56 (2H, t), 7.12–7.35(10H, m) |
| 5-6 | H | H | 2 | 3 | syrup | 1.14–1.32(2H, m), 2.10–2.26(2H, m), 2.24–2.39(2H, m), 2.37–2.51(2H, m), 3.15(3H, s), 3.51(2H, t), 7.07–7.30(10H, m) |
| 5-7 | H | H | 3 | 3 | syrup | 1.10–1.31(4H, m), 2.05–2.22(4H, m), 2.66, 3.53(2H each, t), 3.01(3H, brs), 7.06–7.30(10H, m) |

TABLE 6

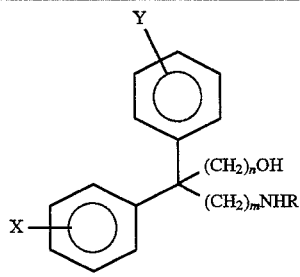

| Reference Example | X | Y | R | m | n | Melting Point(°C.) | $^1$H-NMR (δ ppm, CDCl$_3$) |
|---|---|---|---|---|---|---|---|
| 6-1 | H | H | CHO | 1 | 3 | 151–152 | 1.32(2H, m), 2.16(2H, m), 3.55(2H, t), 4.05(2H, d), 5.10–5.30(1H, m), 7.10–7.40(10H, m), 8.08(1H, d) |
| 6-2 | 4-Cl | H | CHO | 1 | 3 | 159–161 | 1.00–1.23(2H, m), 2.03(2H, t), 3.30(2H, q), 3.88(2H, dd), 4.33(1H, t), 7.10–7.37(9H, m), 7.48(1H, br t), 7.87(1H, d) |
| 6-3 | 4-MeO | H | CHO | 1 | 3 | syrup | 1.20–1.40(2H, m), 2.08–2.20(2H, m), 3.54(2H, br t), 3.79(3H, s), 4.01 (2H, dt), 5.20–5.30(1H, br s), 6.80–6.88(2H, m), 7.00–7.35(7H, m), 8.07 (1H, d) |
| 6-4 | 4-Cl | 4-Cl | CHO | 1 | 3 | 175–178 | 1.00–1.20(2H, m), 2.04(2H, t), 3.30(2H, q), 3.86(2H, d), 4.34(1H, t), 7.10–7.40(8H, m), 7.55(1H, br t), 7.88(1H, d) |
| 6-5 | H | H | CHO | 1 | 4 | syrup | 1.04–1.22(2H, m), 1.40–1.56(2H, m), 1.90–2.18(2H, m), 3.54(2H, t), 4.06 (2H, d), 5.20(1H, br t), 7.10–7.37(10H, m), 8.08(1H, d) |
| 6-6 | H | H | CHO | 2 | 3 | syrup | 1.20–1.38(2H, m), 2.20–2.40(4H, m), 3.06(2H, q), 3.57(2H, t), 5.49 (1H, br), 7.10–7.34(10H, m), 7.99(1H, d) |
| 6-7 | H | H | Ac | 3 | 3 | syrup | 1.12–1.30(4H, m), 1.90(3H, s), 2.02–2.21(5H, m), 3.15(2H, q), 3.55(2H, t), 5.49(1H, br t), 7.11–7.30(10H, m) |

TABLE 7

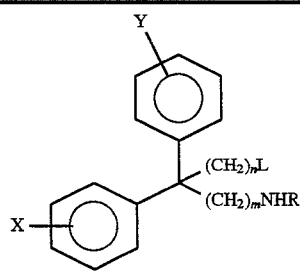

| Reference Example | X | Y | R | L | m | n | Melting Point(°C.) | $^1$H-NMR (δ ppm, CDCl$_3$) |
|---|---|---|---|---|---|---|---|---|
| 7-1 | H | H | CHO | I | 1 | 3 | syrup | 1.49–1.65(2H, m), 2.12–2.25(2H, m), 3.10(2H, t), 4.04(2H, d), 5.07 (1H, br t), 7.11–7.40(10H, m), 8.11(1H, d) |
| 7-2 | H | H | Ts | I | 1 | 3 | syrup | 1.31–1.49(2H, m), 2.15–2.26(2H, m), 2.44(3H, s), 2.99(2H, t), 3.54 (2H, d), 3.87(1H, t), 7.05, 7.06, 7.64(2H each, d), 7.20–7.35(8H, m) |
| 7-3 | 4-Cl | H | CHO | I | 1 | 3 | syrup | 1.46–1.63(2H, m), 2.10–2.22(2H, m), 3.10(2H, t), 4.01(2H, d), 5.08 (1H, br t), 7.06–7.39(9H, m), 8.10(1H, d) |
| 7-4 | 4-MeO | H | CHO | I | 1 | 3 | syrup | 1.45–1.65(2H, m), 2.09–2.22(2H, m), 3.09(2H, t), 3.80(3H, s), 3.99 (2H, d), 5.00–5.15 (1H, br s), 6.80–6.90(2H, m), 7.00–7.38(7H, m), 8.10(1H, d) |
| 7-5 | 4-Cl | 4-Cl | CHO | OTs | 1 | 3 | syrup | 1.30–1.60(2H, m), 2.00–2.20(2H, m), 2.45(3H, s), 3.90–4.00(4H, m), 5.00–5.20(1H, br s), 7.00–7.40(10H, m), 7.72(2H, m), 8.08(1H, d) |
| 7-6 | H | H | CHO | I | 1 | 4 | syrup | 1.07–1.28(2H, m), 1.65–1.85(2H, m), 2.00–2.13(2H, m), 3.07(2H, t), 4.04(2H, d), 5.02(1H, br s), 7.10–7.39(10H, m), 8.10(1H, d) |
| 7-7 | H | H | CHO | I | 2 | 3 | syrup | 1.43–1.61(2H, m), 2.19–2.40(4H, m), 3.08(2H, q), 3.11(2H, t), 5.19 (1H, br s), 7.12–7.36(10H, m), 7.99(1H, d) |
| 7-8 | H | H | Ts | I | 2 | 3 | syrup | 1.32–1.49(2H, m), 2.02–2.17(2H, m), 2.21–2.34(2H, m), 2.42(3H, s), 2.62–2.78(2H, m), 3.05(2H, t), 4.26(1H, t), 7.06, 7.07, 7.61 (2H each, d), 7.12–7.32(8H, m) |
| 7-9 | H | H | Ac | I | 3 | 3 | syrup | 1.12–1.28(2H, m), 1.40–1.56(2H, m), 1.91(3H, s), 2.04–2.23(4H, m), 3.10(2H, t), 3.17(2H, q), 5.25(1H, br s), 7.11–7.32(10H, m) |

Reference Example 13-1

1-Benzoyl-2-(2-phenylethyl)-2-piperidinecarbonitrile

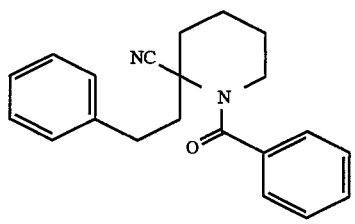

To 200 ml of a solution of lithium diisopropylamide (140 mmol) in tetrahydrofuran was added 15 g of solid 1-benzoyl-2-piperidinecarbonitrile at −78° C. and the mixture was stirred for 30 minutes. Then, 100 ml of a solution of 33.2 g of phenethyl iodide in tetrahydrofuran was added dropwise at −78° C. After completion of dropwise addition, the temperature of the reaction mixture was gradually increased to 0° C. The reaction mixture was diluted with water and the organic layer was separated. The aqueous layer was further extracted with ethyl acetate. The pooled organic layer was dried over magnesium sulfate and filtered and the solvent was distilled off. The group was purified by silica gel column chromatography using ethyl acetate-hexane (1:2) as the eluent. The active fraction was concentrated under reduced pressure and the solid group was recrystallized from ethyl acetate-hexane to provide 17.3 g of colorless crystals.

m.p. 65°–67° C. $^1$H-NMR (CDCl$_3$, δ): 1.52–2.00(4H,m), 2.19(2H,t, J=6 Hz), 2.37–2.98(4H,m), 3.29–3.57(2H,m), 7.13–7.56(10H,m)

Elemental analysis: $C_{21}H_{22}N_2O$. Calcd. C 79.21; H 6.96; N 8.80. Found C 79.13; H 6.89; N 8.64

The following compounds were synthesized in the same manner as Reference Example 6-1.

Reference Example 13-2

1-Benzoyl-2-[2-(3-methoxyphenyl)ethyl]-2-piperidinecarbonitrile

Reference Example 13-3

1-Benzoyl-2-[2-(3,4-dimethoxyphenyl)ethyl]-2-piperidinecarbonitrile

Reference Example 13-4

1-Benzoyl-2-[2-thienylethyl]-2-piperidinecarbonitrile

The structural formulas, physical properties, and NMR spectra of the above compounds are shown in Table 8.

TABLE 8

| Reference Example | Structural Formula | Melting Point(°C.) | NMR (δ ppm, CDCl$_3$) | Elemental Analysis [Cald./Found] C | H | N |
|---|---|---|---|---|---|---|
| 13-2 | | 82–84 | 1.55–1.98(4H, m), 2.19(2H, t, J=6Hz), 2.36–2.96(4H, m), 3.27–3.57(2H, m), 3.79(3H, s), 6.71–6.85(3H, m), 7.14–7.25(1H, m), 7.36–7.56(5H, m) | $C_{22}H_{24}N_2O_2$ 75.58 (75.83 | 6.98 6.94 | 7.92 8.04) |
| 13-3 | | oil | 1.54–1.99(4H, m), 2.19(2H, t, J=6Hz), 2.34–2.94(4H, m), 3.27–3.56(2H, m), 3.85(3H, s), 3.87(3H, s), 6.72–6.83(3H, m), 7.37–7.58(5H, m) | $C_{23}H_{26}N_2O_2$ 73.21 (72.99 | 7.16 6.92 | 7.35 7.40) |
| 13-4 | | oil | 1.50–1.97(4H, m), 2.17(2H, t, J=6Hz), 2.45–2.80(2H, m), 2.92–3.22(2H, m), 3.29–3.58(2H, m), 6.83–6.87(1H, m), 6.92(1H, dd, J=4,5Hz), 7.13(1H, dd, J=2, 5Hz), 7.37–7.58(5H, m) | $C_{19}H_{26}N_2OS$ 70.25 (70.34 | 6.07 6.21 | 8.43 8.63) |

Reference Example 13-5

3,4-Dihydrospiro[naphthalene-2(1H), 2'-piperidin]-1-one Hydrochloride

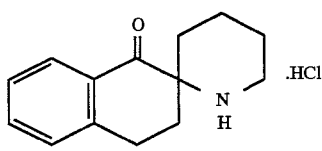

In 250 ml of 1,2-dichloroethane was dissolved 7.64 g of 1-benzoyl-2-(2-phenylethyl)-2-piperidinecarbonitrile. To this solution was added 8.0 g of aluminum chloride and the mixture was refluxed for 6 hours. The reaction mixture was then cooled and poured cautiously into 10% aqueous sodium hydroxide and extracted with methylene chloride and water. The methylene chloride layer was dried over anhydrous sodium sulfate and filtered and the solvent was distilled off. To the group was added 100 ml of methanol and 100 ml of 20% aqueous sodium hydroxide and the mixture was refluxed for 12 hours. After cooling, methanol was distilled off and the group was extracted with methylene chloride and water. The methylene chloride layer was dried over anhydrous sodium sulfate and filtered and the solvent was distilled off. The group was purified by alumina column chromatography using ethyl acetate-hexane (1:2) as the eluent. The active fraction was concentrated under reduced pressure and the group was treated with 6.0 ml of 4N-methanolic hydrochloric acid to give a solid. This solid was recrystallized from methylene chloride to provide 3.0 g of colorless crystals.

m.p. 222°–223° C. $^1$H-NMR (CDCl$_3$, δ): 1.37–1.85(5H, m), 1.92–2.14(3H,m), 2.44(1H,dt,J=7 Hz,5 Hz), 2.76–3.16 (4H,m), 7.20–7.52(3H,m), 8.29(1H,dd,J=8 Hz,1 Hz)

Elemental analysis: $C_{14}H_{18}ClNO \cdot H_2O$. Calcd. C 62.33; H 7.47; N 5.19. Found C 62.39; H 7.27; N 5.42

The following compounds were synthesized in the same manner as Reference Example 13-5.

Reference Example 13-6

3,4-Dihydro-6-methoxyspiro[naphthalene-2(1H),2'-piperidin]-1-one hydrochloride

Reference Example 13-7

3,4-Dihydro-8-methoxyspiro[naphthalene-2(1H),2'-piperidin]-1-one hydrochloride

Reference Example 13-8

3,4-Dihydro-6,7-dimethoxyspiro[naphthalene-2(1H),2-piperidin]-1-one hydrochloride

Reference Example 13-9

6,7-Dihydrospiro[benzo[b]thiophene-5(4H),2'-piperidin]-4-one hydrochloride

The structural formulas, physical properties, and NMR spectra of the above compounds are shown in Table 9.

TABLE 9

| Reference Example | Structural Formula | Melting Point (°C.) | NMR (δppm, CDCl$_3$) | Elemental Analysis [Calcd./(Found)] C | H | N |
|---|---|---|---|---|---|---|
| 13-6 | | 249 (decomposed) | 1.31–1.88(6H, m), 1.89–2.10(1H, m), 2.16(1H, br s), 2.34–2.50(1H, m), 2.74–3.14(4H, m), 3.84(3H, s), 6.66(1H, d, J=3Hz), 6.82(1H, dd, J=9.3Hz), 7.99(1H, d, J=9Hz) | $C_{15}H_{20}ClNO_2$ 64.04 (63.94 | 7.20 7.15 | 5.03 4.97) |
| 13-7 | | 255–259 (decomposed) | 1.42–2.21(6H, m), 2.74–2.85(2H, m), 3.05–3.19(2H, m), 3.36–3.55(1H, m), 3.76–4.00(1H, m), 3.88(3H, s), 6.81(2H, t, J=8Hz), 7.42(1H, t, J=8Hz), 9.06(1H, br s) | $C_{15}H_{20}ClNO_2 \cdot 1/4H_2O$ 63.02 (62.93 | 7.08 7.22 | 4.91 4.89) |
| 13-8 | | 245–248 (decomposed) | 1.33–1.85(5H, m), 1.93–2.10(1H, m), 2.35(1H, br s), 2.42(1H, t, J=5Hz), 2.50(1H, t, J=5Hz), 2.76–3.35(4H, m), 3.92(3H, s), 3.93(3H, s), 6.64(1H, s), 7.50(1H, s) | $C_{16}H_{22}ClNO_3 \cdot 1/4H_2O$ 61.01 (60.75 | 7.10 7.17 | 4.51 4.43) |
| 13-9 | | >280 | 1.34–1.90(7H, m), 2.02–2.18(1H, m), 2.46–2.60(1H, m), 2.75–3.21(4H, m), 7.09(1H, d, J=5Hz), 7.37(1H, d, J=5Hz) | $C_{12}H_{16}ClNOS$ 55.78 (55.91 | 6.26 6.26 | 5.37 5.43) |

Reference Example 13-10

3,4-Dihydrospiro[naphthalene-2(1H),2'-piperidin]-1-ol

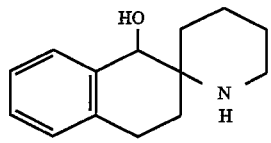

In 20 ml of methanol was dissolved 0.80 g of 3,4-dihydrospiro[naphthalene-2(1H),2'-piperidin]-one and following addition of 0.15 g of sodium borohydride in small portions, the mixture was stirred for 30 minutes. The reaction mixture was then diluted with water and extracted with methylene chloride. The methylene chloride layer was dried over anhydrous sodium sulfate and filtered and the solvent was distilled off. The solid group was recrystallized from methylene chloride-ether to provide 0.25 g of white crystals.

m.p. 125°–127° C. $^1$H-NMR (CDCl$_3$, δ): 1.32–1.98(8H, m), 2.28(1H, quint,J=7 Hz), 2.74–2.94(4H,m), 4.37(1H,s), 7.07–7.28(4H,m), 7.40–7.52(1H,m)

Elemental analysis: $C_{14}H_{19}NO$. Calcd. C 77.38; H 8.81; N 6.45. Found C 77.16; H 8.84; N 7.01.

The following compounds were synthesized in the same manner as Reference Example 13-10.

Reference Example 13-11

3,4-Dihydro-6-methoxyspiro[naphthalene-2(1H),2'-piperidin]-1-ol

Reference Example 13-12

3,4-Dihydro-6,7-dimethoxyspiro[naphthalene-2(1H),2-piperidin]-1-ol hydrochloride

Reference Example 13-13

6,7-Dihydrospiro[benzo[b]thiophene-5(4H),2'-piperidin]-4-ol Hydrochloride

The structural formulas, physical properties, and NMR spectra of the above compounds are shown in Table 10.

TABLE 10

| Reference Example | Structural Formula | Melting Point(°C.) | NMR (δ ppm, CDCl$_3$) | Elemental Analysis [Cald./(Found)] C | H | N |
|---|---|---|---|---|---|---|
| 13-11 | | 132–134 | 1.33–1.87(9H, m), 2.06–2.22(1H, m), 2.72–2.89(4H, m), 3.78(3H, s), 4.31(1H, s), 6.64(1H, d, J=3Hz), 6.67(1H, dd, J=9Hz, 3Hz), 7.33(1H, d, J=9Hz) | $C_{15}H_{21}NO_2$ 72.85 (72.84 | 8.62 8.56 | 5.66 5.66) |
| 13-12 | | 213–216 (decomposed) | 1.36–1.80(8H, m), 2.03–2.24(2H, m), 2.74(2H, t, J=7Hz), 2.80–2.90(2H, m), 3.84(3H, s), 3.86(3H, s), 4.28(1H, s), 6.59(1H, s), 6.95(1H, s) | $C_{16}H_{24}ClNO_3 \cdot 1/5H_2O$ 60.76 (60.54 | 7.69 7.75 | 4.49 4.41) |
| 13-13 | | 215–221 (decomposed) | 1.34–1.90(8H, m), 2.08–2.40(2H, m), 2.75–2.90(4H, m), 4.38(1H, s), 7.00(1H, d), 7.12(1H, d) | $C_{12}H_{18}ClNOS$ 55.15 (55.48 | 6.92 6.98 | 5.34 5.39) |

Reference Example 13-14

3,4-Dihydrospiro[naphthalene-2(1H),2'-piperidine] Hydrochloride

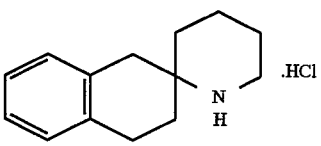

(1) To 200 ml of a solution of 3.36 g of 3,4-dihydrospiro[naphthalene-2(1H),2'-piperidin]-1-one in methylene chloride was added 2.6 g of potassium carbonate. Then, 50 ml of a solution of trifluoroacetic anhydride (3.4 ml) in methylene chloride was added dropwise at 0° C. and the mixture was stirred for 3 hours. This reaction mixture was diluted with water and extracted with methylene chloride. The methylene chloride layer was dried over anhydrous magnesium sulfate and filtered and the solvent was distilled off. The group was purified by silica gel column chromatography using ethyl acetate-hexane (1:2) as the eluent and the active fraction was concentrated under reduced pressure. The solid group was recrystallized from ethyl acetate-hexane to provide 4.86 g of 1'-trifluoroacetyl-3,4-dihydrospiro[naphthalene-2(1H),2'-piperidin]-1-one as colorless needles.

m.p. 97°–100° C. ¹H-NMR (CDCl₃, δ): 1.60–2.25(7H,m), 2.67–3.16(3H,m), 3.35–3.53(1H,m), 3.82–3.98(1H,m), 7.16–7.52(3H,m), 8.20(1H,dd,J=8 Hz,1.2 Hz)

Elemental analysis: $C_{16}H_{16}F_3NO_2$. Calcd. C 61.73; H 5.18; N 4.50. Found C 61.47; H 5.20; N 4.40.

(2) In 30 ml of acetic acid was dissolved 4.44 g of 1'-trifluoroacetyl-3,4-dihydrospiro[naphthalene-2(1H),2'-piperidin]-1-one followed by addition of 0.76 g of 10% palladium-on-carbon, and the catalytic reduction was carried out at 4 kg/cm² and 80° C. This reaction mixture was poured in water, made basic to 10% aqueous solution of sodium hydroxide, and extracted with methylene chloride. The methylene chloride layer was dried over anhydrous sodium sulfate and filtered and the solvent was distilled off. The group was treated with 3.6 ml of 4N-methanolic hydrochloric acid to give a solid. This solid was recrystallized from methylene chloride-ether to provide 2.51 g of white crystals.

m.p. 200°–202° C. ¹H-NMR (CDCl₃, δ): 1.43–1.80(8H, m), 1.84–2.02(1H,m), 2.77(2H,s), 2.84(4H,t,J=5 Hz), 7.10 (4H,s)

Elemental analysis: $C_{14}H_{20}ClN \cdot \frac{1}{4}H_2O$. Calcd. C 69.40; H 8.53; N 5.78. Found C 69.62; H 8.38; N 5.64

Reference Example 13-15

3,4-Dihydro-6-methoxyspiro[naphthalene-2(1H),2'-piperidine] Hydrochloride

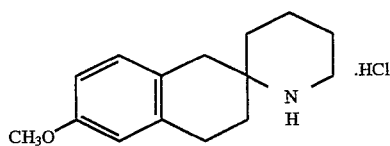

In 30 ml of trifluoroacetic acid was dissolved 6.57 g of 3,4-dihydro-6-methoxyspiro[naphthalene-2(1H),2'-piperidin]-1-one followed by addition of 8.5 ml of triethylsilane and the mixture was stirred for 1 hour. This reaction mixture was poured portionwise in water. To this was added 1N-hydrochloric acid and the mixture was washed with hexane. The aqueous layer was made basic to 1N-aqueous sodium hydroxide and extracted with methylene chloride. The methylene chloride layer was dried over anhydrous sodium sulfate and filtered and the solvent was distilled off. The group was treated with 7.0 ml of 4N-methanolic hydrochloric acid to give a solid. This solid was recrystallized from methanol-ether to provide 5.09 g of white crystals.

m.p. 201°–203° C. ¹H-NMR (CDCl₃, δ): 1.31–2.00(9H, m), 2.71(2H,s),2.74–2.88(4H,m), 3.77(3H,m), 6.62–6.73 (2H,m), 6.98 (1H,m)

Elemental analysis: $C_{15}H_{22}ClNO \cdot \frac{3}{10}H_2O$. Calcd. C 66.60; H 8.31; N 5.18. Found C 66.65; H 8.46; N 5.03

The following compounds were synthesized in the same manner as Reference Example 13-15.

Reference Example 13-16

3,4-Dihydro-6,7-dimethoxyspiro[naphthalene-2(1H),2'-piperidine] hydrochloride

Reference Example 13-17

3,4-Dihydro-8-methoxyspiro[naphthalene-2(1H),2'-piperidine] hydrochloride

Reference Example 13-18

6,7-Dihydrospiro[benzo[b]thiophene-5(4H),2'-piperidine] hydrochloride

The structural formulas, physical properties, and NMR spectra of the above compounds are shown in Table 11.

TABLE 11

| Reference Example | Structural Formula | Melting Point(°C.) | NMR (δ ppm, CDCl₃) | Elemental Analysis [Cald./(Found)] | | |
|---|---|---|---|---|---|---|
| | | | | C | H | N |
| 13-16 | | 205–208 | 1.39–2.00(9H, m), 2.63–2.28(6H, m), 3.83(6H, s), 6.55(1H, s), 6.59(1H, s) | $C_{16}H_{24}ClNO_2$ 64.20 (64.53 | 8.13 8.12 | 4.66 4.70) |
| 13-17 | | 239–241 | 1.40–1.74(8H, m), 1.81–1.98(1H, m), 2.53–2.96(6H, m), 3.81(3H, s), 6.66(1H, d, J=8Hz), 6.73(1H, d, J=8Hz), 7.09(1H, d, J=8Hz) | $C_{16}H_{22}ClNO$ 67.28 (67.28 | 8.15 8.28 | 5.16 5.23) |
| 13-18 | | 212–220 | 1.40–1.85(8H, m), 1.92–2.05(1H, m), 2.52–2.90(6H, m), 6.72(1H, d), 7.08(1H, d) | $C_{12}H_{18}ClNS$ 58.96 (59.12 | 7.09 7.44 | 5.38 5.75) |

Reference Example 14

3,4-Dihydro-6-ethoxyspiro[naphthalene-2(1H),2'-piperidine] Hydrochloride 1) 3,4-Dihydro-6-methoxy-1'-trifluoracetylspiro[naphthalene-2(1H),2'-piperidine]

To a solution of 3,4-dihydro-6-methoxyspiro[naphthalene-2(1H),2'-piperidine] (5.0 g) in dichloromethane (100 ml) was added pyridine (4.5 ml) and trifluoroacetic anhydride (5.2 ml) and the solution was stirred at 0° C. for 1 hour and at ambient temperature for 2 hours. The water was added to the reaction mixture and extracted with dichloromethane. The dichloromethane phase was washed with dilute hydrochloric acid and dried with anhydrous sodium sulfate, filtered, and evaporated. The residue was recrystallized from hexane to give which crystals (5.2 g).

m.p. 75°–76° C.

2) 3,4-Dihydro-6-hydroxy-1'-trifluoracetylspiro[naphthalene-2(1H),2'-piperidine]

To a solution of 3,4-dihydro-6-methoxy-1'-trifluoracetylspiro[naphthalne-2(1H),2'-piperidine] in dichloromethane (60 ml) was added ethanetiol (30 ml) and aluminum chloride (3.3 g) under cooling with ice-water. The reaction mixture was stirred for one hour and poured into ice-water, extracted with dichloromethane, dried and concentrated to give the titled compound.

m.p. 113°–116° C.

3) 3,4-Dihydro-6-ethoxyspiro[naphthalene-2(1H),2'-piperidine] Hydrochloride

To a solution of 3,4-dihydro-6-hydroxy-1'-trifluoracetylspiro[naphthalene-2(1H),2'-piperidine] in DMF (5 ml) and sodium hydride (100 mg) was added ethyl iodide (273 mg) at 60° C. After stirring at 60° C. for 3 hours the reaction mixture was partitioned with ethyl acetate/water and the organic phase was washed with water, dired, and concentrated. The residue was dissolved in a mixture of methanol (50 ml) and 1N aqueous sodium hydroxide (10 ml). The reaction mixture was stirred for 6 hours and concentrated under the reduced pressure. The residue was extracted with ethyl acetate, washed with water, dried, and evaporated. The residue was treated with 4N hydrochloricacid to give the hydrochloride salt (184 mg).

$^1$H-NMR (CDCl$_3$, δ): 1.39(3H,t,J=7 Hz), 1.45–1.96(8H, m), 2.69(2H,s), 2.72–2.9(4H,m), 3.99(2H,q,J=7 Hz), 6.64–6.70(2H,m), 6.96(1H,d,J=8 Hz)

Reference Example 15

3,4-Dihydro-6,7-methylenedioxyspiro[naphthalene-2(1H),2'-piperidine]

3,4-Dihydro-6,7-dimethoxyspiro[naphthalene-2(1H),2'-piperidine] hydrochloride (10 mg) was treated with potassium carbonate (10 g) and benzyl bromide (4 ml) in DMF (300 ml) at 60° C. for 2 hours. The reaction product was extracted with ethyl acetate-water, washed with water, dried, and concentrated. Purification with silica gel column chromatography (eluent; ethyl acetate) gave 3,4-dihydro-6,7-dimethoxy-1'-benzylspiro[naphthalene-2(1H),2'-piperidine] (10.8 g) which was dissolved in hydrobromic acid (33 ml) at 60° C. After being refluxed for 1.5 hr, the reaction mixture was poured into water and neutralized with sodium bicarbonate followed by extraction with ethyl acetate. The extract was washed with water, dried, and concentrated. The residue was crystallized from hexane to give 3,4-dihydro-6,7-hydroxy-1'-benzylspiro[naphthalene-2(1H),2'-piperidine] (5.92 g).

m.p. 122°–124° C.

To a solution of 3,4-dihydro-6,7-hydroxy-1'-benzylspiro[naphthalene-2(1H),2'-piperidine] (390 mg) in DMF (5 ml) was added sodium hydride (144 mg). Dibromo methane (0.85 g) was added at 60° C. and the the reaction mixture was heated at 60° C. for 1 hr. The reaction mixture was poured into water and extracted with ethyl acetate. The organic phase was washed with water, dried and concentrated under the reduced pressure. Purification with silica gel chromatography gave 3,4-dihydro-6,7-dihydro-6,7-hydroxy-1'-benzylspiro[naphthalene-2(1H),2'-piperidine].

$^1$H-NMR (CDCl$_3$, δ): 1.37–1.65(6H,m), 1.70–1.86(1H, m), 1.88–2.07(1H,m), 2.47–2.96(6H,m), 3.47–3.73(2H,m), 5.87(2H,m), 6.56(1H,m), 6.57(1H,m), 7.14–7.40(5H,m)

The suspension of 3,4-dihydro-6,7-hydroxy-1'-benzylspiro[naphthalene-2(1H),2'-piperidine] (164 mg) and 10% Pd-carbon (150 mg) in ethanol (10 ml) and conc. hydrochloric acid (0.3 ml) was hydrogenated under atmospheric pressure at ambient temperature for 18 hr. The catalysis was filtered off and the filtrate was concentrated. The residue was neutralized with sodium bicarbonate and extracted with ethyl acetate, The organic phase was washed with water, dried, and concentrated to give the product (90 mg).

$^1$H-NMR (CDCl$_3$, δ): 1.42–1.98(9H,m), 2.64–2.87(6H, m), 5.87(2H,s), 6.53(1H,s), 6.57(1H,s)

Reference Example 16

3,4-Dihydro-6,7-diethoxyspiro[naphthalene-2(1H),2'-piperidine] Hydrochloride To a solution of 3,4-dihydro-6,7-dihydroxy-1'-benzylspiro[naphthalene-2(1H),2'-piperidine] (970 mg) in DMF (10 ml) was added sodium hydride (691 mg) followed by ethyliodide (0.48 ml). After stirring for 3 hours at ambient temperature, the reaction mixture was poured into water and extracted with ethyl acetate. The extract was washed with water, dried, and evaporated under the reduced pressure. The residue was purified by silica gel column chromatography (eluent; ethyl acetate) to give an oil which was subjected to a catalytic hydrogenation reaction to give the titled compound as a hydrochloride salt.

Elemental analysis: $C_{18}H_{28}ClNO_2$. Calcd. C 66.34; H 8.66; N 4.30. Found C 66.22; H 9.15; N 4.03

Reference Example 17

3,4-Dihydro-6-methoxy-7-nitrospiro[naphthalene-2(1H),2'-piperidine] Hydrochloride

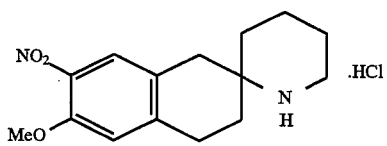

(1) 6.0 g of 1'-trifluoroacetyl-3,4-dihydro-6-methoxyspiro[naphthalene-2(1H),2'-piperidine] was dissolved in 150 ml of chloroform. After 1.5 g of ammonium nitrate was suspended in this solution, 9 ml of trifluoroacetic anhydride was added, followed by overnight stirring at room temperature. After water was added, the reaction mixture was extracted with methylene chloride. The extract was dried over anhydrous sodium sulfate and filtered, after which the solvent was distilled off. The residue was purified by silica gel column chromatography to yield 1.4 g of 1'-trifluoroacetyl-3,4-dihydro-6-methoxy-7-nitrospiro[naphthalene-2(1H),2'-piperidine] and 0.457 g of 1'-trifluoroacetyl-3,4-dihydro-6-methoxy-5-nitrospiro[naphthalene-2(1H),2'-piperidine].

1'-Trifluoroacetyl-3,4-dihydro-6-methoxy-7-nitrospiro [naphthalene-2(1H),2'-piperidine]

m.p. 105°–107° C.

1'-Trifluoroacetyl-3,4-dihydro-6-methoxy-5-nitrospiro [naphthalene-2(1H),2'-piperidine]

m.p. 128°–130° C.

(2) 0.5 g of 1'-trifluoroacetyl-3,4-dihydro-6-methoxy-7-nitrospiro[naphthalene-2(1H),2'-piperidine] as obtained in term (2) above was dissolved in 50 ml of methanol. To this solution, 0.221 g of potassium carbonate and 5 ml of water were added, followed by stirring at room temperature for 15 hours. After reaction mixture extraction with ethyl acetate, the extract was dried over anhydrous sodium sulfate and filtered, after which the solvent was distilled off. The residue was treated with a 4N hydrochloric acid-ethyl acetate solution to yield 3,4-dihydro-6-methoxy-7-nitrospiro [naphthalene-2(1H),2'-piperidine]hydrochloride as a noncrystalline powder.

$^1$H-NMR (CDCl$_3$, δ): 1.45–2.00(8H,m), 2.73(2H,s), 2.80–2.95(4H,m), 3.91(3H,s), 6.81(1H,s), 7.63(1H,s)

Reference Example 18

3,4-Dihydro-6-methoxy-5-nitrospiro[naphthalene-2 (1H),2'-piperidine] Hydrochloride

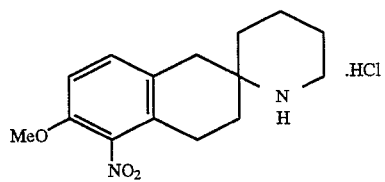

1'-Trifluoroacetyl-3,4-dihydro-6-methoxy-5-nitrospiro [naphthalene-2(1H),2'-piperidine] as obtained in Reference Example 17 was treated in the same manner to yield the title compound as a noncrystalline powder.

$^1$H-NMR (free base, CDCl$_3$, δ): 1.44–1.75(7H,m), 1.89–1.96(1H,m), 2.71–2.84(6H,m), 3.85(3H,s), 6.83(1H,d, J=9 Hz), 7.13(1H,d,J=9 Hz)

Reference Example 19

7-Acetyl-3,4-dihydro-6-methoxyspiro[naphthalene-2 (1H),2'-piperidine]

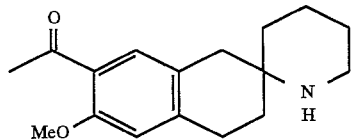

(1) 2.94 g of 1'-trifluoroacetyl-3,4-dihydro-6-methoxyspiro[naphthalene-2(1H),2'-piperidine] as obtained in Example 22-(1) was dissolved in 30 ml of carbon disulfide. To this solution, 0.85 ml of acetic anhydride was added under ice cooling conditions. After 2.4 g of aluminum chloride was added, the mixture was stirred at room temperature overnight. The reaction mixture was then added to ice water and extract with ethyl acetate. The extracted was dried over anhydrous sodium sulfate and filtered, after which the solvent was distilled off. The residue was purified by silica gel column chromatography to yield a crude crystal, which was then recrystallized from ethyl acetate-hexane to yield 0.21 g of 7-acetyl-1'-trifluoroacetyl-3,4-dihydro-6-methoxyspiro[naphthalene-2(1H),2'-piperidine].

m.p. 156°–157° C.

Reference Example 20-1

2-Chloroacetylamino-2-hydroxymethyltetralin

To a suspension of 2-aminotetralin-2-carboxylic acid (500 mg, 2.6 mmol) in THF (10 ml), lithium aluminum hydride (250 mg, 6.5 mmol) was added, while the suspension was stirred at room temperature, followed by further stirring at constant temperature for 2 hours. To this mixture, a 1N aqueous sodium hydroxide solution was added. After the precipitate was filtered out, the mother liquor was washed with saturated saline and dried over anhydrous sodium sulfate. The solvent was distilled off under reduced pressure to yield an almost pure aminoalcohol (420 mg, 85%) as a colorless syrup. The alcohol (420 mg, 2.2 mmol) was then dissolved in an ethyl acetate (10 ml)-saturated sodium carbonate solution (10 ml). To this solution, chloroacetyl chloride (340 mg, 3 mmol) was added drop by drop, while the solution was vigorously stirred under ice cooling conditions. Five minutes later, the organic layer was separated, washed with saturated saline and dried over anhydrous sodium sulfate. After the solvent was distilled off under reduced pressure, the residue was subjected to silica gel column chromatography for elution with hexane-ethyl acetate (1:1) to yield 400 mg (72%) of the title compound.

Reference Example 20-2

2-(Chloroacetyl)amino-2-hydroxymethyl-6-methoxytetralin was synthesized in the same manner as in Reference Example 20-1.

Reference Example 20-3

2-(Chloroacetyl)amino-2-hydroxymethyl-7-methoxytetralin was synthesized in the same manner as in Reference Example 20-1.

Reference Example 20-4

2-(Chloroacetyl)amino-6,7-dimethoxy-2-(hydroxymethyl)tetralin was synthesized in the same manner as in Reference Example 20-1.

Table 12 shows the structural formulas, physical properties and $^1$H-NMR spectra of these compounds.

TABLE 12

| Reference Example | Structural Formula | Melting Point(°C.) | ¹H-NMR (ppm, CDCl₃) |
|---|---|---|---|
| 20-1 | 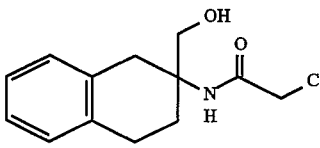 | oil | 1.97(1H, ddd, J=13.0, 8.8, 7.0Hz), 2.26(1H, ddd, J=13.0, 7.9, 5.8Hz), 2.73–3.09(4H, m), 3.81(2H, s), 3.98(2H, s), 4.04–4.45(1H, br), 6.60(1H, br s), 7.05–7.19(4H, m) |
| 20-2 | 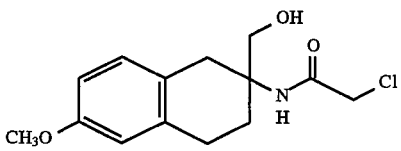 | oil | 1.95(1H, m), 2.26(1H, m), 2.70–3.00(4H, m), 3.78(3H, s), 3.80(2H, s), 3.98(2H, s), 6.60(1H, br s), 6.64–6.75(2H, m), 7.00(1H, d, J=8.4Hz) |
| 20-3 | 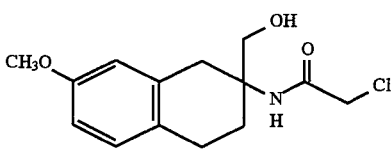 | oil | 1.92(1H, m), 2.25(1H, m), 2.65–3.08(4H, m), 3.76(3H, s), 3.79(2H, d, J=4.6Hz), 3.97(2H, s), 4.23(1H, br s), 6.60 (1H, s), 6.61(1H, s), 6.73(1H, dd, J=8.4, 2.6Hz), 7.03(1H, ) d, J=8.4Hz) |
| 20-4 | 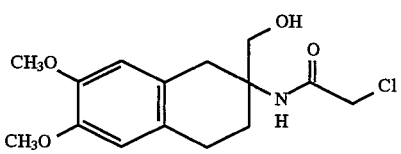 | 210–212 | 1.62(1H, m), 2.30(1H, m), 2.55–2.98(4H, m), 3.58(2H, br s), 3.70(6H, s), 3.97(2H, q, J=17.6, 12.4Hz), 4.82(1H, brt, J=6Hz), 6.60, 6.64(1H, each, s), 7.59(1H, br s) (DMSO-d₆) |

Reference Example 21-1

Spiro[tetralin-2,3'-morpholine-5'-one]

To a suspension of sodium hydride (120 mg, 5 mmol, 60% oil, washed with hexane) in DMF (3 ml), a solution of 2-chloroacetylamino-2-hydroxymethyltetralin (400 mg, 1.6 mmol) in DMF (3 ml) was added drop by drop, while the suspension was stirred under ice cooling conditions. After cooling to room temperature, the mixture was stirred for 3 hours at constant temperature. After a large amount of water was added, the mixture was extracted with ethyl acetate. The organic layer was washed with water several times, washed with saturated saline and dried over anhydrous sodium sulfate. After the solvent was distilled off under reduced pressure, the residue was subjected to silica gel column chromatography for elution with hexane-ethyl acetate (1:1–1:2) to yield 150 mg (43%) of the title compound as a white crystal.

Reference Example 21-2

6-Methoxyspiro[tetralin-2,3'-morpholine]-5'-one

To a solution of 2-chloroacetylamino-2-hydroxy-6-methoxytetralin (450 mg, 1.6 mmol) in THF (15 ml), 60% oily sodium hydride (200 mg, 5.0 mmol) was added, while the solution was stirred under ice cooling conditions. After cooling to room temperature, the mixture was stirred for 3 hours at constant temperature. After a saturated aqueous solution of ammonium chloride was added, the mixture was extracted with ethyl acetate. The organic layer was washed with saturated saline and dried over anhydrous sodium sulfate. The solvent was distilled off under reduced pressure to yield about 400 mg (almost 100%) of the title compound as a crude crystal, a portion of which was then recrystallized from chloroform-isopropyl ether.

Reference Example 21-3

7-Methoxyspiro[tetraline-2,3'-morpholine]-5'-one was synthesized in the same manner as in Reference Example 21-2.

Reference Example 21-4

6,7-Dimethoxyspiro[tetralin-2,3'-morpholine]-5'-one was synthesized in the same manner as in Reference Example 21-2.

Table 13 shows the structural formulas, physical properties and ¹H-NMR spectra of these compounds.

TABLE 13

| Reference Example | Structural Formula | Melting Point(°C.) | $^1$H-NMR (ppm, CDCl$_3$) |
|---|---|---|---|
| 21-1 | ![structure] | 164–166 | 1.80–2.15(2H, m), 2.73–3.07(4H, m), 3.69(2H, s), 4.20(2H, s), 6.32(1H, br s), 7.03–7.20(4H, m) |
| 21-2 | ![structure with CH$_3$O] | 173–174 | 1.78–2.15(2H, m), 2.65–2.95(4H, m), 3.68(2H, s), 3.78(3H, s), 4.20(2H, s), 6.10(1H, br s), 6.63–6.76(2H, m), 6.98 (1H, d, J=8.4Hz) |
| 21-3 | ![structure with CH$_3$O] | 144–148 | 1.78–2.15(2H, m), 2.69–3.01(4H, m), 3.69(2H, s), 3.78(3H, s), 4.21(2H, s), 6.00(1H, br s), 6.59(1H, d, J=2.8Hz), 6.76 (1H, dd, J=8.4, 7.8Hz), 7.05(1H, d, J=8.4Hz) |
| 21-4 | ![structure with CH$_3$O, CH$_3$O] | 202–204 | 1.75–1.95(1H, m), 1.96–2.15(1H, m), 2.65–2.95(4H, m), 3.69(2H, s), 3.84, 3.86(3H, each, s), 4.21(2H, s), 6.03 (1H, br s), 6.57, 6.01(1H, each, s) |

Reference Example 22-1

Spiro[tetralin-2,3'-morpholine] Hydrochloride

To a solution of spiro[tetralin-2,3'-morpholine]-5'-one (22 mg, 0.1 mmol) in THF (2 ml), lithium aluminum hydride (12 mg, 0.3 mmol) was added, while the solution was stirred under ice cooling conditions. After cooling to room temperature, the mixture was stirred for 1 hour at constant temperature. After further stirring at 60° C. for 3 hours, a 1N aqueous sodium hydroxide solution was added; the precipitate was filtered out. The mother liquor was washed with saturated saline and dried over anhydrous sodium sulfate. The solvent was distilled off under reduced pressure. The obtained residue was subjected to silica gel column chromatography for elution with ethyl acetate-methanol (1:0–9:1). After concentration, the organic layer was dissolved in water-chloroform; the chloroform layer was dried and concentrated under reduced pressure. The obtained residue was dissolved in ethyl acetate. To this solution, a 4N hydrogen chloride-ethyl acetate solution was added. The mixture was concentrated under reduced pressure and crystallized with isopropyl ether to yield 12 mg (49%) of the title compound.

Reference Example 22-2

6-Methoxyspiro[tetralin-2,3'-morpholine]hydrochloride was synthesized in the same manner as in Reference Example 22-1.

Reference Example 22-3

7-Methoxyspiro[tetralin-2,3'-morpholine]hydrochloride was synthesized in the same manner as in Reference Example 22-1.

Reference Example 22-4

6,7-Dimethoxyspiro[tetralin-2,3'-morpholine] hydrochloride was synthesized in the same manner as in Reference Example 22-1.

Table 14 and 15 show the structural formulae, physical properties and $^1$H-NMR spectra of these compounds.

TABLE 14

| Reference Example | Structural Formula | Melting Point(°C.) | $^1$H-NMR (ppm, CDCl$_3$) |
|---|---|---|---|
| 22-1 |  | 164–166 | 1.70–1.90(2H, m), 1.91–2.05(1H, m), 2.70–2.93(4H, m), 2.94(2H, t, J=4.4Hz), 3.52(2H, s), 3.71(2H, t, J=4.8Hz), 7.00–7.12(4H, m) |

TABLE 14-continued

| Reference Example | Structural Formula | Melting Point(°C.) | ¹H-NMR (ppm, CDCl₃) |
|---|---|---|---|
| 22-2 | [structure: CH₃O-naphthalene-tetrahydro-spiro-morpholine · HCl] | 212–215 | 1.68–1.85(1H, m), 1.86–2.03(2H, m), 2.65–2.90(4H, m), 2.93(2H, t, J=4.6Hz), 3.51(2H, s), 3.71(2H, t, J=4.8Hz), 3.77(3H, s), 6.63–6.74(2H, m), 7.01(1H, d, J=8.4Hz) |

TABLE 15

| Reference Example | Structual Formula | Melting Point (°C.) | ¹H—NMR (ppm, CDCl₃) |
|---|---|---|---|
| 22-3 | [structure: CH₃O-naphthalene-tetrahydro-spiro-morpholine · HCl] | 230–235 | 1.65–2.04(3H, m), 2.65–2.87(4H, m), 2.93(2H, t, J=5, 6Hz), 3.51(2H, s), 3.70(2H, t, J=5.4Hz), 3.77(3H, s), 6.63(1H, d, J=2.6Hz), 6.72(1H, dd, J=8.2, 2.8Hz), 7.03(1H, d, J=8.2Hz) |
| 22-4 | [structure: CH₃O, CH₃O-naphthalene-tetrahydro-spiro-morpholine · HCl] | 212–215 | 1.68–1.84(1H, m), 1.85–2.07(2H, m), 2.63–2.90(4H, m), 2.95(2H, t, J=4.8Hz), 3.52(2H, s), 3.72(2H, t, J=5.2Hz), 3.84(6H, s), 6.56, 6.62(1H, each, s) |

Reference Example 23

3,4-Dihydro-6,7-dimethoxy-4'-methylspiro [naphthalene-2(1H),2'-piperazine] Dihydrochloride (1) Ethyl 2-[(N-benzyloxycarbonyl-N-methylamino) acetylamino]-1,2,3,4-tetrahydro-6,7-dimethoxynaphthalene-2-carboxylate To a solution of ethyl 2-amino-1,2,3,4-tetrahydro-6,7-dimethoxynaphthalene-2-carboxylate (430 mg, 1.5 mmol), N-benzyloxycarbonylsarcosine (357 mg, 1.6 mmol), and 1-ethyl-3-(3'-dimethylaminopropyl)carbodiimide hydrochloride in dichloromethane (5 ml) was added triethylamine (160 mg, 1.6 mmol) under stirring at 0° C. After stirring for 2 hr, the reaction mixture was concentrated in vacuo and the residue was dissolved in ethyl acetate. The solution was washed with 1N hydrochloric acid, sat. sodium bicarbonate, sat. sodium chloride, dried, and evaporated. The residue was purified with silica gel column chromatography [eluent; hexane-ethyl acetate (1:1 to 1:2)] to give the titled compound (550 mg, 74%).

¹H-NMR (CDCl₃, δ): 1.25(3H,t), 2.05–2.17(1H,m), 2.38–3.00(7H,m), 3.22(1H,d), 3.75–3.90(8H,m), 4.20(2H, q), 5.02(2H,s), 6.37–6.60(3H,m), 7.20–7.39(5H,m)

(2) 3,4-Dihydro-6,7-dimethoxy-4'-methylspiro [naphthalene-2(1H),2'-piperidine]-3',6'-dione A solution of ethyl 2-[(N-benzyloxycarbonyl-N-methylamino)acetylamino]-1,2,3,4-tetrahydro-6,7-dimethoxynaphthalene-2-carboxylate (550 mg, 1.1 mmol) in ethanol (20 ml) was hydrogenated in the presence of 10% Pd-carbon (250 mg) for 6 hr. The catalyst was filtered off and the filtrate was concentrated in vacuo. The residue was dissolved in 1N sodium hydroxide (2 ml) and THF (10 ml) and heated at 80° C. for 17 hr. The reaction mixture was concentrated in vacuo and the residue was dissolved in ethyl acetate. The solution was washed with water, and sat. sodium chloride, dried, and concentrated in vacuo. The residue was recrystallized from chloroform-isopropylether to give the titled compound (150 mg).

m.p. 168°–169° C.

(3) 3,4-Dihydro-6,7-dimethoxy-4'-methylspiro [naphthalene-2(1H),2'-piperazine]

To a suspension of lithium aluminum hydride (114 mg, 3 mmol) and aluminum chloride (400 mg, 3 mmol) in ether (4 ml) was added the suspension of 3,4-dihydro-6,7-dimethoxy-4'-methylspiro[naphthalene-2(1H),2'-piperazine]-3',6'-dione (50 mg, 0.16 mmol) in ether (2 ml). The reaction mixture was stirred at ambient temperature for 45 min and treated with 1N sodium hydroxide. The precipitate was filtered and washed with 1N sodium hydroxide and chloroform. The filtrate was washed with sat. sodium chloride, dried, and concentrated to give the titled compound (42 mg, 86%). A portion was dissolved in ethyl acetate and treated with 4N hydrochloric acid in ethyl acetate. Concentration under reduced pressure followed by addition of isopropylether gave a powder.

¹H-NMR (CDCl₃, δ): 1.90–2.05(1H,m), 2.18–2.35(1H, m), 2.69(1H,dd), 2.80–2.94(2H,m), 3.06(3H,s), 3.58(1H,d), 3.85,3.86(3H,each s), 4.04(2H,ABq), 6.11(1H,br s), 6.53, 6.61(1H,each s)

Reference Example 24

(R)-(+)-3,4-Dihydro-6-methoxyspiro[naphthalene-2 (1H),2'-piperidine] Hydrochloride

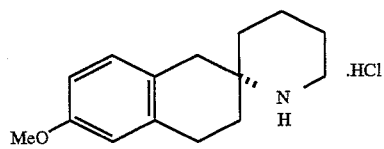

After conversion into a free base, 1 g of 3,4-dihydro-6-methoxy-spiro[naphthalene-2(1H),2'-piperidine] hydrochloride was dissolved in methanol. To this solution, a methanol solution of 0.867 g of (S)-(+)-10-camphorsulfonic acid was added, followed by concentration under reduced pressure. After the residue was dissolved in 10 ml of methanol, 20 ml of isopropyl ether was added; the mixture was kept standing at room temperature for 5 hours. The resulting crystal was collected by filtration and twice recrystallized from methanol-isopropyl ether to yield 0.2 g of a crystal. After conversion into a free base, this crystal was treated with a 4N-hydrochloric acid-ethyl acetate solution to yield 0.1 g of (R)-(+)-3,4-dihydro-6-methoxyspiro[naphthalene-2(1H),2'-piperidine] hydrochloride as a white crystal. Optical purity was determined by high performance liquid chromatography using an optical isomer separation column (CHIRALCEL OB-H, produced by Daicel Chemical Industries, Ltd.).

Optical purity: Over 99.7% ee. Melting point: 152°–155° C. Optical rotation: $[\alpha]_D^{27}=+3.44$

Reference Example 25

(S)-(−)-3,4-Dihydro-6-methoxyspiro[naphthalene-2 (1H),2'-piperidine] Hydrochloride

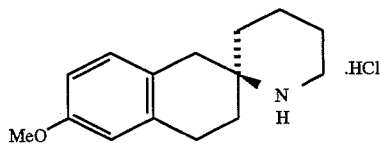

The mother liquors for recrystallization of the (+)-configuration in Reference Example 24 were combined and concentrated under reduced pressure. After conversion into a free base, the residue was dissolved in methanol. To this solution, a methanol solution of 0.7 g of (R)-(−)-10-camphorsulfonic acid was added, followed by concentration under reduced pressure. The residue was treated in the same manner as in Example 25 to yield 0.09 g of (S)-(−)-3,4-dihydro-6-methoxyspiro[naphthalene-2(1H),2'-piperidine] hydrochloride as a white crystal.

Optical purity: 97.1% ee. Melting point: 155°–160° C.

Reference Example 26

(+)-3,4-Dihydro-6,7-dimethoxyspiro[naphthalene-2 (1H),2'-piperidine]-1-one Hydrochloride

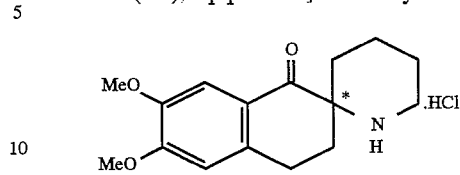

After conversion into a free base, 10 g of 3,4-dihydro-6,7-dimethoxyspiro[naphthalene-2(1H),2'-piperidine]-1-one hydrochloride was dissolved in 700 ml of methanol. To this solution, 12.07 g of (2S,3S)-(+)-0,0'-dibenzoyltartaric acid monohydride was added. After the mixture was kept standing at room temperature for 3 days, the resulting crystal was collected by filtration. After conversion into a free base, this crystal was treated with a 4N-hydrochloric acid-ethyl acetate solution to yield 1.84 g of (+)-3,4-dihydro-6,7-dimethoxyspiro[naphthalene-2(1H),2'-piperidine]-1-one hydrochloride as a white crystal.

Optical purity: Over 99.9% ee. Melting point: 251°–254° C. Optical rotation: $[\alpha]_D^{26}=+41.22$

Reference Example 27

(−)-3,4-Dihydro-6,7-dimethoxyspiro[naphthalene-2 (1H),2'-piperidine]-1-one Hydrochloride The mother liquors for recrystallization of the (+)-configuration in Reference Example 26 were combined and concentrated under reduced pressure. After conversion into a free base, the residue was dissolved in methanol. Using (2R,3R)-(−)-0,0'-dibenzoyltartaric acid monohydride, the solution was treated in the same manner as in Example 27 to yield 2.04 g of (−)-3,4-dihydro-6,7-dimethoxyspiro [naphthalene-2(1H),2'-piperidine]-1-one hydrochloride as a white crystal.

Optical purity: Over 99.9% ee. Melting point: 250°–252° C. Optical rotation: $[\alpha]_D^{26}=-41.41$

Reference Example 28

(−)-3,4-Dihydro-6,7-dimethoxyspiro[naphthalene-2 (1H),2'-piperidine] Hydrochloride (+)-3,4-dihydro-6,7-dimethoxyspiro[naphthalene-2(1H), 2'-piperidine]-1-one hydrochloride as obtained in Example 27 was treated in the sammer as in Reference Example 13-10.

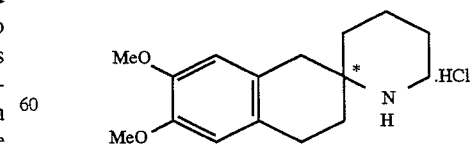

to yield (−)-3,4-dihydro-6,7-dimethoxyspiro[naphthalene-2 (1H),2'-piperidine] hydrochloride.

Melting point: 165°–167° C. Optical rotation: $[\alpha]_D^{26}=-1.92$

Reference Example 29

(+)-3,4-Dihydro-6,7-dimethoxyspiro[naphthalene-2 (1H),2'-piperidine] Hydrochloride Melting point: 165°–167° C. Optical rotation: $[\alpha]_D^{26}$=+ 1.80

Reference Example 30

1-Benzoylhexahydro-2-(2-phenylethyl)-1H-azepine-2-carbonitrile was obtained by the same procedure as Reference Example 13-1.

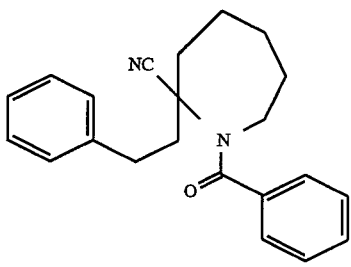

Melting point: 116°–118° C. $^1$H-NMR (CDCl$_3$, δ): 1.25–1.76(3H,m), 1.80–3.23(10H,m), 3.51–3.67(1H,m), 7.08–7.50(10H,m).

Reference Example 31

1,3,4,5,6,7,3',4'-Octahydrospiro[2H-azepine-2,2'(1H)-naphthalene]-1'-one hydrochloride was obtained by the same procedure as Reference Example 13-5.

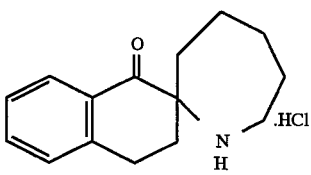

Melting point: 208°–210° C. $^1$-NMR (CDCl$_3$, δ): 1.20–1.84(7H,m), 1.87–2.30(4H,m), 2.55–2.71(1H,m), 2.93–3.08(3H,m), 7.21(1H,d,J=8 Hz), 7.32(1H,d,J=8 Hz), 7.46(1H,dt,J=8.2 Hz), 8.05(1H,dd,J=8.2 Hz).

Reference Example 32

1,3,4,5,6,7,1',2',3',4'-Decahydrospiro[2H-azepine-2,2'(1H)-naphthalene]hydrochloride was obtained by the same procedure as Reference Example 13-10 or 13-14.

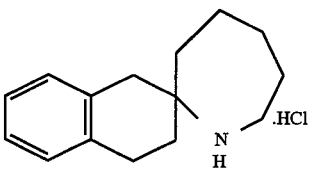

Melting point: 191°–194° C. $^1$H-NMR (CDCl$_3$, δ): 1.08–1.92(11H,m), 2.60–2.98(6H,m), 7.01–7.13(4H,m).

WORKING EXAMPLES

Example I-1

1-(5-Amino-4,4-diphenylpentyl)-4-phenylpiperidine

To a solution of 1-(5-formylamino-4,4-diphenylpentyl)-4-phenylpiperidine (2.07 g) in methanol (50 ml) was added 1N-sodium hydroxide (30 ml) and the mixture was refluxed overnight. This reaction mixture was concentrated to dryness and the group was extracted using methylene chloride and water. The organic layer was washed with water, dried over anhydrous sodium sulfate, and concentrated to dryness to provide the title compound (1.94 g) as yellow powder.

The compounds of Examples I-2 through I-4 were synthesized in the same manner as Example I-1.

Example I-2

3,4-Dihydro-6-methoxy-1'-(5-amino-4,4-diphenylpentyl)spiro[naphthalene-2(1H),2'-piperidine]

Example I-3

1-[5-Amino-4-(4-methoxyphenyl)-4-phenylpentyl]-4-phenylpiperidine

Example I-4

1-[5-Amino-4,4-bis(4-chlorophenyl)pentyl]-4-(4-fluorophenyl)piperadine

Example I-5

3,4-Dihydro-6-methoxy-1'-(6-amino-4,4-diphenylhexyl)spiro[naphthalene-2(1H),2'-piperidine]

To a solution of 3,4-dihydro-6-methoxy-1'-(5-cyano-4,4-diphenylpentyl)spiro[naphthalene-2(1H),2'-piperidine] (0.6 g) in tetrahydrofuran (15 ml) was added lithium aluminum hydride (95 mg) portionwise under ice-cooling and stirring. After completion of dropwise addition, the mixture was heated at 60° C. for 6 hours. To this reaction mixture were serially added water (0.25 ml), 15% sodium hydroxide solution (0.75 ml) and water (0.25 ml) under ice-cooling and stirring and the precipitate which separated out was filtered off. The filtrate was washed with saturated aqueous solution of sodium chloride, dried over anhydrous sodium sulfate, and concentrated to dryness to provide the title compound (0.54 g) as light-yellow syrup.

The compound of Example I-6 was synthesized in the same manner as Example I-5.

Example I-6

3,4-Dihydro-6,7-dimethoxy-1'-(7-amino-4,4-diphenylheptyl)spiro[naphthalene-2(1H),2'-piperidine]

The structural formulae, physical properties, and NMR spectra of the above compounds are shown in Table 16.

TABLE 16

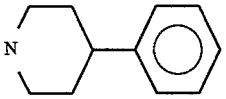

| Example | X | Y | R₁ | m | n | Melting Point (°C.) | $^1$H—NMR ($\delta_{ppm}$, CDCl$_3$) |
|---|---|---|---|---|---|---|---|
| I-1 | H | H | 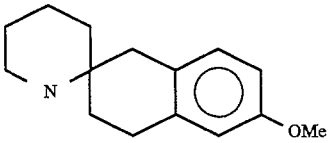 | 1 | 3 | syrup | 1.20–1.35(2H, m), 1.65–2.00(8H, m), 2.10–2.20 (2H, m), 2.30(2H, t), 2.35–2.50(1H, m), 2.90 (2H, d), 3.35(2H, s), 7.10–7.35(15H, m) |
| I-2 | H | H | 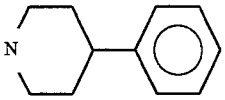 | 1 | 3 | syrup | 1.05–2.80(22H, m), 3.30(2H, s), 3.76(3H, s), 6.60–6.72(2H, m), 6.96(1H, d), 7.13–7.35 (10H, m) |
| I-3 | 4-MeO | H | 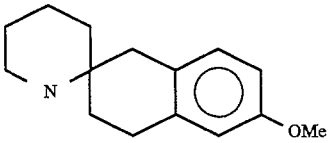 | 1 | 3 | syrup | |
| I-4 | 4-Cl | 4-Cl | 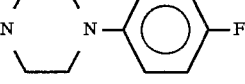 | 1 | 3 | syrup | 1.10–1.30(2H, m), 2.02–2.22(2H, m), 2.37(2H, t), 2.50(4H, t), 3.09(4H, t), 6.80–7.30(12H, m) |
| I-5 | H | H | 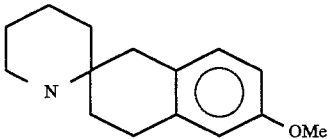 | 2 | 3 | syrup | 1.05–1.25(2H, m), 1.38–2.80(22H, m), 3.76(3H, s), 6.61–6.71(2H, m), 6.95(1H, d), 7.10–7.30 (10H, m) |
| I-6 | H | H | 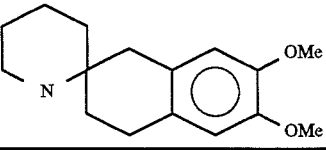 | 3 | 3 | syrup | 1.03–1.21(4H, m), 1.30–2.80(22H, m), 3.82, 3.83 (3H each, s), 6.55, 6.57(1H each, s), 7.10–7.30 (10H, m) |

Example II-1

1-(N,N-Dimethylamino)-4,4-diphenyl-5-(formylamino)pentane

A mixture of 5-formylamino-1-iodo-4,4-diphenylpentane (8.5 g), dimethylamine hydrochloride (17.63 g), triethylamine (30.1 ml), and potassium carbonate (3 g) was heated in acetonitrile (250 ml) at 60° C. for 2 hours. This reaction mixture was concentrated to dryness and the group was extracted using ethyl acetate and water. The organic layer was washed with saturated aqueous solution of sodium chloride, dried over anhydrous sodium sulfate, and concentrated to dryness. The group was crystallized from ethyl acetate-isopropyl ether to provide the title compound (4.5 g) as white powder.

The compounds of Examples II-2 through II-10, II-12 through II-16, II-25 through II-29, II-31, II-34 through II-36, and II-40 through II-68 were respectively synthesized in the same manner as Example II-1.

Example II-2

1-(N-Benzyl-N-methylamino)-4,4-diphenyl-5-(formylamino)pentane hydrochloride

Example II-3

4,4-Diphenyl-5-formylamino-1-(morpholino)pentane hydrochloride

Example II-4

4,4-Diphenyl-5-formylamino-1-(2,3,4,5-tetrahydro-1H-3-benzazepin-3-yl)pentane hydrochloride Example II-5

4,4-Diphenyl-5-formylamino-1-(4-phenylpiperidino)pentane hydrochloride

Example II-6

1-[4-(4-Fluorophenyl)piperazin-1-yl]-5-formylamino-4,4-diphenylpentane dihydrochloride

Example II-7

3,4-Dihydro-6-methoxy-1'-(5-formylamino-4,4-diphenylpentyl)spiro[naphthalene-2 (1H),2'-piperidine] dihydrochloride

Example II-8

1-Benzylamino-4,4-diphenyl-5-(tosylamino)pentane hydrochloride

Example II-9

1-(N-Benzyl-N-methylamino)-4,4-diphenyl-5-(tosylamino)pentane hydrochloride

Example II-10

4,4-Diphenyl-1-(3-nitrobenzylamino)-5-(tosylamino)pentane hydrochloride

Example II-12

4,4-Diphenyl-1-[3-(methoxycarbonyl)benzylamino]-5-(tosylamino)pentane hydrochloride

Example II-13

4,4-Diphenyl-1-(2-picolylamino)-5-(tosylamino)pentane dihydrochloride

Example II-14

4,4-Diphenyl-1-(1-hexamethyleneimino)-5-(tosylamino)pentane hydrochloride

Example II-15

4,4-Diphenyl-1-(4-phenylpiperazin-1-yl)-5-(tosylamino)pentane

Example II-16

4,4-Diphenyl-1-[4-(2-methoxyphenyl)piperazin-1-yl]-5-(tosylamino)pentane hydrochloride

Example II-25

4-(4-Chlorophenyl)-5-formylamino-4-phenyl-1-(4-phenylpiperidino)pentane hydrochloride

Example II-26

4-(4-Chlorophenyl)-5-formylamino-4-phenyl-1-(4-phenylpiperazin-1-yl)pentane dihydrochloride

Example II-27

4-(4-Chlorophenyl)-1-[4-(4-fluorophenyl)piperazin-1-yl]-5-formylamino-4-phenylpentane dihydrochloride

Example II-28

4-(4-Chlorophenyl)-1-[4-(diphenylmethyl)piperazin-1-yl]-5-formylamino-4-phenylpentane

Example II-29

5-Formylamino-4-(4-methoxyphenyl)-4-phenyl-1-(4-phenylpiperidino)pentane hydrochloride

Example II-31

4,4-Bis(4-chlorophenyl)-1-[4-(4-fluorophenyl)piperazin-1-yl]-5-(formylamino)pentane dihydrochloride

Example II-34

1-[4-(4-Fluorophenyl)piperazin-1-yl]-6-formylamino-5,5-diphenylhexane dihydrochloride

Example II-35

1-[4-(4-Fluorophenyl)piperazin-1-yl]-6-formylamino-4,4-diphenylhexane dihydrochloride

Example II-36

4,4-Diphenyl-1-(4-phenylpiperidino)-6-(tosylamino)hexane hydrochloride

Example II-40

7-Acetylamino-4,4-diphenyl-1-[3-(methoxycarbonyl)benzylamino]heptane dihydrochloride

Example II-41

7-Acetylamino-4,4-diphenyl-1-(β-phenethylamino)heptane dihydrochloride

Example II-42

7-Acetylamino-1-[2-(6,7-dimethoxy-1,2,3,4-tetrahydronaphthylamino)]-4,4-diphenylheptane dihydrochloride

Example II-43

7-Acetylamino-1-{N-benzyl-N-[2-(6,7-dimethoxy-1,2,3,4-tetrahydronaphthyl)]amino}-4,4-diphenylheptane dihydrochloride

Example II-44

1'-(7-Acetylamino-4,4-diphenylheptyl)-3,4-dihydro-8-methoxyspiro[naphthalene-2(1H),2'-piperidine] dihydrochloride

Example II-45

1'-(7-Acetylamino-4,4-diphenylheptyl)-3,4-dihydro-6-methoxyspiro[naphthalene-2(1H),2'-piperidine] dihydrochloride

Example II-46

1'-(7-Acetylamino-4,4-diphenylheptyl)-3,4-dihydro-6,7-dimethoxyspiro[naphthalene-2(1H),2'-piperidine] dihydrochloride

Example II-47

1'-[7-(Cyclohexylacetyl)amino-4,4-diphenylheptyl]-3,4-dihydro-6,7-dimethoxyspiro[naphthalene-2(1H),2'-piperidine] hydrochloride

Example II-48

3,4-Dihydro-6,7-dimethoxy-1'-[4,4-diphenyl-7-(phenylacetylamino)heptyl]spiro[naphthalene-2(1H),2'-piperidine] hydrochloride

Example II-49

3,4-Dihydro-6,7-dimethoxy-1'-{4,4-diphenyl-7-[(2-fluorophenylacetyl)amino]heptyl}spiro[naphthalene-2 (1H),2'-piperidine] hydrochloride

Example II-50

3,4-Dihydro-6,7-dimethoxy-1'-{4,4-diphenyl-7-[(4-fluorophenylacetyl)amino]heptyl}spiro[naphthalene-2(1H),2'-piperidine] hydrochloride

Example II-51

3,4-Dihydro-6,7-dimethoxy-1'-{4,4-diphenyl-7-[(4-chlorophenylacetyl)amino]heptyl}spiro[naphthalene-2(1H),2'-piperidine] hydrochloride

Example II-52

3,4-Dihydro-6,7-dimethoxy-1'-{4,4-diphenyl-7-[(3-nitrophenylacetyl)amino]heptyl}spiro[naphthalene-2(1H),2'-piperidine] hydrochloride

Example II-53

3,4-Dihydro-6,7-dimethoxy-1'-{4,4-diphenyl-7-[(4-nitrophenylacetyl)amino]heptyl}spiro[naphthalene-2(1H),2'-piperidine] hydrochloride

Example II-54

3,4-Dihydro-6,7-dimethoxy-1'-{4,4-diphenyl-7-[(4-methylphenylacetyl)amino]heptyl}spiro[naphthalene-2(1H),2'-piperidine] hydrochloride

Example II-55

3,4-Dihydro-6,7-dimethoxy-1'-{4,4-diphenyl-7-[(4-trifluoromethylphenylacetyl)amino]heptyl}spiro[naphthalene-2(1H),2-piperidine] hydrochloride

Example II-56

3,4-Dihydro-6,7-dimethoxy-1'-{4,4-diphenyl-7-[(2-methoxyphenylacetyl)amino]heptyl}spiro[naphthalene-2(1H),2'-piperidine] hydrochloride

Example II-57

3,4-Dihydro-6,7-dimethoxy-1'-{4,4-diphenyl-7-[(3-methoxyphenylacetyl)amino]heptyl}spiro[naphthalene-2(1H),2'-piperidine] hydrochloride

Example II-58

3,4-Dihydro-6,7-dimethoxy-1'-{4,4-diphenyl-7-[(4-methoxyphenylacetyl)amino]heptyl}spiro[naphthalene-2(1H),2'-piperidine] hydrochloride

Example II-59

3,4-Dihydro-6,7-dimethoxy-1'-{7-[(3,4-dimethoxyphenylacetyl)amino]-4,4-diphenylheptyl}spiro[naphthalene-2(1H),2'-piperidine] hydrochloride

Example II-60

3,4-Dihydro-6,7-dimethoxy-1'-{4,4-diphenyl-7-[(3,4-methylenedioxyphenylacetyl)amino]heptyl}spiro[naphthalene-2(1H),2'-piperidine] hydrochloride

Example II-61

3,4-Dihydro-6,7-dimethoxy-1'-{4,4-diphenyl-7-[(phenoxyacetyl)amino]heptyl}spiro[naphthalene-2(1H),2'-piperidine] hydrochloride

Example II-62

3,4-Dihydro-6,7-dimethoxy-1'-{4,4-diphenyl-7-[(2-thienylacetyl)amino]heptyl}spiro[naphthalene-2(1H),2'-piperidine] hydrochloride

Example II-63

3,4-Dihydro-6,7-dimethoxy-1'-{4,4-diphenyl-7-[(3-thienylacetyl)amino]heptyl}spiro[naphthalene-2(1H),2'-piperidine] hydrochloride

Example II-64

3,4-Dihydro-6,7-dimethoxy-1'-{4,4-diphenyl-7-[(3-phenylpropionyl)amino]heptyl}spiro[naphthalene-2(1H),2'-piperidine] hydrochloride

Example II-65

3,4-Dihydro-6,7-dimethoxy-1'-{4,4-diphenyl-7-{[3-(4-methoxyphenyl)propionyl]amino}heptyl}spiro[naphthalene-2(1H),2'-piperidine] hydrochloride

Example II-66

3,4-Dihydro-6,7-dimethoxy-1'-{4,4-diphenyl-7-[(1-naphthylacetyl)amino]heptyl}spiro[naphthalene-2(1H),2'-piperidine] hydrochloride

Example II-67

3,4-Dihydro-6,7-dimethoxy-1'-{4,4-diphenyl-7-[(2-naphthylacetyl)amino]heptyl}spiro[naphthalene-2(1H),2'-piperidine] hydrochloride

Example II-68

3,4-Dihydro-6,7-dimethoxy-1'-{4,4-bis(4-fluorophenyl)-7-[(4-methoxyphenylacetyl)amino]heptyl}spiro[naphthalene-2(1H),2'-piperidine] hydrochloride

Example II-11

1-(3-Aminobenzylamino)-4,4-diphenyl-5-(tosylamino)pentane

To a solution of 4,4-diphenyl-1-(3-nitrobenzylamino)-5-(tosylamino)pentane (0.17 g) in ethanol (10 ml) was added hydrochloric acid (0.1 ml) as well as 10% palladium-on-carbon (80 mg) and the mixture was subjected to catalytic hydrogenation at atmospheric temperature and pressure. The catalyst was then removed from the reaction mixture and the filtrate was concentrated to dryness. The group was dissolved in water and the solution was made basic with aqueous ammonia. The resulting precipitate was recovered by filtration, rinsed with water, and dried to provide the title compound (0.12 g) as light-tan powder.

Example II-17

4,4-Diphenyl-5-mesylamino-1-(4-phenylpiperidino)pentane Hydrochloride

To a solution of 5-amino-4,4-diphenyl-1-(4-phenylpiperidino)pentane (0.4 g) and triethylamine (0.42 ml) in methylene chloride (15 ml) was added methanesulfonyl chloride (0.1 ml) dropwise under ice-cooling and stirring. After completion of dropwise addition, the mixture was returned to room temperature and stirred for another 3 hours. This reaction mixture was washed with water, dried over anhydrous sodium sulfate, and concentrated to dryness. The group was purified by silica gel column chromatography to provide the hydrochloride of the title compound (0.25 g) as colorless powder.

The compounds of Examples II-18 through II-24, II-30, II-32 through II-33, II-37 through II-38 were respectively synthesized in the same manner as Example II-17.

Example II-18

5-Benzenesulfonylamino-4,4-diphenyl-1-(4-phenylpiperidino)pentane

Example II-19

4,4-Diphenyl-1-(4-phenylpiperidino)-5-(2,4,6-trimethylbenzenesulfonylamino)pentane Example II-20

4,4-Diphenyl-1-(4-phenylpiperidino)-5-(2,4,6-triisopropylbenzenesulfonylamino)pentane Example II-21

4,4-Diphenyl-5-(1-naphthylsulfonylamino)-1-(4-phenylpiperidino)pentane

Example II-22

4,4-Diphenyl-5-(2-naphthylsulfonylamino)-1-(4-phenylpiperidino)pentane

Example II-23

3,4-Dihydro-6-methoxy-1'-(5-acetylamino-4,4-diphenylpentyl)spiro[naphthalene-2(1H),2'-piperidine] dihydrochloride Example II-24

3,4-Dihydro-6-methoxy-1'-(5-tosylamino-4,4-diphenylpentyl)spiro[naphthalene-2(1H),2'-piperidine] dihydrochloride Example II-30

4-(4-Methoxyphenyl)-5-(1-naphthylsulfonylamino)-4-phenyl-1-(4-phenylpiperidino)pentane hydrochloride Example II-32

4,4-Bis(4-chlorophenyl)-1-[4-(4-fluorophenyl)piperazin-1-yl]-5-(mesylamino)pentane dihydrochloride Example II-33

4,4-Bis(4-chlorophenyl)-1-[4-(4-fluorophenyl)piperazin-1-yl]-5-(tosylamino)pentane dihydrochloride Example II-37

3,4-Dihydro-6-methoxy-1'-(6-acetylamino-4,4-diphenylhexyl)spiro[naphthalene-2(1H),2'-piperidine] dihydrochloride Example II-38

3,4-Dihydro-6-methoxy-1'-(6-tosylamino-4,4-diphenylhexyl)spiro[naphthalene-2(1H),2'-piperidine] hydrochloride Example II-39

3,4-Dihydro-6-methoxy-1'-(6-benzylamino-4,4-diphenylhexyl)spiro[naphthalene-2(1H),2'-piperidine] dihydrochloride The structural formulas and physical properties of the above compounds are shown below.

TABLE 17

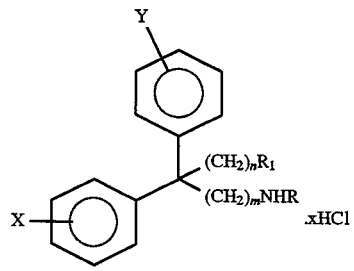

| Example | X | Y | R | $R_1$ | m | n | x | Melting Point (°C.) | $^1$H—NMR ($\delta_{ppm}$, $CDCl_3$) | Elemental Analysis [Cald./(Found)] C H N |
|---|---|---|---|---|---|---|---|---|---|---|
| II-1 | H | H | CHO | $N(CH_3)_2$ | 1 | 3 | — | 98–99 | 1.21–1.31(2H, m), 2.04–2.22 (2H, m), 2.09(6H, s), 4.05 (2H, d), 5.16(1H, br s), 7.13–7.37(10H, m), 8.09 (1H, s) | $C_{20}H_{26}N_2O \cdot 1/10H_2O$ 77.02 8.41 8.74 (76.93 8.46 8.97) |
| II-2 | H | H | CHO | —NCH$_2$—Ph / CH$_3$ | 1 | 3 | 1 | 97–105 | 1.20–1.36(2H, m), 2.04(3H, s), 2.02–2.15(2H, m), 2.28 (2H, t), 3.36(2H, s), 4.04 (2H, d), 5.11(1H, br t), 7.10–7.37(15H, m), 8.06 (1H, d) | $C_{26}H_{30}N_2O \cdot HCl \cdot 1/2H_2O$ 72.38 7.77 6.45 (72.29 7.47 6.48) |

TABLE 17-continued

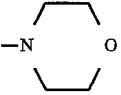

| Example | X | Y | R | R₁ | m | n | x | Melting Point (°C.) | $^1$H—NMR ($\delta_{ppm}$, CDCl₃) | Elemental Analysis [Cald./(Found)] C H N |
|---|---|---|---|---|---|---|---|---|---|---|
| II-3 | H | H | CHO | 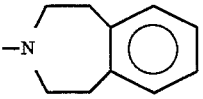 | 1 | 3 | 1 | | 1.26(2H, m), 2.00–2.30(6H, m), 3.64(4H, t)4.04(2H, d), 5.00–5.20(1H, br s), 7.10–7.40(9H, m), 8.09(1H, d) | C₂₂H₂₈N₂O₂.HCl.H₂O 64.67  7.69  6.77 (64.93  7.68  6.88) |
| II-4 | H | H | CHO | 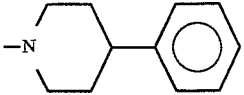 | 1 | 3 | 1 | 123–126 | 1.29(2H, m), 2.09(2H, m), 2.38(4H, t), 2.49(4H, m), 2.84(4H, m), 4.05(2H, d), 5.10(1H, br s), 7.00–7.40 (14H, m), 8.09(1H, d) | C₂₈H₃₂N₂O.HCl.H₂O 71.83  7.37  6.07 (72.01  7.55  6.00) |
| II-5 | H | H | CHO | 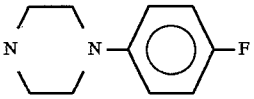 | 1 | 3 | 1 | | 1.20–1.40(2H, m), 1.55–2.23 (8H, m), 2.29(2H, t), 2.35–2.50(1H, m), 2.90(2H, d), 4.06(2H, d), 5.10–5.20(1H, br s), 7.10–7.35(15H, m), 8.11(1H, d) | |

TABLE 18

| Example | X | Y | R | R₁ | m | n | x | Melting Point (°C.) | $^1$H—NMR ($\delta_{ppm}$, CDCl₃) | Elemental Analysis [Cald./(Found)] C H N |
|---|---|---|---|---|---|---|---|---|---|---|
| II-6 | H | H | CHO | 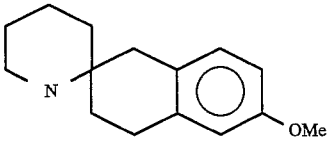 | 1 | 3 | 2 | 145–148 | 1.20–1.40(2H, m), 2.10–2.40(4H, m), 2.45(4H, t), 3.05(4H, t), 4.06(2H, d), 5.10 (1H, br s), 6.80–7.00 (4H, m), 7.10–7.40 (10H, m), 8.10(1H, d) | C₂₈H₃₂FN₃O.2HCl.1/4H₂O 63.79  6.67  7.90 (63.71  6.44  8.25) |
| II-7 | H | H | CHO | 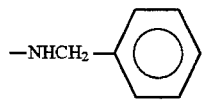 | 1 | 3 | 2 | | 1.05–1.30(2H, m), 1.35–2.80(18H, m), 3.76(3H, s), 4.02(2H, d), 5.30–5.40(1H, br t), 6.60–6.70 (2H, m), 6.96(1H, d), 7.10–7.35(10H, m), 8.08(1H, d) | C₃₃H₄₀N₂O₂.2HCl.3/2H₂O 66.54  7.35  4.32 (66.43  7.60  4.69) |
| II-8 | H | H | Ts | —NHCH₂— | 1 | 3 | 1 | | 1.06–1.22(2H, m), 2.10–2.21(2H, m), 2.40(3H, s), 2.50(2H, t), 3.55, 3.66(2H each, t), 7.02–7.37 (17H, m), 7.59(2H, d) | C₃₁H₃₄N₂O₂S.HCl.6/5H₂O 66.79  6.43  5.06 (66.88  6.77  5.03) |

TABLE 18-continued

| Example | X | Y | R | R₁ | m | n | x | Melting Point (°C.) | $^1$H—NMR ($\delta_{ppm}$, CDCl₃) | Elemental Analysis [Cald./(Found)] C H N |
|---|---|---|---|---|---|---|---|---|---|---|
| II-9 | H | H | Ts | —NCH₂—（phenyl）, with CH₃ on N | 1 | 3 | 1 | 115–118 | 1.07–1.22(2H, m), 2.04, 2.40(3H each, s), 2.08–2.18(2H, m), 2.24(2H, t), 3.34(2H, s), 3.56(2H, d), 4.16 (1H, br t), 7.05, 1.06, 7.58(2H each, d), 7.13–7.37(13H, m) | C₃₂H₃₆N₂O₂S.HCl.3/1H₂O  69.46  7.19  4.82  (69.30  6.83  5.05) |
| II-10 | H | H | Ts | —NHCH₂—（phenyl）-NO₂ | 1 | 3 | 1 | 111–115 | 1.09–1.25(2H, m), 2.15–2.25(2H, m), 2.41(3H, s), 2.53(2H, t), 3.55(2H, d), 3.78 (2H, s), 3.95(1H, br t), 7.02–7.09(4H, m), 7.18–7.31(8H, m), 7.47(1H, t), 7.57–7.63(3H, m), 8.06–8.18(2H, m), | C₃₁H₃₃N₃O₄S.HCl.3/5H₂O  63.13  5.93  6.78  (63.01  6.00  7.11) |
| II-11 | H | H | Ts | —NHCH₂—（phenyl）-NH₂ | 1 | 3 | — |  | 1.06–1.22(2H, m), 2.10–2.20(2H, m), 2.40(3H, s), 2.50 (2H, t), 3.55, 3.59 (2H each, s), 3.66(1H, br s), 6.52–6.55 (3H, m), 7.00–7.10 (4H, m), 7.16–7.29 (8H, m), 7.58(2H, d) | C₃₁H₃₅N₃O₂S.1/5H₂O  72.02  6.87  7.98  (71.98  6.90  8.12) |

TABLE 19

| Example | X | Y | R | R₁ | m | n | x | Melting Point (°C.) | $^1$H—NMR ($\delta_{ppm}$, CDCl₃) | Elemental Analysis [Cald./(Found)] C H N |
|---|---|---|---|---|---|---|---|---|---|---|
| II-12 | H | H | Ts | —NHCH₂—（phenyl）-CO₂Me | 1 | 3 | 1 |  | 1.05–1.24(2H, m), 2.11–2.20 (2H, m), 2.40(3H, s), 2.50 (2H, t), 3.54(2H, d), 3.71 (2H, s), 3.91(3H, s), 3.98 (1H, br s), 7.01–7.08(4H, m), 7.17–7.30(8H, m), 7.32–7.51(2H, m), 7.59(2H, dd), 7.92(2H, dd) | C₃₃H₃₆N₂O₄S.HCl.3/5H₂O  65.37  6.25  4.50  (65.62  6.37  4.64) |
| II-13 | H | H | Ts | —NHCH₂—（pyridyl） | 1 | 3 | 2 | 176–181 | 1.09–1.27(2H, m), 2.11–2.22(2H, m), 2.41(3H, s), 2.54(2H, t), 3.55, 3.80(2H each, s), 7.01–7.30(14H, m), 7.55–7.68(3H, m), 8.53 (1H, dd) | C₃₀H₃₃N₃O₂S.2HCl.1/2H₂O  61.85  6.20  7.25  (61.95  6.24  7.22) |
| II-14 | H | H | Ts | —N（azepane） | 1 | 3 | 1 |  | 1.03–1.20(2H, m), 1.55(8H, s), 2.06–2.17(2H, m), 2.33 (2H, t), 2.42(3H, s), 2.47 (4H, br s), 3.56(2H, s), 7.03–7.11(4H, m), 7.16–7.30(8H, m), 7.58(2H, d) | C₃₀H₃₈N₂O₂S.HCl.1/2H₂O  67.33  7.55  5.23  (67.20  7.52  5.22) |
| II-15 | H | H | Ts | —N（piperazinyl）N—（phenyl） | 1 | 3 | — | 146–147 | 1.11–1.30(2H, m), 2.12–2.26(2H, m), 2.28(2H, t), 2.42(3H, s), 2.43(4H, t), 3.13(4H, t), 3.56(2H, d), 3.94(1H, t), 6.80–6.95(3H, m), 7.06, 7.07, 7.59(2H each, d), 7.18–7.31(10H, m) | C₃₄H₃₉N₃O₂S  73.61  7.21  7.65  (73.74  7.10  7.59) |

TABLE 19-continued

| Example | X | Y | R | R₁ | m | n | x | Melting Point (°C.) | ¹H—NMR ($\delta_{ppm}$, CDCl₃) | Elemental Analysis [Cald./(Found)] C | H | N |
|---|---|---|---|---|---|---|---|---|---|---|---|---|
| II-16 | H | H | Ts | —N(piperazinyl)–N–(2-methoxyphenyl) | 1 | 3 | 1 | 112–117 | 1.15–1.30(2H, m), 2.12–2.25 (2H, m), 2.29(2H, t), 2.42 (3H, s), 2.49, 3.03(4H each, t), 3.57(2H, d), 3.85(3H, s), 3.99(1H, br t), 6.82–7.31 (16H, m), 7.59(2H, d) | $C_{35}H_{41}N_3O_3S \cdot HCl \cdot 6/5H_2O$ 65.50 (65.49 | 6.83 6.97 | 6.30 6.55) |
| II-17 | H | H | Ms | —N(4-phenylpiperidinyl) | 1 | 3 | 1 | 123–126 | 1.18–1.39(2H, m), 1.62–2.58 (14H, m), 2.86–3.05(2H, d), 3.75–3.90(2H, d), 4.60–4.77 (1H, br s), 7.13–7.37(15H, m) | $C_{29}H_{36}N_2O_2S \cdot HCl \cdot 3/2H_2O$ 64.40 (64.48 | 7.36 7.46 | 5.00 5.19) |

TABLE 20

| Example | X | Y | R | R₁ | m | n | x | Melting Point (°C.) | ¹H-NMR (δ_ppm, CDCl₃) | Elemental Analysis [Cald./(Found)] C H N |
|---|---|---|---|---|---|---|---|---|---|---|
| II-18 | H | H | 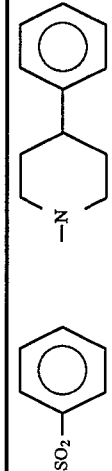 -SO₂- | -N⟨piperidine-Ph⟩ | 1 | 3 | — | 145–147 | 1.12–1.31(2H, m), 1.50–2.55(11H, m), 2.78–2.94(2H, d), 3.53–3.65(2H, d), 4.01–4.16(1H, m), 7.01–7.12(4H, m), 7.13–7.37 (11H, m), 7.40–7.62(3H, m), 7.66–7.75 (2H, m) | C₃₄H₃₈N₂O₂S 75.48 7.08 5.02 (75.80) 7.11 5.20) |
| II-19 | H | H | 3,5-Me₂-C₆H₃-SO₂- | -N⟨piperidine-Ph⟩ | 1 | 3 | — | 107–108 | 1.03–1.23(2H, m), 1.53–2.33(14H, m), 2.35–2.45(6H, s), 2.73–2.91(2H, d), 3.44–3.55(2H, d), 4.03–4.19(1H, m), 6.87–6.92 (2H, s),7.01–7.10(4H, dd), 7.13–7.34 (11H, m) | C₃₇H₄₄N₂O₂S 76.18 7.54 4.61 (76.51) 7.64 4.82) |
| II-20 | H | H | 2,4,6-iPr₃-C₆H₂-SO₂- | -N⟨piperidine-Ph⟩ | 1 | 3 | — | 139–140 | 1.10–1.33(20H, m), 1.53–2.53(11H, m), 2.75–2.97(3H, m), 3.55–3.68(2H, d), 3.80–4.17(3H, m), 7.05–7.36(17H, m) | C₄₈H₅₆N₂O₂S 76.37 8.31 3.81 (76.11) 8.54 4.13) |
| II-21 | H | H | 1-Naphthyl-SO₂- | -N⟨piperidine-Ph⟩ | 1 | 3 | — | — | 0.85–1.08(2H, m), 1.43–2.05(10H, m), 2.32–2.53(1H, m), 2.66–2.82(2H, m), 3.47–3.63(2H, d), 4.28–4.46(1H, br s), 6.88–7.34 (15H, m), 7.49–7.65(3H, m), 7.89–7.97(1H, m), 8.02–8.11(1H, d), 8.20–8.35(2H, m) | |
| II-22 | H | H | 2-Naphthyl-SO₂- | -N⟨piperidine-Ph⟩ | 1 | 3 | — | 150–152 | 1.05–1.27(2H, m), 1.50–1.90(6H, m), 2.05–2.25(4H, m), 2.28–2.55(1H, m), 2.70–2.85(2H, d), 3.58–3.68(2H, d), 4.13–4.30(1H, m), 7.00–7.34(15H, m), 7.56–7.71(3H, m), 7.86–7.99(3H, m), 8.31–8.35 (1H, d) | C₃₆H₄₀N₂O₂S 77.26 6.77 4.55 (77.51) 6.85 4.76) |
| II-23 | H | H | Ac | 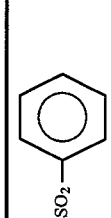 (methoxy-tetrahydronaphthalene spiro piperidine) | 1 | 3 | 2 | — | 1.40–3.10(24H, m), 3.77(3H, s), 4.00(2H, br s), 6.20–6.30(1H, br), 6.60–6.75(2H, m), 7.01(1H, d), 7.12–7.32(10H, m) | C₃₄H₄₂N₂O₂·2HCl·1/4H₂O 69.49 7.81 4.55 (69.37) 8.15 4.76) |

TABLE 21

| Example | X | Y | R | R₁ | m | n | x | Melting Point (°C.) | ¹H—NMR ($\delta_{ppm}$, CDCl₃) | Elemental Analysis [Cald./(Found)] C H N |
|---|---|---|---|---|---|---|---|---|---|---|
| II-24 | H | H | Ts | (spiro bicyclic structure with OMe, N) | 1 | 3 | 2 | — | 1.00–1.17(2H, m), 1.35–2.80(21H, m), 3.55(2H, d), 3.77 (3H, s), 4.00–4.15(1H, br t), 6.60–6.75(2H, m), 6.90–7.30(13H, m), 7.57(2H, d) | C₃₉H₄₆N₂O₃S·2HCl 67.26 6.96 3.69 (67.31 6.95 4.02) |
| II-25 | 4-Cl | H | CHO | (4-phenylpiperidine) | 1 | 3 | 1 | 118–123 | 1.20–1.39(2H, m), 1.40–2.19(8H, m), 2.29(2H, t), 2.32–2.53(1H, m), 2.89(2H, d), 4.03(2H, d), 5.21(1H, dd), 7.06–7.37(14H, s), 8.09(1H, d) | C₂₉H₃₃ClN₂O·HCl·1/2H₂O 68.99 7.24 5.48 (68.77 6.96 5.53) |
| II-26 | 4-Cl | H | CHO | (4-phenylpiperidine) | 1 | 3 | 2 | 133–138 | 1.20–1.36(2H, m), 2.03–2.15(2H, m), 2.31(2H, t), 2.46, 3.14(4H each, t), 4.03(2H, d), 5.10(1H, br t), 6.80–6.93(3H, m), 7.06–7.38(11H, m), 8.10(1H, d) | C₂₆H₃₂ClN₃O·2HCl·1/2H₂O 61.75 6.70 7.55 (61.83 6.49 7.72) |
| II-27 | 4-Cl | H | CHO | (4-(4-fluorophenyl)piperidine) | 1 | 3 | 2 | 138–143 | 1.17–1.39(2H, m), 2.09, 2.30(2H each, t), 2.46, 3.06(4H each, t), 4.03(2H, d), 5.11(1H, br t), 6.80–7.00(4H, m), 7.07–7.38(9H, m), 8.09(1H, d) | C₂₈H₃₁ClFN₃O·2HCl·1/2H₂O 59.98 6.37 7.47 (59.85 6.10 7.48) |
| II-28 | 4-Cl | H | CHO | (diphenylmethyl piperazine) | 1 | 3 | — | — | 1.10–1.30(2H, m), 1.97–2.10(2H, m), 2.24(2H, t), 2.22–2.42(8H, m), 3.99(2H, d), 4.18(1H, s), 5.17(1H, br t), 7.03–7.42(19H, m), 8.07(1H, d) | C₃₅H₃₈ClN₃O·1/5H₂O 70.91 6.93 7.05 (71.04 7.22 7.10) |
| II-29 | 4-MeO | H | CHO | (4-phenylpiperidine) | 1 | 3 | 1 | — | 1.15–1.40(2H, m), 1.60–2.20(8H, m), 2.28(2H, t), 2.30–2.50(1H, m), 2.90(2H, d), 3.79(3H, s), 4.02(2H, d), 5.10–5.30(1H, m), 6.83(2H, d), 7.00–7.20(12H, m), 8.09(2H, s) | C₃₀H₃₆N₂O₂·HCl·3/2H₂O 68.98 7.83 5.40 (69.28 7.75 5.39) |

TABLE 22

| Example | X | Y | R | R₁ | m | n | x | Melting Point (°C.) | ¹H-NMR (δ_ppm, CDCl₃) | Elemental Analysis [Cald./(Found)] C H N |
|---|---|---|---|---|---|---|---|---|---|---|
| II-30 | 4-MeO | H | 1-naphthyl-SO₂ | piperidinyl-phenyl | 1 | 3 | 1 | 115–120 | 1.05–1.30(2H, m), 1.70–2.60(11H, m), 3.01 (2H, d), 3.52(2H, dd), 3.72(3H, s), 4.50–4.70 (1H, br), 6.61(2H, d), 6.85(2H, d), 6.90–6.98 (2H, m), 7.05–7.30(8H, m), 7.48–7.60(3H, m), 7.88–7.93(1H, m), 8.04(1H, d), 8.21(1H, dd) 8.25–8.32(1H, m) | $C_{39}H_{42}N_2O_3S·HCl·5/4H_2O$ 68.75  6.55  4.05 (69.10)  6.40  4.13) |
| II-31 | 4-Cl | 4-Cl | CHO | 4-F-phenyl-piperazinyl | 1 | 3 | 2 |  | 1.20–1.38(2H, m), 2.00–2.10(2H, m), 2.40–2.50(4H, m), 3.06(4H, t), 4.00(2H, d), 5.00–5.15(1H, br), 6.80–7.15(8H, m), 7.22–7.35 (4H, m), 8.10(1H, d) | $C_{28}H_{30}Cl_2FN_3O·2HCl·3/2H_2O$ 54.76  5.84  6.77 (54.74)  5.74  6.84) |
| II-32 | 4-Cl | 4-Cl | Ms | 4-F-phenyl-piperazinyl | 1 | 3 | 2 |  | 1.15–1.35(2H, m), 2.15–2.25(2H, m), 2.40(2H, t), 2.51–2.61(4H, m), 2.70(3H, s), 3.11(4H, t), 3.76(2H, d), 4.25(1H, br t), 6.80–7.30 (12H, m) | $C_{28}H_{32}N_3O_2S·2HCl·H_2O$ 51.29  5.62  6.04 (51.31)  5.54  6.41) |
| II-33 | 4-Cl | 4-Cl | Ts | 4-F-phenyl-piperazinyl | 1 | 3 | 2 | 166–168 | 1.10–1.30(2H, m), 2.07–2.17(2H, m), 2.29 (2H, t), 2.43(3H, s), 2.41–2.51, (4H, m), 3.08(4H, t), 3.52(2H, d), 4.17(1H, br t), 5.80–7.00(8H, m), 7.20–7.30(6H, m), 7.56 (2H, d) | $C_{34}H_{36}Cl_2FN_3O_2S·2HCl·1/4H_2O$ 63.13  5.67  6.81 (63.29)  5.70  6.51) |
| II-34 | H | H | CHO | 4-F-phenyl-piperazinyl | 1 | 4 | 2 | 135–140 | 1.01–1.20(2H, m), 1.36–1.58(2H, m), 2.05–2.36(2H, m), 2.29(2H, t), 2.52, 3.08(4H each, t), 4.04(2H, d), 5.12(1H, br t), 6.81–7.01(4H, m), 7.12–7.39(10H, m), 8.09(1H, d) | $C_{29}H_{34}FN_3O·2HCl$ 65.56  7.10  7.81 (65.41)  6.81  7.89) |

TABLE 23

| Example | X | Y | R | R₁ | m | n | x | Melting Point (°C.) | ¹H—NMR ($\delta_{ppm}$, CDCl₃) | Elemental Analysis [Cald./(Found)] C H N |
|---|---|---|---|---|---|---|---|---|---|---|
| II-35 | H | H | CHO | 4-F-phenyl-piperazin-1-yl | 2 | 3 | 2 | 148–152 | 1.17–1.35(2H, m), 2.10–2.22(2H, m), 2.32, 2.35(2H each, t), 2.44, 3.05(4H each, t), 3.03–3.13(2H, m), 5.20(1H, br s), 6.79–6.98 (4H, m), 7.12–7.32(10H, m), 7.98(1H, d) | C₂₉H₃₄FN₃O·2HCl·1/2H₂O 64.48 6.72 7.56 (64.32 6.89 7.76) |
| II-36 | H | H | Ts | 4-phenyl-piperidin-1-yl | 2 | 3 | 1 | | 1.08–1.27(2H, m), 1.60–2.10(8H, m), 2.20–2.39(4H, m), 2.41(3H, s), 2.38–2.52(1H, m), 2.65–2.69(2H, m), 2.86(2H, d), 4.29(1H, br s), 7.05–7.35(17H, m), 7.58(2H, d) | C₃₆H₄₂N₂O₂S·HCl·1/2H₂O 70.61 7.11 4.46 (70.62 7.24 4.58) |
| II-37 | H | H | Ac | 6-OMe-1,2,3,4-tetrahydroisoquinolin-2-yl | 2 | 3 | 2 | | 1.27–1.79(7H, m), 1.82(3H, s), 1.82–1.96(2H, m), 2.00–2.20(3H, m), 2.33(2H, t), 2.48–2.62 (2H, m), 2.65–3.09(8H, m), 3.77(3H, s), 5.75 (1H, br s), 6.63, 6.96(1H each, d), 6.70(1H, dd), 7.11–7.32(10H, m) | C₃₅H₄₄N₂O₂·2HCl 70.26 7.80 4.80 (70.34 7.76 4.69) |
| II-38 | H | H | Ts | 6-OMe-1,2,3,4-tetrahydroisoquinolin-2-yl | 2 | 3 | 1 | | 0.96–1.15(2H, m), 1.35–2.08(11H, m), 2.18–2.80(11H, m), 2.41, 3.77(3H each, s), 4.10 (1H, br s), 6.61–6.72(2H, m), 6.95(1H, d), 7.02–7.30(12H, m), 7.57(2H, d) | C₄₀H₄₈N₂O₂S·HCl·H₂O 69.28 7.17 3.98 (69.49 7.44 4.05) |
| II-39 | H | H | CH₂-phenyl | 6-OMe-1,2,3,4-tetrahydroisoquinolin-2-yl | 2 | 3 | 2 | | 1.50–2.36(13H, m), 2.50–3.10(11H, m), 3.77 (3H, s), 3.87(2H, s), 6.64(1H, d), 6.73(1H, dd), 7.00(1H, d), 7.11–7.38(13H, m), 7.44–7.52(2H, m) | C₄₀H₄₈N₂O·2HCl·9/5H₂O 70.87 7.73 4.21 (70.84 7.97 4.13) |

TABLE 24

| Example | X | Y | R | R₁ | m | n | x | ¹H—NMR ($\delta_{ppm}$, CDCl₃) | Elemental Analysis [Cald./(Found)] C H N |
|---|---|---|---|---|---|---|---|---|---|
| II-40 | H | H | Ac | —NHCH₂—C₆H₄—CO₂Me | 3 | 3 | 2 | 1.10–1.35(4H, m), 1.90, 3.91(3H each, s), 2.02–2.17(4H, m), 2.59 (2H, t), 3.14(2H, q), 3.79(2H, s), 5.69(1H, br t), 7.10–7.30 (10H, m), 7.40(1H, t), 7.50–7.59 (1H, m), 7.95(1H, dt) | C₃₀H₃₆N₂O₃·2HCl·H₂O 63.79 6.79 4.53 (63.94 7.15 4.97) |
| II-41 | H | H | Ac | —NH(CH₂)₂—C₆H₅ | 3 | 3 | 2 | 1.13–1.46(4H, m), 1.94(3H, s), 2.02–2.20(4H, m), 2.73(2H, t), 2.97(4H, s), 3.15(2H, q), 6.04 (1H, br t), 7.08–7.33(15H, m) | C₂₉H₃₆N₂O·2HCl·8/5H₂O 65.51 7.23 4.57 (65.68 7.83 5.28) |
| II-42 | H | H | Ac | NH-(6,7-dimethoxy-tetrahydronaphthalen-2-yl) | 3 | 3 | 2 | 1.10–1.30(2H, m), 1.45–1.70(2H, m), 1.97(3H, s), 2.05–2.35(5H, m), 2.70–3.20(9H, m), 3.77(3H, s), 3.82(3H, s), 6.50(2H, d), 6.70–6.80(1H, br), 7.05–7.30(10H, m) | C₃₃H₄₂N₂O₃·2HCl·1.5/2H₂O 62.72 7.27 4.14 (62.64 7.80 4.43) |
| II-43 | H | H | Ac | —N(CH₂Ph)(6,7-dimethoxy-tetrahydronaphthalen-2-yl) | 3 | 3 | 2 | 1.00–1.20(4H, m), 1.50–2.15(11H, m), 2.46(2H, t), 2.60–2.90(5H, m), 3.10(2H, dd), 3.57(2H, dd), 3.82 (3H, s), 3.84(3H, s), 5.00–5.10(1H, br), 6.55(2H, d), 7.08–7.35(15H, m) | C₄₀H₄₈N₂O₃·2HCl·1.5/2H₂O 66.55 7.13 3.65 (66.46 7.67 3.87) |
| II-44 | H | H | Ac | spiro-piperidine-methoxy-tetrahydronaphthalene | 3 | 3 | 2 | 1.10–1.30(2H, m), 1.35–1.80(4H, m), 1.91(3H, s), 2.00–2.18(2H, m), 2.20–2.40(1H, m), 2.40–2.60 (4H, m), 2.70–2.95(3H, m), 3.16(2H, dd), 3.81(3H, s), 5.48–5.64(1H, br), 6.68(2H, t), 7.02–7.30(11H, m) | C₃₆H₄₆N₂O₂·2HCl·1.5/2H₂O 65.92 7.51 4.12 (65.83 8.13 4.27) |

TABLE 25

| Example | X | Y | R | R₁ | m | n | x | ¹H—NMR (δ_ppm, CDCl₃) | Elemental Analysis [Cald./(Found)] C H N |
|---|---|---|---|---|---|---|---|---|---|
| II-45 | H | H | Ac | (tetrahydroisoquinoline with OMe)—N— | 3 | 3 | 2 | 1.00–2.80(24H, m), 3.15(2H, dd), 3.77(3H, s), 5.20–5.40(1H, br), 6.60–6.70(2H, m), 6.95(1H, d), 7.10–7.30(10H, m) | C₃₆H₄₆N₂O₂·2HCl·H₂O 68.64 7.83 4.31 (68.66 8.00 4.45) |
| II-46 | H | H | Ac | (tetrahydroisoquinoline with 2×OMe)—N— | 3 | 3 | 2 | 1.10–1.30(4H, m), 1.42–2.87(23H, m), 3.17 (2H, q), 3.83, 3.85(3H each, s), 5.40(1H, br), 6.56, 6.58(1H each, s), 7.10–7.30(10H, m) | C₃₇H₄₈N₂O₃·2HCl·1/5H₂O 68.84 8.04 4.05 (68.87 7.87 4.34) |
| II-47 | H | H | —COCH₂—(cyclohexyl) | (tetrahydroisoquinoline with 2×OMe)—N— | 3 | 3 | 1 | 0.80–2.17(29H, m), 2.20–2.82(8H, m), 3.18 (2H, q), 3.83, 3.85(3H each, s), 5.23(1H, br t), 6.55, 6.58(1H each, s), 7.10–7.30 (10H, m) | C₄₃H₅₈N₂O₃·HCl·2H₂O 71.13 8.21 3.67 (71.39 8.78 3.87) |
| II-48 | H | H | COCH₂—(phenyl) | (tetrahydroisoquinoline with 2×OMe)—N— | 3 | 3 | 1 | 1.02–1.22(4H, m), 1.40–2.80(20H, 3), 3.14(2H, q), 3.56(2H, s), 3.83(6H each, s), 6.52, 6.56(1H each, s), 7.00–7.38(15H, m) | C₄₃H₅₂N₂O₃·HCl·H₂O 74.10 7.54 3.47 (73.85 7.93 4.01) |
| II-49 | H | H | COCH₂—(2-F-phenyl) | " | 3 | 3 | 1 | 0.98–1.22(4H, m), 1.38–2.11(12H, m), 2.17–2.80(8H, m), 3.15(2H, q), 3.53(2H, s), 3.83, 3.84(3H each, s), 5.34(1H, br t), 6.54, 6.57 (1H, each, s), 7.00–7.32(14H, m) | C₄₃H₅₁FN₂O₃·HCl·2H₂O 70.21 7.50 3.81 (70.23 7.68 3.81) |
| II-50 | H | H | COCH₂—(4-F-phenyl) | " | 3 | 3 | 1 | 1.00–1.21(4H, m), 1.38–2.10(12H, m), 2.17–2.80(8H, m), 3.14(2H, q), 3.47(2H, s), 3.82 3.84(3H each, s), 5.24(1H, br t), 6.55, 6.57 (1H each, s), 6.95–7.29(14H, m) | C₄₃H₅₁FN₂O₃·HCl·2H₂O 70.32 7.30 3.97 (70.23 7.68 3.81) |

TABLE 26

| Example | X | Y | R | R₁ | m | n | x | ¹H—NMR ($\delta_{ppm}$, CDCl₃) | Elemental Analysis [Cald./(Found)] C H N |
|---|---|---|---|---|---|---|---|---|---|
| II-51 | H | H | COCH₂—C₆H₄—Cl (para) | (6,7-dimethoxy-tetrahydronaphthalen-2-yl piperidine) | 3 | 3 | 1 | 1.00–1.20(4H, m), 1.35–2.80(20H, m), 3.15 (2H, q), 3.47(2H, s), 3.83, 3.84(3H each, s), 5.20–5.35(1H, br), 6.55, 6.58(1H each, s), 7.05–7.32(14H, m) | C₄₃H₅₁N₂O₃Cl.HCl.5/2H₂O 68.25  7.29  3.99 (67.88)  7.55  3.68 |
| II-52 | H | H | COCH₂—C₆H₄—NO₂ (meta) | " | 3 | 3 | 1 | 1.00–1.25(4H, m), 1.35–2.80(20H, m), 3.16 (2H, q), 3.56(2H, s), 3.82, 3.84(3H each, s), 5.50–5.65(1H, br), 6.55, 6.58(1H each, s), 7.05–7.30(12H, m), 7.40–7.70(2H, m) | C₄₃H₅₁N₃O₅.HCl.2H₂O 68.11  7.16  5.76 (67.74)  7.40  5.51 |
| II-53 | H | H | COCH₂—C₆H₄—NO₂ (para) | " | 3 | 3 | 1 | 1.05–1.25(4H, m), 1.35–3.05(20H, m), 3.15 (2H, q), 3.58(2H, s), 3.82, 3.84(3H each, s), 5.35–5.70(1H, br), 6.55, 6.58(1H each, s), 7.05–7.50(14H, m) | C₄₃H₅₁N₃O₅.HCl.3H₂O 66.51  7.36  4.87 (66.18)  7.49  5.30 |
| II-54 | H | H | COCH₂—C₆H₄—Me (para) | " | 3 | 3 | 1 | 1.05–1.30(4H, m), 1.41–1.68(6H, m), 1.80–2.00(6H, m), 2.32(3H, s), 2.40–3.00(8H, m), 3.10–3.20(2H, m), 3.51(2H, s), 3.83(6H, s), 5.70–5.90(1H, br), 6.55, 6.57(1H each, s), 7.05–7.26(14H, m) | C₄₄H₅₄N₂O₃.HCl.3H₂O 70.59  6.99  3.77 (70.52)  8.20  3.74 |
| II-55 | H | H | COCH₂—C₆H₄—CF₃ (para) | " | 3 | 3 | 1 | 1.05–1.20(4H, m), 1.32–1.58(6H, m), 1.60–2.08(6H, m), 2.24–2.96(8H, m), 3.10–3.22 (2H, m), 3.55(2H, s), 3.83, 3.84(3H each, s), 5.55–5.75(1H, br), 6.55, 6.58(1H each, s), 7.07–7.27(10H, m), 7.39(2H, d), 7.58 (2H, d) | C₄₄H₅₁N₂F₃O₃.HCl.3/2H₂O 68.34  7.42  3.27 (68.07)  7.14  3.02 |

TABLE 27

| Example | X | Y | R | R₁ | m | n | x | ¹H—NMR (δ$_{ppm}$, CDCl₃) | Elemental Analysis [Cald./(Found)] C, H, N |
|---|---|---|---|---|---|---|---|---|---|
| II-56 | H | H | COCH₂-(2-MeO-C₆H₄) | spiro-tetrahydronaphthalene-6,7-diOMe piperidine | 3 | 3 | 1 | 0.98–1.18(4H, m), 1.40–2.10(12H, m), 2.19–2.79(8H, m), 3.12(2H, q), 3.52(2H, s), 3.78, 3.83, 3.85(3H each, s), 5.53(1H, br t), 6.55, 6.57(1H each, s), 6.85–6.98(2H, m), 7.05–7.31 (12H, m) | C₄₄H₅₄N₂O₄·HCl·3/2H₂O 71.34 7.71 3.35 (74.57 7.92 3.79) |
| II-57 | H | H | COCH₂-(3-OMe-C₆H₄) | " | 3 | 3 | 1 | 0.98–1.20(4H, m), 1.40–2.08(12H, m), 2.20–2.79(8H, m), 3.13(2H, q), 3.49(2H, s), 3.76, 3.83, 3.84(3H each, s), 5.26(1H, br t), 6.54, 6.57(1H each, s), 6.76–6.85(3H, m), 7.05–7.29 (11H, m) | C₄₄H₅₄N₂O₄·HCl·3/2H₂O 71.63 7.64 3.75 (71.57 7.92 3.79) |
| II-58 | H | H | COCH₂-(4-OMe-C₆H₄) | " | 3 | 3 | 1 | 1.00–1.19(4H, m), 1.38–2.10(12H, m), 2.18–2.80(8H, m), 3.13(2H, q), 3.46(2H, s), 3.77, 3.83, 3.85(3H each, s), 5.23(1H, br t), 6.55, 6.58(1H each, s), 6.86(2H, d), 7.06–7.26(12H, m) | C₄₄H₅₄N₂O₄·HCl·2H₂O 70.69 7.37 3.57 (70.71 7.96 3.75) |
| II-59 | H | H | COCH₂-(3,4-diOMe-C₆H₃) | " | 3 | 3 | 1 | 0.98–1.18(4H, m), 1.33–2.10(12H, m), 2.20–2.80(8H, m), 3.15(2H, q), 3.46(2H, s), 3.82, 3.83, 3.84, 3.85(3H each, s), 5.24(1H, br t), 6.55, 6.57(1H each, s), 6.70–6.82(3H, m), 7.03–7.28(10H, m) | C₄₅H₅₆N₂O₅·HCl·3/2H₂O 70.06 7.54 3.43 (70.34 7.87 3.65) |

TABLE 28

| Example | X | Y | R | R₁ | m | n | x | ¹H—NMR ($\delta_{ppm}$, CDCl₃) | Elemental Analysis [Cald./(Found)] C H N |
|---|---|---|---|---|---|---|---|---|---|
| II-60 | H | H | COCH₂O-(2,4-diOMe-phenyl) | (spiro tetrahydronaphthalene-piperidine with OMe groups) | 3 | 3 | 1 | 0.98–1.20(4H, m), 1.35–2.80(20H, m), 3.14 (2H, q), 3.42(2H, s), 3.83, 3.84(3H each, s), 5.27–5.30(1H, br), 5.91(2H, s), 6.55, 6.57(1H each, s), 6.62–6.80(3H, m), 7.05–7.29(10H, m) | C₄₄H₅₂N₂O₅·HCl·1.5/2H₂O 68.48 7.33 3.49 (68.60 7.59 3.64) |
| II-61 | H | H | COCH₂O-phenyl | " | 3 | 3 | 1 | 1.00–2.80(24H, m), 3.27(2H, q), 3.83, 3.84 (3H each, s), 4.45(2H, s), 6.41(1H, br t), 6.55, 6.57(1H each, s), 6.87–7.95(15H, m) | C₄₃H₅₂N₂O₄·HCl·H₂O 72.70 7.75 3.92 (72.46 7.51 3.65) |
| II-62 | H | H | COCH₂-(2-thienyl) | " | 3 | 3 | 1 | 1.00–1.20(4H, m), 1.30–2.80(20H, m), 3.16 q), 3.72(2H, s), 3.82, 3.84(3H each, s), 5.50–5.70(1H, br), 6.55, 6.58(1H each, s), 6.85–7.00(2H, m), 7.05–7.30(11H, m) | C₄₁H₅₀N₂O₃S·HCl·1.5/2H₂O 67.61 7.61 4.17 (67.24 7.71 3.82) |
| II-63 | H | H | COCH₂-(3-thienyl) | " | 3 | 3 | 1 | 1.00–1.20(4H, m), 1.33–2.10(13H, m), 2.20–2.80(7H, m), 3.15(2H, q), 3.55(2H, m), 3.83 3.84(3H each, s), 5.31(1H, br t), 6.55, 6.57 (1H each, s), 6.97(1H, d), 7.05–7.37 | C₄₁H₅₀N₂O₃S·HCl·H₂O 69.83 7.27 4.21 (69.81 7.57 3.97) |
| II-64 | H | H | CO(CH₂)₂-phenyl | " | 3 | 3 | 1 | 1.06–1.70(8H, m), 1.84–2.17(4H, m), 2.41–3.00 (16H, m), 3.17(2H, q), 3.83(6H, s), 6.55, 6.56 (1H each, s), 7.08–7.30(15H, m) | C₄₄H₅₄N₂O₃·HCl·2H₂O 72.55 7.86 3.47 (72.25 8.13 3.83) |

TABLE 29

| Example | X | Y | R | R₁ | m | n | x | ¹H—NMR ($\delta_{ppm}$, CDCl₃) | Elemental Analysis [Cald./(Found)] C H N |
|---|---|---|---|---|---|---|---|---|---|
| II-65 | H | H | 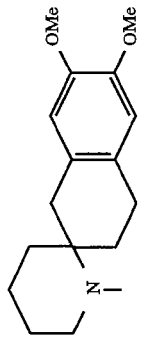 CO(CH₂)₂—⟨C₆H₄⟩—OMe | 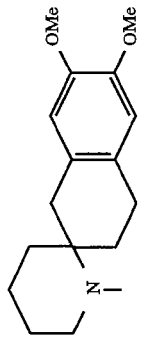 | 3 | 3 | 1 | 1.02–1.21(4H, m), 1.38–2.10(12H, m), 2.35, 2.86(2H each, t), 2.25–2.85(8H, m), 3.13 (2H, q), 3.73, 3.82, 3.84(3H each, s), 5.22 (1H, br t), 6.55, 6.57(1H each, s), 6.79 (2H, d), 7.05–7.30(12H, m) | C₄₅H₅₆N₂O₄·HCl·3/2H₂O 72.11  7.83  3.52 (71.83  8.04  3.72) |
| II-66 | H | H | 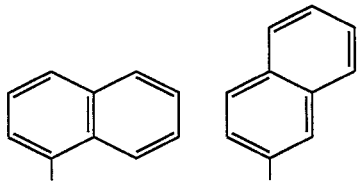 COCH₂—(1-naphthyl) | " | 3 | 3 | 1 | 0.86–1.06(4H, m), 1.38–2.01(12H, m), 2.13–2.79(8H, m), 3.07(2H, q), 3.83, 3.74 (3H each, s), 3.99(2H, s), 5.14(1H, br t), 6.55, 6.57(1H each, s), 6.94(4H, dd), 7.06–7.22(6H, m), 7.34–7.56(4H, m), 7.80–8.00(3H, m) | C₄₇H₅₄N₂O₃·HCl·3/2H₂O 74.17  7.39  3.76 (74.43  7.71  3.69) |
| II-67 | H | H | 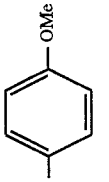 COCH₂—(2-naphthyl) | " | 3 | 3 | 1 | 0.96–1.20(4H, m), 1.33–2.07(12H, m), 2.13–2.80(8H, m), 3.14(3H each, q), 3.69(2H, s), 3.83, 3.84(3H each, s), 5.27(1H, br t), 6.54, 6.57(1H each, s), 7.00–7.25(10H, m), 7.35(1H, dd), 7.43–7.52(2H, m), 7.69 (1H, s), 7.75–7.87(3H, m) | C₄₇H₅₄N₂O₃·HCl·2H₂O 73.32  7.57  3.33 (73.56  7.57  3.65) |
| II-68 | 4-F | 4-F | COCH₂—⟨C₆H₄⟩—OMe | " | 3 | 3 | 1 | 0.95–1.18(4H, m), 1.38–2.05(12H, m), 2.70–2.79(8H, m), 3.13(2H, q), 3.47(2H, s), 3.78, 3.83, 3.84(3H each, s), 5.25(1H, br t), 6.55, 6.57(1H each, s), 6.83–7.18 (12H, m) | C₄₄H₅₂F₂N₂O₄·HCl·2H₂O 67.31  7.07  3.46 (67.46  7.33  3.58) |

Example III-1

(1) 4,4-Diphenyl-5-hydroxyl-6-heptenenitrile

Under argon gas, 4,4-diphenyl-4-formylbutanenitrile (5.0 g) was dissolved in dry tetrahydrofuran (200 ml). Then, 1M vinylmagnesium bromide-tetrahydrofuran (30 ml) was added dropwise −40° C. After completion of addition, the reaction temperature was allowed to rise gradually to 0° C. (over 3 hours). After completion of the reaction, a saturated aqueous solution of ammonium chloride was added to the reaction mixture and the insoluble matter was filtered off. The filtrate was extracted with ethyl acetate, washed, dried, and concentrated and the group was purified by silica gel column chromatography. The active fraction was concentrated to provide the title compound as oil (5.4 g).

$^1$H-NMR (CDCl$_3$, δ): 1.90–2.28(2H,m), 2.41–2.70(2H, m), 4.90(1H,dd), 5.21(2H,dd), 5.49–5.66(1H,m), 7.20–7.36 (10H,m)

(2) 7-(6,7-Dimethoxy-1,2,3,4-tetrahydronaphthalene-2-spiro-2'-piperidin-1'-yl)-4,4-diphenyl-5-heptenenitrile Hydrochloride In tetrahydrofuran (5 ml) was dissolved 4,4-diphenyl-5-hydroxyl-6-heptenenitrile (377 mg) followed by addition of phosphorus tribromide (0.04 ml) with cooling on an ice-water bath. The mixture was stirred at room temperature for 1 hour, at the end of which time it was extracted with ethyl acetate. The allyl bromide thus obtained was not purified but used in crude form in the next reaction.

In N,N-dimethylformamide (3 ml) was suspended 6,7-dimethoxy-1,2,3,4-tetrahydronaphthalene-2-spiro-2'-piperidine hydrochloride (193 mg) followed by addition of potassium carbonate (90 mg) and the mixture was stirred for 30 minutes. Then, a solution of the crude allyl bromide in N,N-dimethylformamide was added to the above mixture and a further amount (90 mg) of potassium carbonate was added. The reaction was carried out at 60° C. for 15 hours and this reaction mixture was extracted with ethyl acetate, washed, dried, and concentrated. The group was purified by silica gel column chromatography and the active fraction was concentrated and treated with 4N HCl-ethyl acetate to provide the hydrochloride (200 mg, powder).

$^1$H-NMR (CDCl$_3$, δ): 1.50(6H,br), 1.65–1.95(2H,m), 2.04–2.14(2H,m), 2.57–2.88(8H,m), 3.07–3.31(2H,m), 3.83 (6H,s), 5.32(1H,dt), 6.15(1H,d), 6.54(1H,s), 6.57(1H,s), 7.10–7.34(10H,m)

(3) 1-(7-Amino-4,4-diphenyl-2-heptenyl)-6',7'-dimethoxy-1',2',3',4'-tetrahydronaphthalene-2'-spiro-2-piperidine 7-(6,7-Dimethoxy-1,2,3,4-tetrahydronaphthalene-2-spiro-2'-piperidin-1'-yl)-4,4-diphenyl-5-heptenenitrile (free base, 200 mg) was mixed with hydrazine hydrate (4 ml) and Raney nickel (0.6 g) in the presence of ethanol (10 ml) and the reaction was carried out at 80° C. for 2 hours. After the reaction, the nickel was filtered off and the filtrate was concentrated to provide the title compound (free base, 170 mg).

$^1$H-NMR (CDCl$_3$, δ): 1.46–1.98(14H,m), 2.20–2.30(2H, m), 2.56–2.74(6H,m), 3.07–3.30(2H,m), 3.83(6H,s), 5.28 (1H,dt), 6.19(1H,d), 6.55(1H,s), 6.57(1H,s), 7.15–7.30(10H, m)

Example III-2

N-(7-(6,7-Dimethoxy-1,2,3,4-tetrahydronaphthalene-2-spiro-2'-piperidin-1'-yl)-4,4-diphenyl-5-heptenyl)-3-(4-methoxyphenyl)propionamide Hydrochloride In ethyl acetate (5 ml) was dissolved 1-(7-amino-4,4-diphenyl-2-heptenyl)-6',7'-dimethoxy-1',2',3',4'-tetrahydronaphthalene-2'-spiro-2-piperidine (free base, 150 mg) followed by addition of a saturated aqueous solution of sodium carbonate (3 ml). With this biphasic solution being stirred, 3-(4-methoxyphenyl)propionyl chloride (170 mg)-ethyl acetate solution (1 ml) was gradually added. After completion of the reaction, the organic layer was washed with water and concentrated and the group was purified by silica gel column chromatography. The active fraction was concentrated and treated with 4N HCl-ethyl acetate to provide the hydrochloride (60 mg, powder).

$^1$H-NMR (CDCl$_3$, δ): 1.16–1.32(2H,m), 1.45–1.66(6H, m), 1.72–2.04(2H,m), 2.16–2.30(2H,m), 2.41 (2H,m), 2.68 (4H,m), 2.89(4H,m), 3.19(4H,m), 3.70 (3H,s), 3.82(6H,s), 5.2–5.4(1H,m), 6.15(1H,d), 6.5 5(1H,s), 6.57(1H,s), 6.76 (2H,d), 7.09–7.31 (12H,m)

The following compounds were obtained according to the same method of Example III-2.

Example IV-1

4,4-Diphenyl-1-[(6-methoxy-1,2,3,4-tetrahydro-2-naphthyl)amino]-7-{[3-(4-methoxyphenyl)propionyl]amino}heptane Hydrochloride

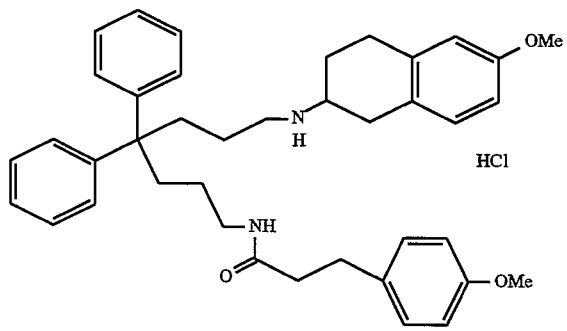

$^1$H-NMR (CDCl$_3$, δ): 1.04–1.25(4H,m), 1.40–1.53(1H, m), 1.80–2.19(6H,m), 2.29–2.56(3H,m), 2.62(2H,t), 2.70–2.95(6H,m), 3.13(2H,q), 3.72,3.75(3H each,s), 5.30 (1H,br t), 6.58–6.73(2H,m), 6.78(2H,d), 6.95(1H,d), 7.02–7.30(12H,m).

Example IV-2

4,4-Diphenyl-1-[3-(4-methoxyphenyl)piperidino]-7-{[3-(4-methoxyphenyl)propionyl]amino}heptane Hydrochloride

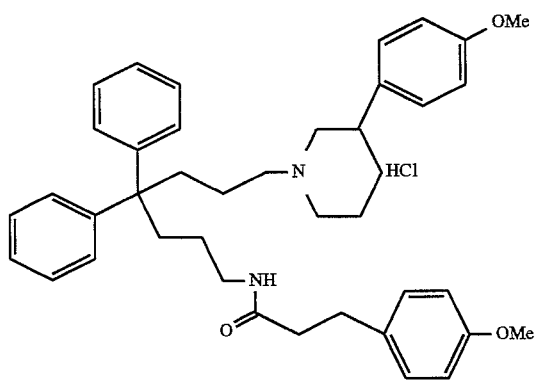

$^1$H-NMR (CDCl$_3$, δ): 1.00–1.45(4H,m), 1.55–2.15(10H, m), 2.19–2.37(4H,m), 2.63–2.90(5H,m), 3.13(2H,q), 3.73, 3.78(3H each,s), 5.13(1H,br t), 6.75–6.86(4H,m), 7.03–7.30 (14H,m).

Example IV-3

4,4-Diphenyl-1-(4-phenylpiperidino)-7-[(3-phenylpropionyl)amino]heptane Hydrochloride

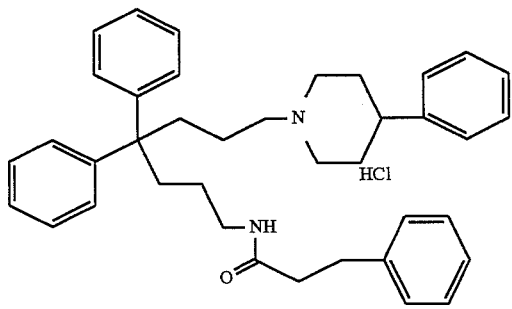

$^1$H-NMR (CDCl$_3$, δ): 1.00–1.38(4H,m), 1.59–1.90(4H, m), 1.95–2.30(4H,m), 2.34–2.60(6H,m), 2.86–3.20(7H,m), 5.73(1H,br t), 7.08–7.35(20H,m).

Example IV-4

4,4-Diphenyl-1-[4-(3-methoxyphenyl)piperidino]-7-[(3-phenylpropionyl)amino]heptane Hydrochloride

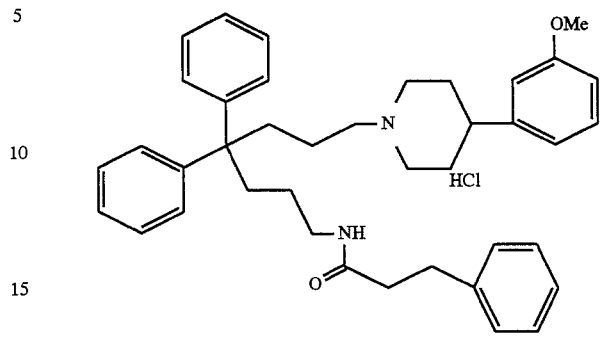

$^1$H-NMR (CDCl$_3$, δ): 1.00–1.35(4H,m), 1.70–2.13(8H, m), 2.28–2.61(6H,m), 2.87–3.05(5H,m), 3.13(2H,q), 3.77 (3H,s), 5.51(1H,br t), 6.69–6.80(3H,m), 7.08–7.30(16H,m).

Example IV-5

4,4-Diphenyl-1-[4-(4-methoxyphenyl)piperidino]-7-{[3(4-methoxyphenyl)propionyl]amino}heptane Hydrochloride

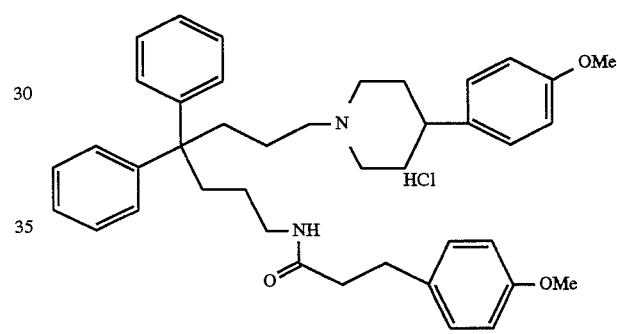

$^1$H-NMR (CDCl$_3$, δ): 1.04–1.28(4H,m), 1.54–2.17(10H, m), 2.19–2.45(5H,m), 2.86(4H,t), 3.14(2H,q), 3.72,3.76(3H each,s), 5.22(1H,br t), 6.73–6.86(4H,m), 7.02–7.30(14H,m).

Example IV-6

4,4-Diphenyl-7-{[3-(4-methoxyphenyl)propionyl]-amino}-1-[2,3,4,5-tetrahydro-3(1H)-benzazepin-3-yl]heptane Hydrochloride

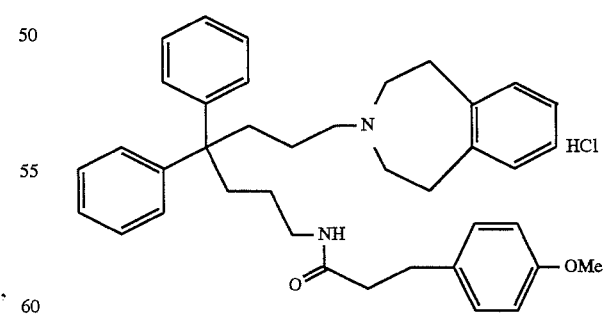

¹H-NMR (CDCl₃, δ): 1.03–1.29(4H,m), 1.98–2.15(4H, m), 2.28–2.53(8H,m), 2.80–2.92(6H,m), 3.13(2H,q), 3.72 (3H,s), 5.23(1H,br t), 6.78(2H,d), 7.00–7.32(16H,m).

Example IV-7

1-[7-Acetyl-2,3,4,5-tetrahydro-3(1H)-benzazepin-3-yl]-4,4-diphenyl-7-{[3-(4-methoxyphenyl)propionyl]-amino}heptane Hydrochloride

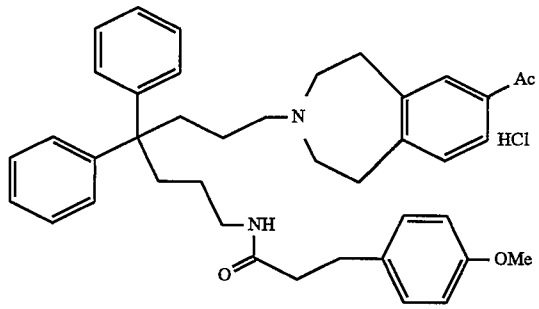

¹H-NMR (CDCl₃, δ): 1.04–1.25(4H,m), 2.00–2.55(12H, m), 2.56(3H,s), 2.80–2.94(6H,m), 3.15(2H,q), 3.73(3H,s), 5.21(1H,br t), 6.78(2H,d), 7.04–7.31(13H,m), 7.62–7.72 (2H,m).

Example IV-8

4,4-Diphenyl-1-(7,8-dimethoxy-2,3,4,5-tetrahydro-3 (1H)-benzazepin-3-yl)-7-{[3-(4-methoxyphenyl) propionyl]amino}heptane Hydrochloride

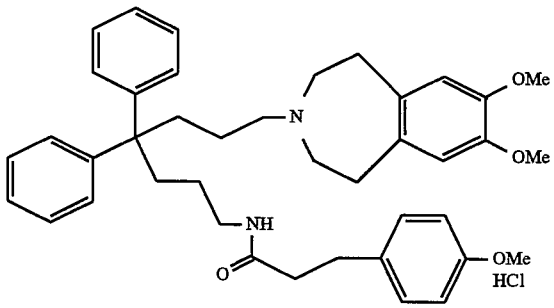

¹H-NMR (CDCl₃, δ): 1.06–1.30(4H,m), 2.01–2.12(4H, m), 2.35,2.87(2H each,t), 2.33–2.52(6H,m), 2.74–2.85(4H, m), 3.15(2H,q), 3.74(3H,s), 3.83(6H,s), 5.17(1H,br t), 6.60 (2H,s), 6.79,7.09(2H each,d), 7.10–7.31(10H,m).

Example IV-9

1-(8,9-Dimethoxy-6,6-dimethyl-1,2,3,4,5,6-hexahydro-3-benzazocin-3-yl)-4,4-diphenyl-7-{[3-(4-methoxyphenyl)propionyl]amino}heptane Hydrochloride

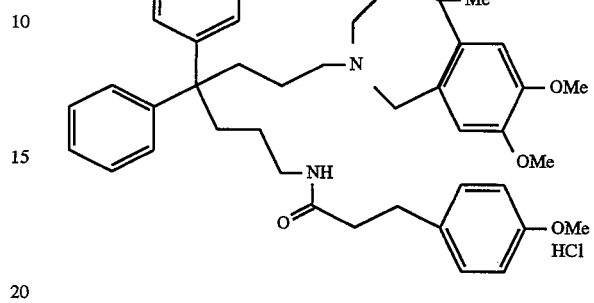

¹H-NMR (CDCl₃, δ): 0.78–0.98(4H,m), 1.38(6H,s), 1.50–1.72(4H,m), 1.79–2.22(6H,m), 2.30–2.62(6H,m), 2.87 (2H,t), 3.07(2H,q), 3.73,3.77,3.79(3H each,s), 5.54(1H,br t), 6.47(1H,s), 6.78(2H,d), 6.90–6.99(4H,m), 7.04–7.27(9H, m).

Example IV-10

4,4-Diphenyl-7-{[3-(4-methoxyphenyl)propionyl] amino}-1-(cis-1,2,3,4,4a,9,10,10a-octahydrobenzo[f] quinolin-1-yl)heptane Hydrochloride

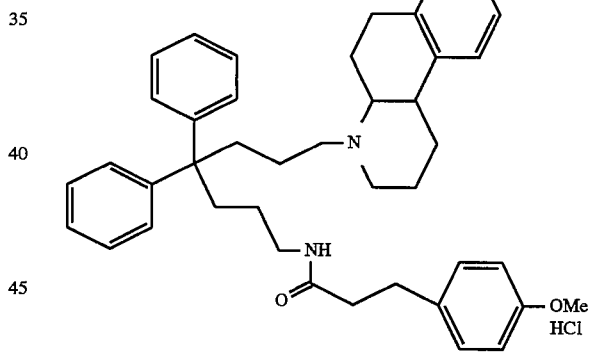

¹H-NMR (CDCl₃, δ): 1.00–1.30(4H,m), 1.50–3.20(24H, m), 3.73(3H,s), 5.15(1H,br s), 6.78(2H,d), 6.98–7.30(16H, m).

Example IV-11

1-(3-Aza-6-methyl-1,1a,2,3,4,4a-hexahydro-9-fluorenon-3-yl)-4,4-diphenyl-7-{[3-(4-methoxyphenyl)propionyl]amino}heptane Hydrochloride

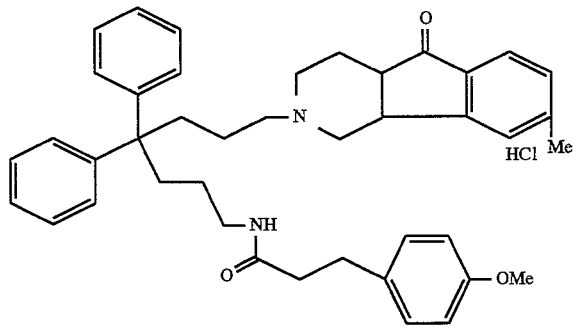

¹H-NMR (CDCl₃, δ): 1.00–1.30(4H,m), 1.45–3.40(21H, m), 3.73(3H,s), 5.20(1H,br t), 6.76(2H,d), 7.06–7.30(14H, m), 7.64(1H,d).

Example IV-12

3,4-Dihydro-1'-{4,4-diphenyl-7-{[3-(4-methoxyphenyl)propionyl]amino}heptyl}spiro[naphthalene-2(1H),2'-pyrrolidine] Hydrochloride

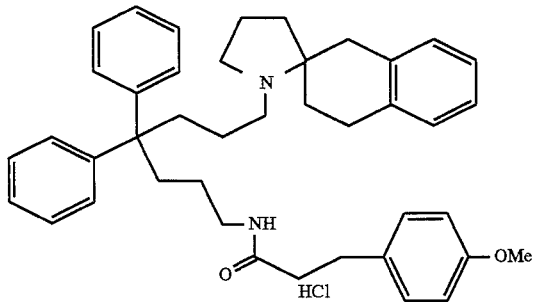

¹H-NMR (CDCl₃, δ): 1.00–1.30(4H,m), 1.40–2.25(8H, m), 2.26–2.90(12H,m), 3.13(2H,q), 3.73(3H,s), 5.12(1H,br t), 6.79(2H,d), 7.00–7.30(16H,m).

Example IV-13

3,4-Dihydro-6-methoxy-1'-{4,4-diphenyl-7-{[3-(4-methoxyphenyl)propionyl]amino}heptyl}spiro[naphthalene-2(1H),2'-piperidine] Dihydrochloride

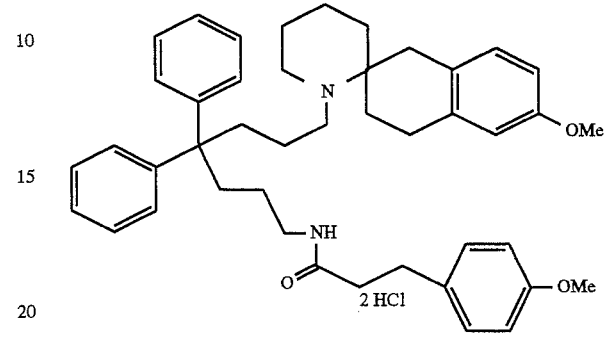

¹H-NMR (CDCl₃, δ): 0.98–1.23(4H,m), 1.30–2.20(14H, m), 2.22–2.78(8H,m), 2.86(2H,t), 3.13(2H,q), 3.73,3.76(3H each,s), 5.10–5.28(1H,br), 6.60–6.73(2H,m), 6.78(2H,d), 6.94(1H,d), 7.02–7.29(14H,m).

Example IV-14

6-Ethoxy-3,4-dihydro-1'-{4,4-diphenyl-7-{[3-(4-methoxyphenyl)propionyl]amino}heptyl}spiro[naphthalene-2(1H),2'-piperidine] Hydrochloride

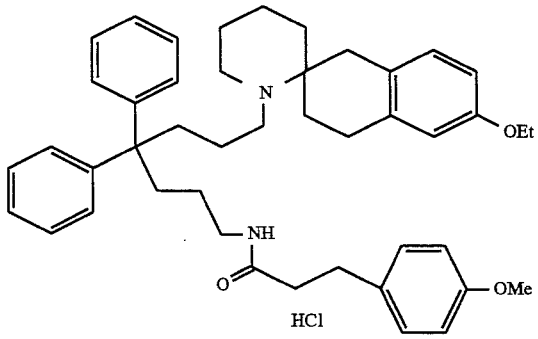

¹H-NMR (CDCl₃, δ): 1.02–1.23(5H,m), 1.33–1.54(9H, m), 1.95–2.11(5H,m), 2.28–2.43(4H,m), 2.43–2.56(2H,m), 2.65–2.80(4H,m), 2.80–2.92(2H,m), 3.07–3.20(2H,m), 3.74 (3H,s), 3.99(2H,q), 5.24(1H,br), 6.63(1H,s), 6.66(1H,d), 6.79(2H,d), 6.94(1H,d), 7.06–7.30(12H,m).

Example IV-15

3,4-Dihydro-6,7-dimethoxy-1'-{4,4-diphenyl-7-{[3-(4-dimethylaminophenyl)propionyl]amino}heptyl}spiro[naphthalene-2(1H),2'-piperidine] Hydrochloride

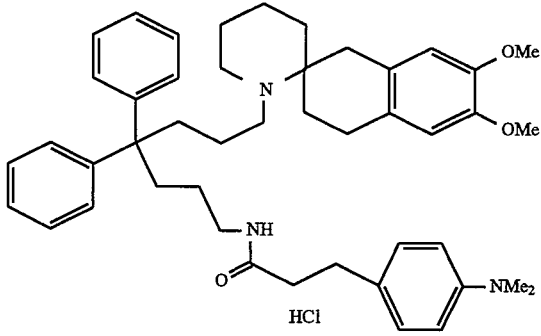

¹H-NMR (CDCl₃, δ): 0.95–1.20(4H,m), 1.32–2.16(14H,m), 2.19–2.95(12H,m), 3.12(2H,q), 3.44(2H,s), 3.83,3.84 (3H each,s), 5.20–5.34(1H,br), 6.55,6.57(1H each,s), 6.58 (1H,d), 7.02–7.26(12H,m).

Example IV-16

3,4-Dihydro-6,7-dimethoxy-1'-{4,4-diphenyl-7-{[3-(4-fluorophenyl)propionyl]amino}heptyl}spiro[naphthalene-2(1H),2'-piperidine] Hydrochloride

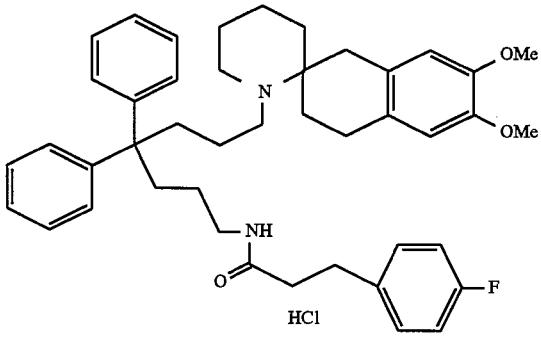

¹H-NMR (CDCl₃, δ): 1.00–1.20(4H,m), 1.30–2.10(12H,m), 2.15–3.00(12H,m), 3.13(2H,q), 3.82,3.84(3H each,s), 5.12–5.24(1H,br), 6.55,6.57(1H each,s), 6.88–7.30(14H,m)

Example IV-17

3,4-Dihydro-6,7-dimethoxy-1'-{7-{[3-(4-chlorophenyl)propionyl]amino}-4,4-diphenylheptyl}spiro[naphthalene-2(1H),2'-piperidine] Hydrochloride

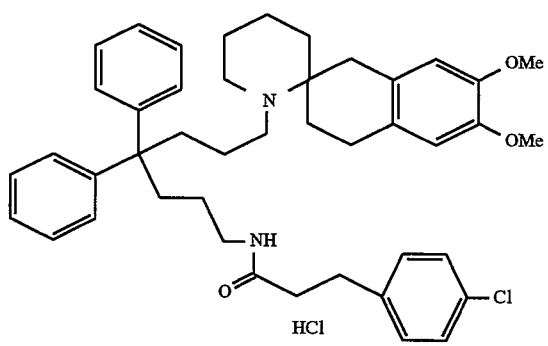

¹H-NMR (CDCl₃, δ): 1.00–1.22(4H,m), 1.35–2.15(12H,m), 2.16–2.81(10H,m), 2.89(2H,t), 3.13(2H,q), 3.82,3.84 (3H each,s), 5.23(1H,br t), 6.55,6.58(1H each,s), 7.00–7.30 (14H,m).

Example IV-18

3,4-Dihydro-6,7-dimethoxy-1'-{7-{[3-(3,5-difluorophenyl)propionyl]amino}-4,4-diphenylheptyl}spiro[naphthalene-2(1H),2'-piperidine] Hydrochloride

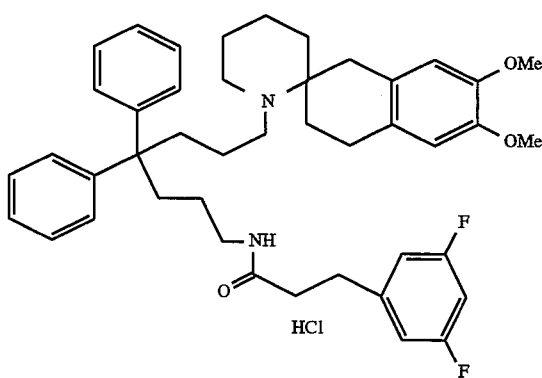

¹H-NMR (CDCl₃, δ): 0.97–1.22(4H,m), 1.33–2.15(12H,m), 2.20–2.80(10H,m), 2.91(2H,t), 3.12(2H,q), 3.82,3.84 (3H each,s), 5.15–5.30(1H,br), 6.55,6.57(1H each,s), 6.66–6.80(2H,m), 7.09–7.30(11H,m).

Example IV-19

3,4-Dihydro-6,7-dimethoxy-1'-{4,4-diphenyl-7-{[3-(4-pyridyl)propionyl]amino}heptyl}spiro[naphthalene-2(1H),2'-piperidine] Dihydrochloride

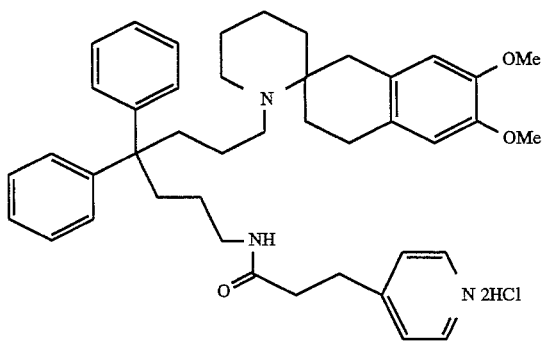

$^1$H-NMR (CDCl$_3$, δ): 1.00–1.25(4H,m), 1.33–1.73(6H,m), 1.73–2.18(6H,m), 2.20–2.81(8H,m), 2.39,2.93(2H each, t), 3.15(2H,q), 3.83,3.84(3H each,s), 5.28(1H,br t), 6.55, 6.58(1H each,s), 7.08–7.30(12H,m), 8.46(2H,dd).

Example IV-20

3,4-Dihydro-6,7-dimethoxy-1'-{4,4-diphenyl-7-{[2-(5-methoxyindan)carbonyl]amino}heptyl}spiro[naphthalene-2(1H),2'-piperidine] Hydrochloride

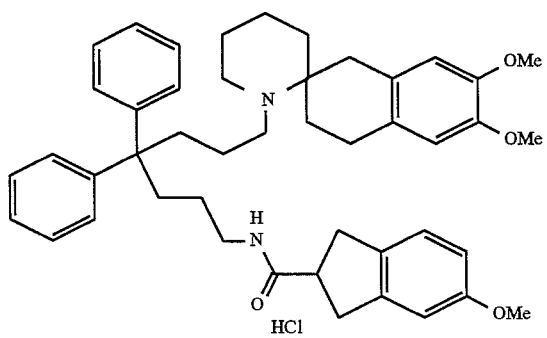

$^1$H-NMR (CDCl$_3$, δ): 1.02–1.30(4H,m), 1.40–2.80(20H,m), 3.02–3.17(5H,m), 3.20(2H,q), 3.76,3.82,3.84(3H each, s), 5.33(1H,br t), 6.54,6.57(1H each,s), 6.70(1H,dd), 6.74(1H,d), 7.07(1H,d), 7.10–7.30(10H,m).

Example IV-21

3,4-Dihydro-6,7-dimethoxy-1'-{4,4-diphenyl-7-{[3-(3,4-methylenedioxyphenyl)propionyl]amino}heptyl}spiro[naphthalene-2(1H),2'-piperidine] Hydrochloride

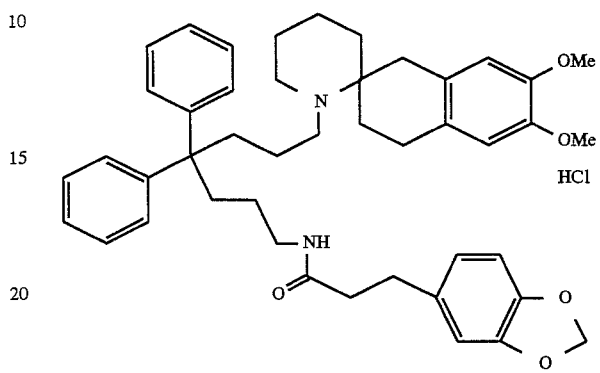

$^1$H-NMR (CDCl$_3$, δ): 1.00–1.20(4H,m), 1.35–2.89(24H,m), 3.14(2H,q), 3.82,3.84(3H each,s), 5.28(1H,br t), 5.87(2H,s), 6.54–6.70(5H,m), 7.00–7.30(10H,m).

Example IV-22

3,4-Dihydro-6,7-dimethoxy-1'-{4,4-diphenyl-7-{[3-(4-methoxyphenyl)propionyl]amino}heptyl}spiro[naphthalene-2(1H),2'-piperidine]-1-one Hydrochloride

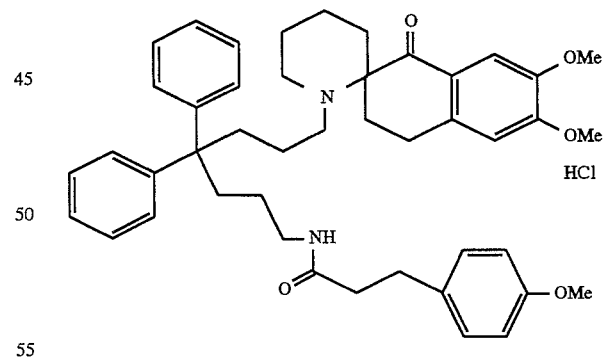

$^1$H-NMR (CDCl$_3$, δ): 1.01–1.26(2H,m), 1.40–1.60(2H,m), 1.60–1.73(4H,br s), 1.80–2.45(14H,m), 2.76–3.02(4H,m), 3.05–3.21(2H,m), 3.73,3.89,3.91(3H each,s), 5.38(1H,br t), 6.61(1H,s), 6.78(1H,d), 7.00–7.26(12H,m), 7.49(1H,s).

Example IV-23

3,4-Dihydro-6-methoxy-5-nitro-1'-{4,4-diphenyl-7-{[3-(4-methoxyphenyl)propionyl]amino}heptyl}spiro[naphthalene-2(1H),2'-piperidine] Hydrochloride

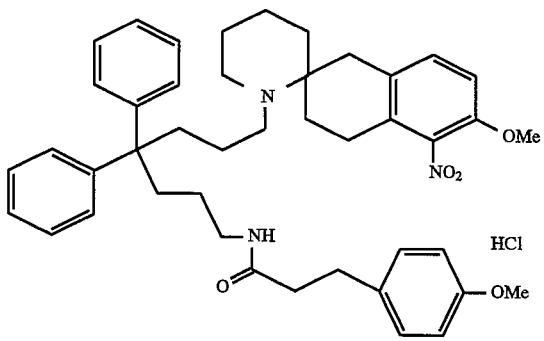

$^1$H-NMR (CDCl$_3$, δ): 1.02–1.32(5H,m), 1.39–1.61(4H,m), 1.73–1.93(2H,m), 1.33–2.20(5H,m), 2.28–2.50(6H,m), 2.50–2.77(4H,m), 2.78–2.99(2H,m), 3.03–3.24(2H,m), 3.73,3.84(3H each,s), 5.39(1H,br), 6.72–6.88(3H,m), 7.02–7.33(13H,m).

Example IV-24

3,4-Dihydro-6-methoxy-7-nitro-1'-{4,4-diphenyl-7-{[3-(4-methoxyphenyl)propionyl]amino}heptyl}spiro[naphthalene-2(1H),2'-piperidine] Hydrochloride

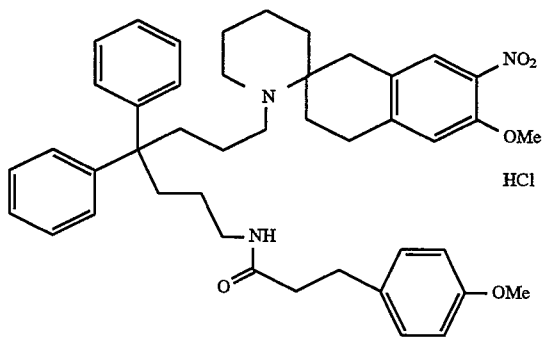

$^1$H-NMR (CDCl$_3$, δ): 1.01–1.20(5H,m), 1.32–1.73(6H,m), 1.82–2.18(5H,m), 2.22–2.51(6H,m), 2.52–2.76(2H,m), 2.76–2.94(4H,m), 3.06–3.20(2H,m), 3.74,3.90(3H each,s), 5.16(1H,br), 6.78(1H,s), 6.79(2H,d), 7.04–7.31(12H,m), 7.61(1H,s).

Example IV-25

7-Amino-3,4-dihydro-6-methoxy-1'-{4,4-diphenyl-7-{[3-(4-methoxyphenyl)propionyl]amino}heptyl}spiro[naphthalene-2(1H),2'-piperidine] Dihydrochloride

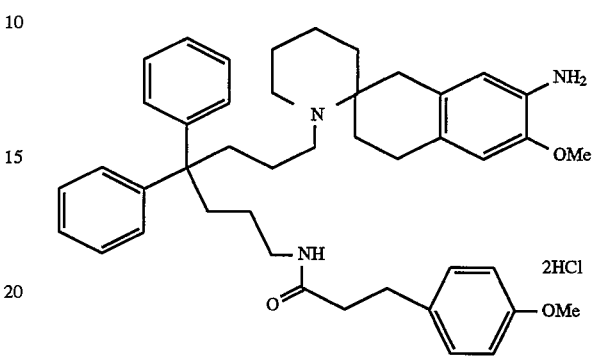

$^1$H-NMR (CDCl$_3$, δ): 0.80–1.20(5H,m), 1.37–1.87(6H,m), 1.92–2.11(5H,m), 2.22–2.56(6H,m), 2.58–2.76(4H,m), 2.78–2.92(2H,m), 3.04–3.12(2H,m), 3.72,3.78(3H each,s), 5.34(1H,br), 6.40,6.49(1H each,s), 6.78(2H,d), 7.03–7.28(12H,m),

Example IV-26

7-Acetylamino-3,4-dihydro-6-methoxy-1'-{4,4-diphenyl-7-{[3-(4-methoxyphenyl)propionyl]amino}heptyl}spiro[naphthalene-2(1H),2'-piperidine] Hydrochloride

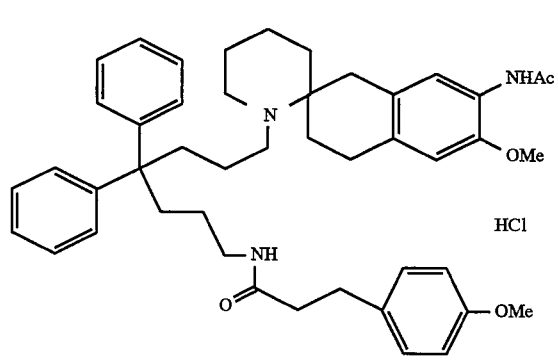

$^1$H-NMR (CDCl$_3$, δ): 1.00–1.23(5H,m), 1.38–1.90(6H,m), 1.91–2.12(5H,m), 2.22(3H,s), 2.24–2.52(6H,m), 2.60–2.76(4H,m), 2.76–2.92(2H,m), 3.07–3.20(2H,m), 3.73,3.83(3H each,s), 5.55(1H,br), 6.58(1H,s), 6.78(2H,d), 7.04–7.28(12H,m), 7.69(1H,s), 8.06(1H,s).

Example IV-27

7-Acetyl-3,4-dihydro-6-methoxy-1'-{4,4-diphenyl-7-{[3-(4-methoxyphenyl)propionyl]amino}heptyl}spiro[naphthalene-2(1H),2'-piperidine] Hydrochloride

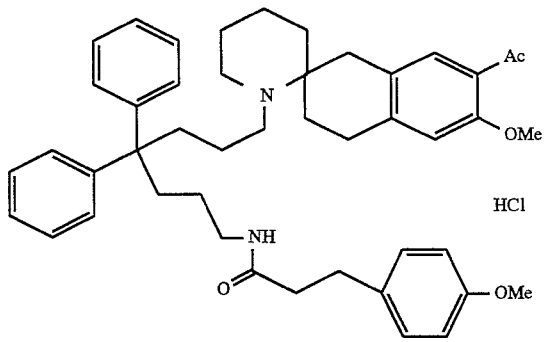

$^1$H-NMR (CDCl$_3$, δ): 1.01–1.24(5H,m), 1.35–1.90(6H, m), 1.91–2.19(5H,m), 2.24–2.53(6H,m), 2.58(3H,s), 2.62–2.96(6H,m), 3.05–3.20(2H,m), 3.72.3.86(3H each,s), 5.67(1H,br), 6.68(1H,s), 6.78(2H,d), 7.05–7.27(12H,m), 7.47(1H,s).

Example IV-28

3,4-Dihydro-6,7-methylenedioxy-1'-{4,4-diphenyl-7-{[3-(4-methoxyphenyl)propionyl]amino}heptyl}spiro[naphthalene-2(1H),2'-piperidine] Hydrochloride

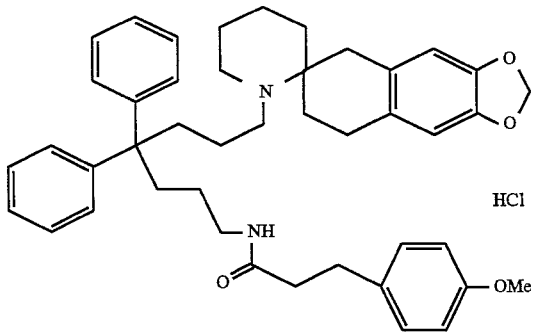

$^1$H-NMR (CDCl$_3$, δ): 1.02–1.30(5H,m), 1.38–1.88(6H, m), 1.89–2.20(5H,m), 2.28–2.45(4H,m), 2.46–2.56(2H,m), 2.56–2.75(4H,m), 2.75–2.98(2H,m), 3.03–3.23(2H,m), 3.73 (3H,s), 5.58(1H,br), 5.86(2H,s), 6.51(1H,s), 6.55(1H,s), 6.79(2H,d), 7.02–7.32(12H,m).

Example IV-29

6,7-Diethoxy-3,4-dihydro-1'-{4,4-diphenyl-7-{[3-(4-methoxyphenyl)propionyl]amino}heptyl}spiro[naphthalene-2(1H),2'-piperidine] Hydrochloride

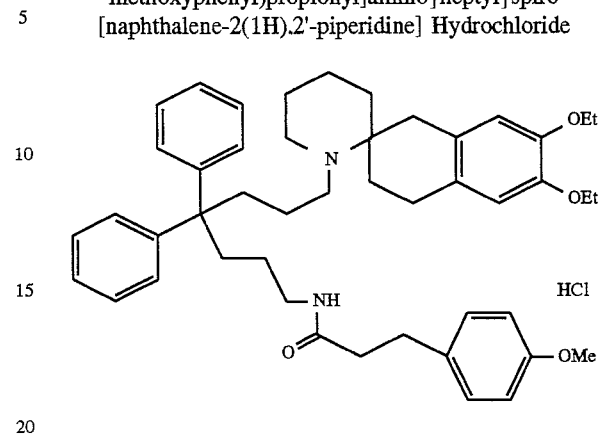

$^1$H-NMR (CDCl$_3$, δ): 1.00–1.30(5H,m), 1.30–1.60(10H, m), 1.60–1.90(2H,m), 1.90–2.19(5H,m), 2.26–2.44(4H,m), 2.44–2.58(2H,m), 2.58–2.78(4H,m), 2.78–2.93(2H,m), 3.03–3.20(2H,m), 3.72(3H,s), 3.90–4.12(4H,m), 5.55(1H, br), 6.56,6.58(1H each,s), 6.78(2H,d), 7.03–7.30(12H,m).

Example IV-30

3,4-Dihydro-1'-{4,4-diphenyl-7-{[3-(4-methoxyphenyl)propionyl]amino}heptyl}spiro[naphthalene-2(1H),2'-hexamethyleneimine] Hydrochloride

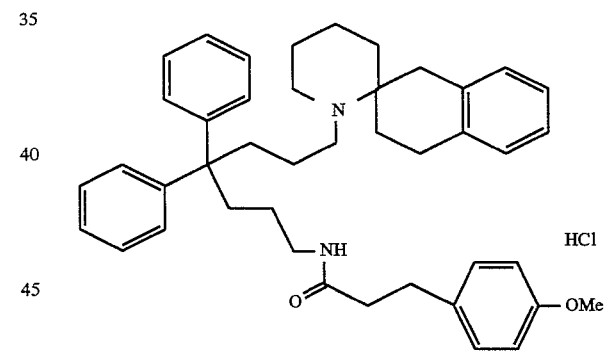

$^1$H-NMR (CDCl$_3$, δ): 0.85–2.20(20H,m), 2.20–2.91(10H, m), 3.14(2H,q), 3.72(3H,s), 5.07(1H,br t), 6.78(2H,d), 7.00–7.30(16H,m).

Example IV-31

(+)-3,4-Dihydro-6-methoxy-1'-{4,4-diphenyl-7-{[(4-methoxyphenyl)acetyl]amino}heptyl}spiro-[naphthalene-2(1H),2'-piperidine] Hydrochloride

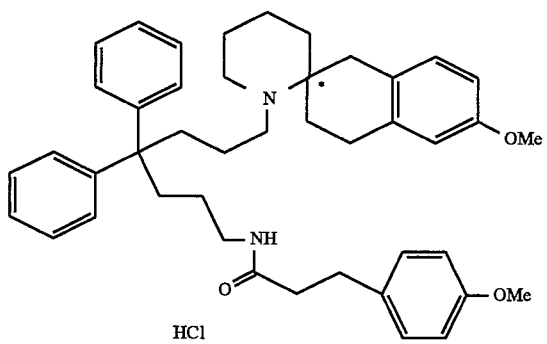

$^1$H-NMR (CDCl$_3$, δ): 0.98–1.22(4H,m), 1.30–2.20(14H, m), 2.20–2.78(8H,m), 2.86(2H,t), 3.13(2H,q), 3.72,3.76(3H each,s), 5.12–5.30(1H,br), 6.59–6.73(2H,m), 6.78(2H,d), 6.94(1H,d), 7.02–7.29(14H,m).

$[α]_D$=+3.4° (c 0.893 in MeOH)

Example IV-32

(−)-3,4-Dihydro-6-methoxy-1'-{4,4-diphenyl-7-{[(4-methoxyphenyl)acetyl]amino}heptyl}spiro-[naphthalene-2(1H),2'-piperidine] Hydrochloride

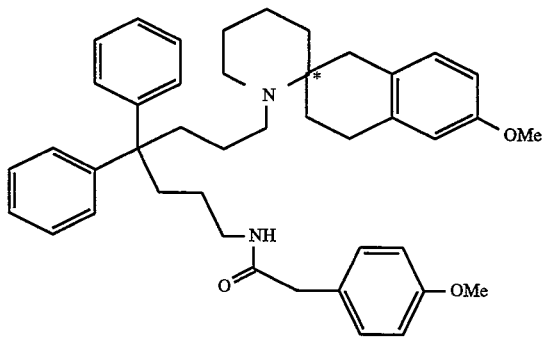

$^1$H-NMR (CDCl$_3$, δ): 0.98–1.22(4H,m), 1.30–2.20(14H, m), 2.20–2.78(8H,m), 2.86(2H,t), 3.13(2H,q), 3.72,3.76(3H each,s), 5.12–5.30(1H,br), 6.59–6.73(2H,m), 6.78(2H,d), 6.94(1H,d), 7.02–7.29(14H,m).

$[α]_D$=−2.8° (c 0.828 in MeOH)

Example IV-33

(−)3,4-Dihydro-6,7-dimethoxy-1'-{4,4-diphenyl-7-{[(4-methoxyphenyl)acetyl]amino}heptyl}spiro[naphthalene-2(1H),2'-piperidine]-1-one Hydrochloride

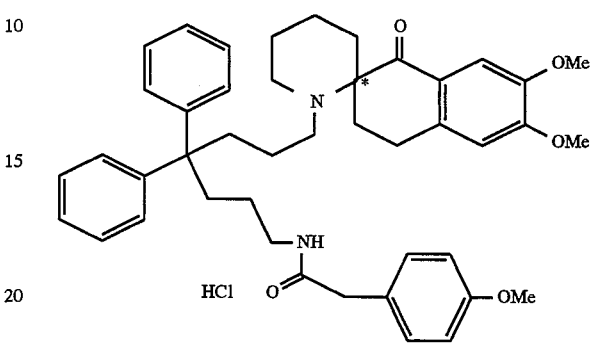

$^1$H-NMR (CDCl$_3$, δ): 1.00–1.25(4H,m), 1.35–2.52(18H, m), 2.75–2.95(4H,m), 3.15(2H,q), 3.73,3.89,3.92(3H each, s), 5.38(1H,br t), 6.61(1H,s), 6.78(2H,d), 7.05–7.27(12H, m), 7.50(1H,s).

$[α]_D$=−9.7° (c 0.624 in MeOH)

Example IV-34

(−)-3,4-Dihydro-6,7-dimethoxy-1'-{4,4-diphenyl-7-{[(4-fluorophenyl)acetyl]amino}heptyl}spiro[naphthalene-2(1H),2'-piperidine] Hydrochloride

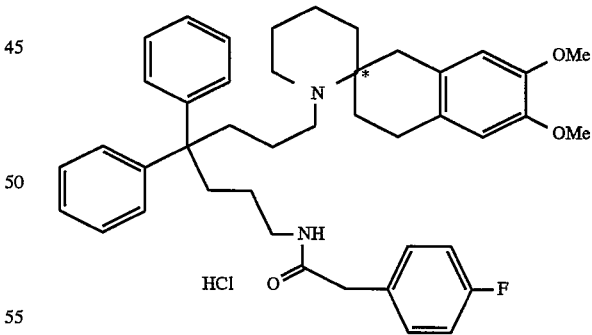

$^1$H-NMR (CDCl$_3$, δ): 1.02–1.30(5H,m), 1.36–1.61(4H, m), 1.61–1.90(2H,m), 1.90–2.18(8H,m), 2.23–2.47(2H,m), 2.47–2.60(2H,m), 2.60–2.80(4H,m), 3.06–3.22(2H,m), 3.47 (2H,s), 3.82,3.83(3H each,s), 5.68(1H,br), 6.55,6.58(1H each,s), 6.94–7.30(14H,m).

$[α]_D$=−3.4° (C 0.327 in MeOH)

Example IV-35

(+)-3,4-Dihydro-6,7-dimethoxy-1'-{4,4-diphenyl-7-{[(4-fluorophenyl)acetyl]amino}heptyl}spiro[naphthalene-2(1H),2'-piperidine] Hydrochloride

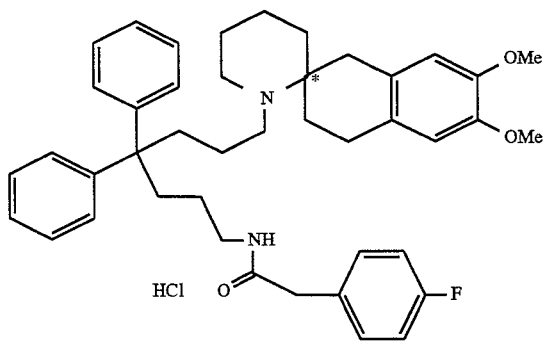

$^1$H-NMR (CDCl$_3$, δ): 1.02–1.30(5H,m), 1.36–1.61(4H,m), 1.61–1.90 (2H,m), 1.90–2.18(5H,m), 2.23–2.47(2H,m), 2.47–2.60 (2H,m), 2.60–2.80(4H,m), 3.06–3.22(2H,m), 3.47(2H,s), 3.82,3.83(3H each,s), 5.68(1H,br), 6.55,6.58(1H each,s), 6.94–7.30(14H,m).

[α]$_D$=+3.8° (c 0.330 in MeOH)

Example IV-36

(−)-3,4-Dihydro-6,7-dimethoxy-1'-{4,4-diphenyl-7-{[3-(4-fluorophenyl)propionyl]amino}heptyl}spiro[naphthalene-2(1H),2'-piperidine] Hydrochloride

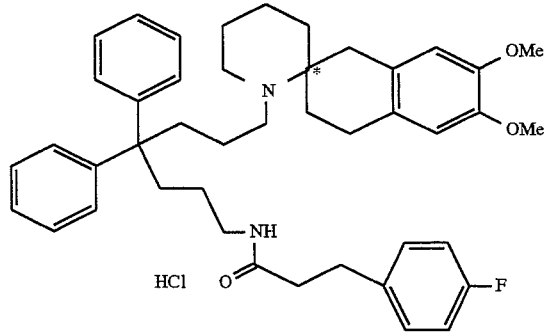

$^1$H-NMR (CDCl$_3$, δ): 1.02–1.30(5H,m), 1.37–1.90(6H,m), 1.91–2.18(5H,m), 2.28–2.46(4H,m), 2.48–2.59(2H,m), 2.59–2.80(4H,m), 2.80–2.97(2H,m), 3.04–3.20(2H,m), 3.82,3.83(3H each,s), 5.53(1H,br), 6.55,6.57(1H each,s), 6.92(2H,t), 7.07–7.31(12H,m).

Example IV-37

(+)-3,4-Dihydro-6,7-dimethoxy-1'-{4,4-diphenyl-7-{[3-(4-fluorophenyl)propionyl]amino}heptyl}spiro[naphthalene-2(1H),2'-piperidine] Hydrochloride

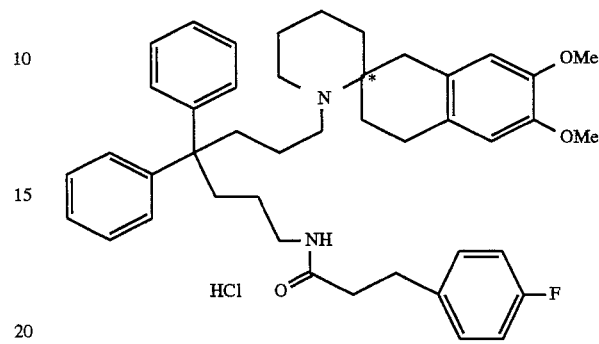

$^1$H-NMR (CDCl$_3$, δ): 1.02–1.30(5H,m), 1.37–1.90(6H,m), 1.91–2.18(5H,m), 2.28–2.46(4H,m), 2.48–2.59(2H,m), 2.59–2.80(4H,m), 2.80–2.97(2H,m), 3.04–3.20(2H,m), 3.82,3.83(3H each,s), 5.53(1H,br), 6.55,6.57(1H each,s), 6.92(2H,t), 7.07–7.31(12H,m).

[α]$_D$=+1.98° (c 0.514 in MeOH)

Example IV-38

(+)-3,4-Dihydro-6,7-dimethoxy-1'-{7-{[3-(4-chlorophenyl)propionyl]amino}-4,4-diphenylheptyl}spiro[naphthalene-2(1H),2'-piperidine] Hydrochloride

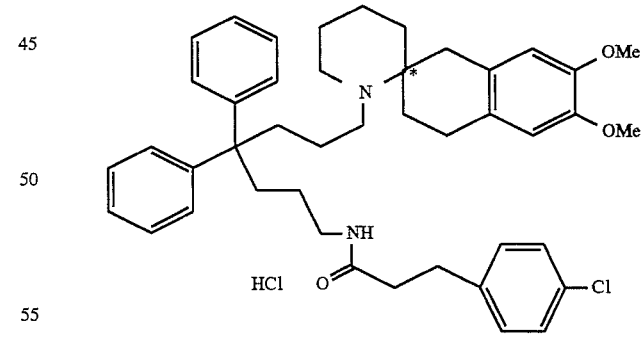

$^1$H-NMR (CDCl$_3$, δ): 1.03–1.34(5H,m), 1.40–1.90(6H,m), 1.91–2.20(5H,m), 2.32–2.48(4H,m), 2.50–2.62(2H,m), 2.62–2.82(4H,m), 2.82–2.97(2H,m), 3.04–3.20(2H,m), 3.82(6H,s), 5.74(1H,br), 6.54,6.56(1H each,s), 7.04–7.30(14H,m).

[α]$_D$=+0.20° (c 0.04 in MeOH)

Example IV-39

(−)-3,4-Dihydro-6,7-dimethoxy-1'-{7-{[3-(4-chlorophenyl)propionyl]amino}-4,4-diphenylheptyl}spiro[naphthalene-2(1H),2'-piperidine] Hydrochloride

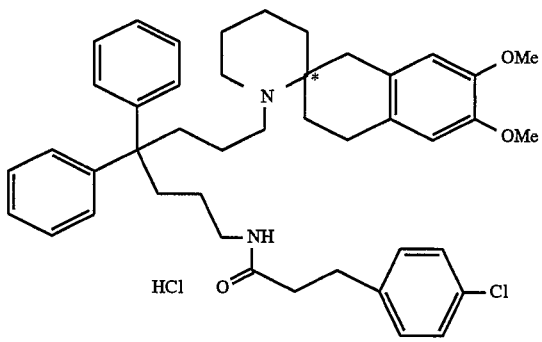

$^1$H-NMR (CDCl$_3$, δ): 1.03–1.34(5H,m), 1.40–1.90(6H, m), 1.91–2.20(5H,m), 2.32–2.48(4H,m), 2.50–2.62(2H,m), 2.62–2.82(4H,m), 2.82–2.97(2H,m), 3.04–3.20(2H,m), 3.82 (6H,s), 5.74(1H,br), 6.54,6.56(1H each,s), 7.04–7.30(14H, m).

Example IV-40

(−)-3,4-Dihydro-6,7-dimethoxy-1'-{4,4-diphenyl-7-{[3-(4-methoxyphenyl)propionyl]amino}heptyl}spiro[naphthalene-2(1H),2'-piperidine] Hydrochloride

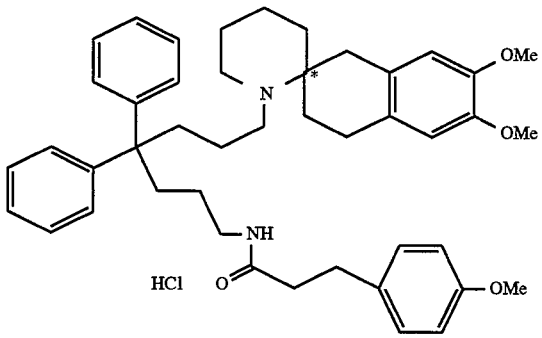

$^1$H-NMR (CDCl$_3$, δ): 1.00–1.22(4H,m), 1.32–2.15(12H, m), 2.17–2.92(12H,m), 3.14(2H,q), 3.73,3.83,3.84(3H each, s), 5.19(1H,br s), 6.56,6.58(1H each,s), 6.79(2H,d), 7.04–7.30(12H,m).

[α]$_D$=−3.31° (C 0.651 in MeOH)

Example IV-41

(+)-3,4-Dihydro-6,7-dimethoxy-1'-{4,4-diphenyl-7-{[3-(4-methoxyphenyl)propionyl]amino}heptyl}spiro[naphthalene-2(1H),2'-piperidine] Hydrochloride

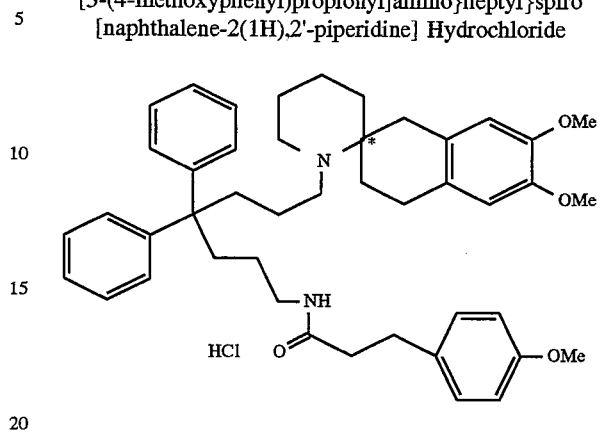

$^1$H-NMR (CDCl$_3$, δ): 1.00–1.22(4H,m), 1.32–2.15(12H, m), 2.17–2.92(12H,m), 3.14(2H,q), 3.73,3.83,3.84(3H each, s), 5.19(1H,br s), 6.56,6.58(1H each,s), 6.79(2H,d), 7.04–7.30(12H,m).

[α]$_D$=+3.50° (C 0.712 in MeOH)

Example IV-42

3,4-Dihydro-4'-{4,4-diphenyl-7-{[3-(4-methoxyphenyl)propionyl]amino}heptyl}spiro[naphthalene-2(1H),3'-morpholine] Hydrochloride

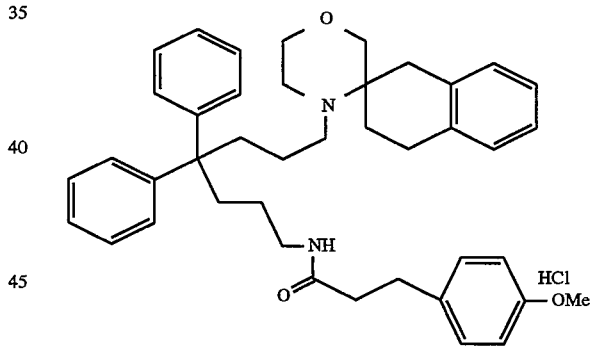

$^1$H-NMR (CDCl$_3$, δ): 1.00–1.30(4H,m), 1.58–2.50(12H, m), 2.58–3.00(6H,m), 3.13(2H,q), 3.45–3.80(7H,m), 5.08–5.20(1H,br), 6.78(2H,d), 7.00–7.33(16H,m).

Example IV-43

3,4-Dihydro-7-methoxy-4'-{4,4-diphenyl-7-{[3-(4-methoxyphenyl)propionyl]amino}heptyl}spiro[naphthalene-2(1H),3'-morpholine] Hydrochloride

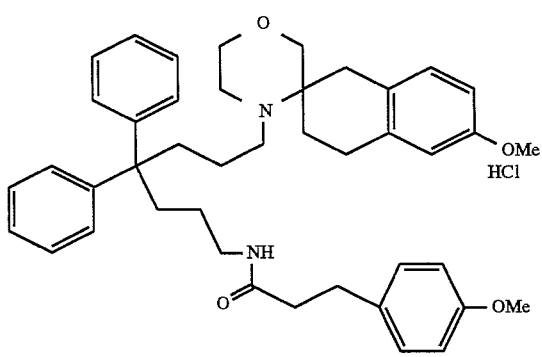

$^1$H-NMR (CDCl$_3$, δ): 1.00–1.30(4H,m), 1.60–1.80(2H,m), 1.97–2.50(10H,m), 2.60–2.92(6H,m), 3.13(2H,q), 3.48–3.70(4H,m), 3.73,3.77(3H,each,s), 5.08–5.20(1H,br t), 6.60–6.73(1H,m), 6.78(2H,d), 6.94–7.30(14H,m).

Example IV-44

3,4-Dihydro-6,7-dimethoxy-4'-{4,4-diphenyl-7-{[3-(4-methoxyphenyl)propionyl]amino}heptyl}spiro[naphthalene-2(1H),3'-morpholine] Hydrochloride

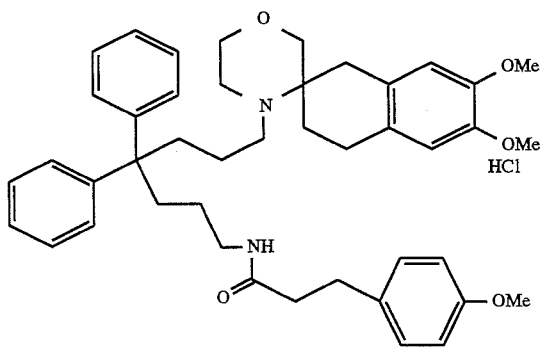

$^1$H-NMR (CDCl$_3$, δ): 1.00–1.28(4H,m), 1.58–1.90(2H,m), 1.92–2.55(10H,m), 2.60–2.80(4H,m), 2.86(2H,t), 3.13(2H,q), 3.48–3.70(4H,m), 3.73(3H,s), 3.83(6H,s), 5.08–5.20(1H,br), 6.57,6.59(1H each,s), 6.78(2H,d), 7.05–7.30(12H,m).

Example IV-45

3,4-Dihydro-6,7-dimethoxy-4'-methyl-1'-{4,4-diphenyl-7-{[3-(4-methoxyphenyl)propionyl]amino}heptyl}spiro[naphthalene-2(1H),2'-piperazine] Dihydrochloride

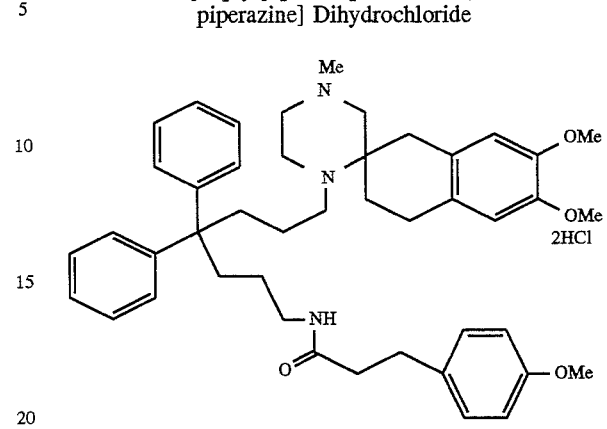

$^1$H-NMR (CDCl$_3$, δ): 1.00–1.25(4H,m), 1.60–2.80(23H,m), 2.87(2H,m), 3.15(2H,q), 3.73(3H,s), 3.84(6H,s), 5.00–5.25(1H,br), 6.50–6.65(2H,m), 6.79(2H,d), 7.05–7.33 (12H,m).

| Formulation Example 1 | |
|---|---|
| (1) Compound of Example II-45 | 10.0 g |
| (2) Lactose | 60.0 g |
| (3) Corn starch | 35.0 g |
| (4) Gelatin | 3.0 g |
| (5) Magnesium stearate | 2.0 g |

Using 30 ml of an aqueous solution of gelatin (10 wt. % concentration, 3.0 g as gelatin), a mixture of 10.0 g of the compound obtained in Example II-45, 60.0 g of lactose, and 35.0 g of corn starch was granulated by means of a 1 mm-mesh sieve, dried at 40° C., and re-sieved. The granules thus prepared were mixed with 2.0 g of magnesium stearate and the mixture was compressed. The core tablets thus obtained were coated using an aqueous suspension containing sucrose, titanium dioxide, talc and gum arabic. The coated tablets were then glazed with beeswax to provide 1000 finished tablets.

| Formulation Example 2 | |
|---|---|
| (1) Compound of Example II-45 | 10.0 g |
| (2) Lactose | 70.0 g |
| (3) Corn starch | 50.0 g |
| (4) Soluble starch | 7.0 g |
| (5) Magnesium stearate | 3.0 g |

Using 70 ml of aqueous starch solution (7.0 g as soluble starch), a mixture of 10.0 g of the compound obtained in Example II-45 and 3.0 g of magnesium stearate was granulated, dried, and mixed with 70.0 g of lactose and 50.0 g of corn starch. The whole mixture was then compressed to provide 1000 tablets.

Test Example (A) Preparation of $^{125}$I-leuprolerin

A tube was filled with 10 μl of an aqueous solution of leuprolerin (3×10$^4$M) and lactoperoxidase (0.01 mg/ml)

followed by addition of 10 μl of Na$^{125}$I solution (37 MBq). After stirring, 10 μl of 0.001% H$_2$O$_2$ was added and the reaction was conducted at room temperature for 20 minutes. The reaction was stopped by adding 700 μl of 0.05% TFA and the reaction mixture was subjected to reversed-phase HPLC under the conditions set forth below. $^{125}$I-leuprolerin was eluted with a retention time of 26–27 minutes.

Column: TSK Gel ODS-80™ CTR (4.6 mm×10 cm)
Eluent: Solvent A (0.05% TFA) and solvent B (40% CH$_3$CN-0.05% TFA)
Gradient: 0 min (100% solvent A)–3 min (100% solvent A)–7 min (50% solvent A+50% solvent B)–40 min (100% solvent B)
Elution temperature: room temperature
Flow rate: 1 ml/min.

(B) Preparation of a Rat GnRH Receptor-containing Anterior Pituitary Membrane Fraction Forty rats (8 weeks old, male) of Wistar strain were decapitated under no anesthesia and the anterior pituitary isolated from each animal was washed with an ice-cooled homogenate buffer (25 mM Tris (tris(hydroxylmethyl) aminomethane)-HCl, 0.3M sucrose, 1 mM EGTA (ethylene-bis(oxyethylenenitrilo)tetraacetic acid), 0.25 mM PMSF (phenylmethylsulfonyl fluoride), 10 U/ml aprotinin, 1 μg/ml pepstatin, 20 μg/ml leupeptin, 100 μg/ml phosphoramidon, 0.03% sodium azide; pH 7.5). The anterior pituitary was suspended in 2 ml of the same homogenate buffer as above and homogenized using a Polytron homogenizer. The homogenate thus prepared was centrifuged at 700 xg for 15 minutes and the supernatant was transferred to an ultracentrifuge cuvette and further centrifuged at 100,000 xg for 1 hour to provide a membrane fraction pellet. This pellet was suspended in 2 ml of an assay buffer (25 mM Tris-HCl, 1 mM ethylenediaminetetraacetic acid (EDTA), 0.1% bovine serum albumin (BSA), 0.25 mM PMSF, 1 μg/ml pepstatin, 20 μg/ml leupeptin, 100 μg/ml phosphoramidon, 0.03% sodium azide; pH 7.5) and centrifuged at 100,000 xg for 1 hour. The membrane fraction recovered as a pellet was resuspended in 10 ml of the same assay buffer as above, distributed into vials, preserved at –80° C., and reconstituted before use.

(C) Preparation of a Bovine GnRH Receptor-containing Anterior Pituitary Membrane Fraction A bovine GnRH receptor-containing anterior pituitary membrane fraction was prepared in the same manner as (B) except that the supernatant from the 10,000 xg centrifugate was centrifuged at 100,000 xg for 1 hour to provide a membrane fraction pellet.

(D) Preparation of a Human GnRH Receptor-containing CHO (Chinese Hamster Ovarian) Cell Membrane Fraction Human GnRH receptor-expressed CHO cells (10$^9$ cells) were suspended in phosphate buffered saline supplemented with EDTA (PBS-EDTA) and centrifuged at 100 xg for 5 minutes. To the sediment was added 10 ml of a cell homogenate buffer (10 mM NaHCO$_3$, 5 mM EDTA, pH 7.5) and the mixture was homogenized using a Polytron homogenizer. The homogenate was centrifuged at 400 xg for 15 minutes and the supernatant was transferred to an ultracentrifuge cuvette and centrifuged at 100,000 xg for 1 hour to prepare a membrane fraction pellet. This pellet was suspended in 2 ml of the assay buffer and further centrifuged at 100,000 xg for 1 hour. The membrane fraction recovered as a pellet was resuspended in 20 ml of the assay buffer, distributed into vials, preserved at –80° C., and reconstituted before use.

(E) Determination of the $^{125}$I-leuprolerin Binding Inhibition Rate

The rat and human membrane fractions prepared under (B) and (D) were respectively diluted with the assay buffer to make 200 μg/ml each and 188 μl aliquots of each dilution were distributed into tubes. The bovine membrane fraction prepared under (C) was diluted with the assay buffer to make 750 μg/ml and 188 μl aliquots of the dilution were distributed into tubes. When the rat anterior pituitary membrane fraction was used, 2 μl of 0.1 mM compound/60% dimethyl sulfoxide (DMSO) and 10 μl of 38 nM $^{125}$I-leuprolerin were concurrently added. When the bovine anterior pituitary membrane fraction and the human GnRH receptor-expressed CHO cell membrane fraction were used, 2 μl of 2 mM compound/60% DMSO and 10 μl of 38 nM $^{125}$I-leuprolerin were concurrently added. For determination of maximum binding, a reaction mixture was prepared by adding 2 μl of 60% DMSO and 10 μl of 38 nM $^{125}$I-leuprolerin. For determination of non-specific binding, a reaction mixture was prepared using 2 μl of 100 μM leuprolerin/60% DMSO and 10 μl of 3.8 nM $^{125}$I-leuprolerin.

When the rat and bovine anterior pituitary membrane fractions were used, each reaction was carried out at 4° C. for 90 minutes. On the other hand, when the human GnRH receptor-expressed CHO cell membrane fraction was used, the reaction was conducted at 25° C. for 60 minutes. After completion of the reaction, the reaction mixture was suction-filtered through a polyethyleneimine-treated Whatman glass filter (GF-F) [trademark;whatman]. After filtration, the radioactivity of the residual $^{125}$I-leuprolerin on the filter was measured using a γ-counter.

The computation formula of (TB-SB)/(TB-NSB)×100 (SB=radioactivity bound in the presence of the test compound, TB=maximum amount of radioactivity bound, NSB=amount of radioactivity nonspecifically bound) was calculated to find the binding inhibition rate for the test compound. Moreover, the inhibition rate was determined by varying the concentration of each test compound and the concentration of the compound causing 50% inhibition of binding (IC$_{50}$ value) was calculated by Hill plot.

The results are shown in Table 30.

TABLE 30

| | GnRH-receptor binding inhibition assay | |
|---|---|---|
| Compound | GnRH-receptor binding inhibitory activity (IC$_{50}$, μM) | |
| of Example | Man | Rat |
| II-37 | | 0.3 |
| 43 | | 0.2 |
| 44 | | 0.4 |
| 45 | | 0.08 |
| 46 | | 0.003 |
| 48 | 0.2 | 0.002 |
| 50 | 0.08 | 0.0007 |
| 51 | 0.08 | 0.002 |
| 53 | 0.8 | 0.01 |
| 58 | 0.11 | 0.0016 |
| 59 | 0.4 | 0.02 |
| 60 | | 0.002 |
| 61 | 0.1 | 0.01 |

TABLE 30-continued

| GnRH-receptor binding inhibition assay | | |
|---|---|---|
| Compound of Example | GnRH-receptor binding inhibitory activity ($IC_{50}$, μM) | |
| | Man | Rat |
| 63 | 0.4 | 0.001 |
| 64 | 0.2 | 0.009 |
| 65 | 0.02 | 0.001 |
| 66 | 0.3 | 0.003 |
| 68 | 0.4 | 0.009 |

It is apparent from the results that compound (I), inclusive of its salt, of this invention has excellent GnRH-receptor binding inhibitory activity.

Compound (I) of this invention, inclusive of its salt, inhibits secretion of gonadotropic hormone in mammalian animals by way of its GnRH-receptor antagonizing activity to control blood steroid hormone levels so that it can be used in the prevention and treatment of various diseases, particularly in man.

While the present invention has been described with respect to what is presently considered to be the preferred embodiments, it is to be understood that the invention is not limited to the disclosed embodiments. The present invention is intended to cover various modifications and equivalent arrangements included within the spirit and scope of the appended claims.

What is claimed is:

1. A compound of the formula:

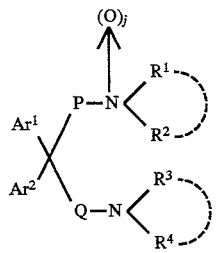

wherein $Ar^1$ and $Ar^2$ independently represent an optionally substituted aromatic group;

P and Q independently represent a divalent aliphatic hydrocarbon group having at least 2 carbon atoms, which may have either oxygen or sulfur within the carbon chain;

$R^1$ and $R^3$ independently represent i) an acyl group of —CO—R or —CONH—R wherein R represents an optionally substituted hydrocarbon group or an optionally substituted heterocyclic group, or ii) an optionally substituted hydrocarbon group;

$R^2$ and $R^4$ independently represent hydrogen or an optionally substituted alkyl group;

$R^1$ and $R^2$ or $R^3$ and $R^4$, taken together with the adjacent nitrogen atom, may form an optionally substituted nitrogen-containing heterocyclic group; and j represents 0 or 1, or a salt thereof.

2. The compound of claim 1 wherein $Ar^1$ and $Ar^2$ are independently $C_{6-14}$ aryl group which may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl, $C_{6-10}$ aryl and $C_{6-10}$ aryloxy;

P and Q are independently divalent $C_{2-6}$ aliphatic hydrocarbon group which may have either oxygen or sulfur within the carbon chain;

$R^1$ and $R^3$ are independently i) an acyl group of —CO—$R^a$ or —CONH—$R^a$ wherein $R^a$ is a) a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group which may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl, $C_{6-10}$ aryl, $C_{6-10}$ aryloxy and 5- or 6-membered heterocyclic group, or b) a 5- to 10-membered heterocyclic group containing, besides carbon atom, 1 to 4 hetero atoms selected from nitrogen atom, oxygen atom and sulfur atom, which may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl, $C_{6-10}$ aryl and $C_{6-10}$ aryloxy, or ii) a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group which may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl and 5- or 6-membered heterocyclic group; and $R^2$ and $R^4$ are independently hydrogen or a $C_{1-6}$ alkyl group which may be substituted by 1 to 5 substituents selected from the group consisting of halogen, nitro, cyano, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl, $C_{6-10}$ aryl and $C_{6-10}$ aryloxy, or $R^1$ and $R^2$ or $R^3$ and $R^4$, taken together with the adjacent nitrogen atom, form a nitrogen-containing heterocyclic group of the formula:

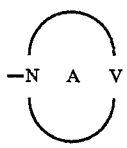  i)

wherein ring A is a 4- to 8-membered ring which may be substituted by hydroxyl or oxo group; and V is >O, >C=O,

or >N—W in which W is a) hydrogen, b) a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group which may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl and 5- or 6-membered heterocyclic group, or c) a 5- to 10-membered heterocyclic group, containing, besides carbon atom, 1 to 4 hetero atoms selected from nitrogen atom, oxygen atom and sulfur atom, which may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl, $C_{6-10}$ aryl and $C_{6-10}$ aryloxy, and $W^a$ is hydrogen or hydroxyl,

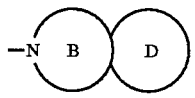  ii)

wherein ring B is a 4- to 12-membered mono- or bicyclic ring optionally having an oxo group and optionally substituted by 1 to 5 $C_{1-6}$ alkyl groups; and ring D is a 4- to 12-membered aromatic ring which may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl, $C_{6-10}$ aryl and $C_{6-10}$ aryloxy, or

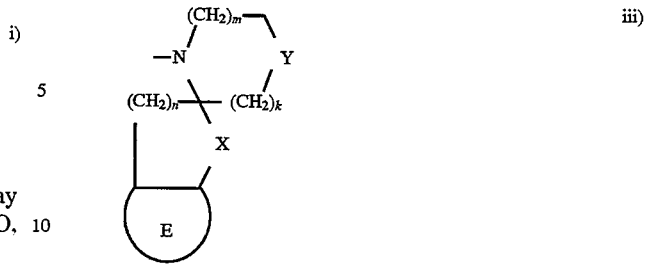  iii)

wherein ring E is a 5- to 10-membered aromatic ring which may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl, $C_{6-10}$ aryl and $C_{6-10}$ aryloxy;

X is —$CH_2$—, —CO— or —CH(OH)—;

Y is —$CH_2$—, —O— or —$NW^b$— in which $W^b$ is hydrogen or a $C_{1-6}$ alkyl group which may be substituted by 1 to 5 substituents selected from the group consisting of halogen, $C_{1-3}$ alkylenedioxy, nitro, cyano, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl, $C_{6-10}$ aryl, $C_{6-10}$ aryloxy and 5- or 6-membered heterocyclic group;

k+m is an integer of 1 to 4; and n is an integer of 1 to 3.

3. The compound of claim 1 wherein $R^1$ is a $C_{7-16}$ aralkyl, $C_{3-6}$ cycloalkyl or benzo-$C_{3-6}$ cycloalkyl group which may be substituted by 1 to 5 substituents selected from the group consisting of halogen, optionally halogenated $C_{1-6}$ alkyl, optionally halogenated $C_{1-6}$ alkoxy and $C_{1-6}$ alkoxy-carbonyl.

4. The compound of claim 1 wherein $R^3$ is an acyl group of —CO—$R^b$ wherein $R^b$ is a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group which may be substituted by 1 to 5 substituents selected from the group consisting of halogen, $C_{1-3}$ alkylenedioxy, nitro, cyano, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl and 5- or 6-membered heterocyclic group.

5. The compound of claim 1 wherein

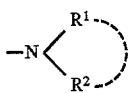

is the formula:

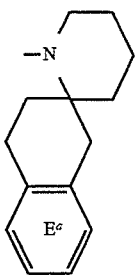

wherein ring $E^a$ is a benzene ring which may be substituted by 1 to 4 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkyl-carbonylamino, $C_{1-6}$ alkyl-carbonyl, carboxyl, $C_{1-6}$ alkoxy-carbonyl, carbamoyl, mono-$C_{1-6}$ alkylcarbamoyl, di-$C_{1-6}$ alkylcarbamoyl, sulfo, $C_{1-6}$ alkylsulfonyl, $C_{1-6}$ alkylsulfinyl, $C_{6-10}$ aryl and $C_{6-10}$ aryloxy.

6. The compound of claim 1 wherein P and Q are independently a $C_{2-6}$ alkylene or $C_{2-6}$ alkenylene group.

7. The compound of claim 1 wherein P and Q are independently a $C_{3-5}$ alkylene group.

8. The compound of claim 1 wherein $R^4$ is hydrogen.

9. The compound of claim 1 wherein j is 0.

10. The compound of claim 1 which is the compound of the formula:

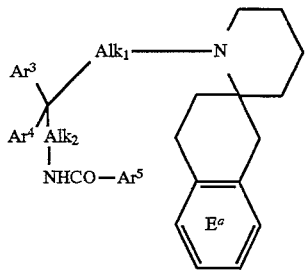

wherein $Ar^3$ and $Ar^4$ are independently an optionally halogenated phenyl group; $Alk_1$ and $Alk_2$ are independently a $C_{2-6}$ alkylene group; $Ar^5$ is a $C_{7-16}$ aralkyl group which may be substituted by halogen or optionally halogenated $C_{1-3}$ alkoxy; and ring $E^a$ is a benzene ring which may be substituted by 1 to 3 substituents selected from the group consisting of optionally halogenated $C_{1-3}$ alkoxy, $C_{1-3}$ alkyl-carbonyl and amino.

11. The compound of claim 1 which is (+)-3,4-Dihydro-6-methoxy-1'-{4,4-diphenyl-7-{[(4-methoxyphenyl)acetyl]amino}heptyl}spiro[naphthalene-2(1H),2'-piperidine], (−)-3,4-Dihydro-6-methoxy-1'-{4,4-diphenyl-7-{[(4-methoxyphenyl)acetyl]amino}heptyl}spiro[naphthalene-2(1H),2'-piperidine], (−)-3,4-Dihydro-6,7-dimethoxy-1'-{4,4-diphenyl-7-{[(4-methoxyphenyl)acetyl]amino}heptyl}spiro[naphthalene-2(1H),2'-piperidine]-1-one, (−)-3,4-Dihydro-6,7-dimethoxy-1'-{4,4-diphenyl-7-{[(4-fluorophenyl)acetyl]amino}heptyl}spiro[naphthalene-2(1H),2'-piperidine], (+)-3,4-Dihydro-6,7-dimethoxy-1'-{4,4-diphenyl-7-{[(4-fluorophenyl)acetyl]amino}heptyl}spiro[naphthalene-2(1H),2'-piperidine], (−)-3,4-Dihydro-6,7-dimethoxy-1'-{4,4-diphenyl-7-{[3-(4-fluorophenyl)propionyl]amino}heptyl}spiro[naphthalene-2(1H),2'-piperidine], (+)-3,4-Dihydro-6,7-dimethoxy-1'-{4,4-diphenyl-7-{[3-(4-fluorophenyl)propionyl]amino}heptyl}spiro[naphthalene-2(1H),2'-piperidine], (+)-3,4-Dihydro-6,7-dimethoxy-1'-{7-{[3-(4-chlorophenyl)propionyl]amino}-4,4-diphenylheptyl}spiro[naphthalene-2(1H),2'-piperidine], (−)-3,4-Dihydro-6,7-dimethoxy-1'-{7-{[3-(4-chlorophenyl)propionyl]amino}-4,4-diphenylheptyl}spiro[naphthalene-2(1H),2'-piperidine], (−)-3,4-Dihydro-6,7-dimethoxy-1'-{4,4-diphenyl-7-{[3-(4-methoxyphenyl)propionyl]amino}heptyl}spiro[naphthalene-2(1H),2'-piperidine], (+)-3,4-Dihydro-6,7-dimethoxy-1'-{4,4-diphenyl-7-{[3-(4-methoxyphenyl)propionyl]amino}heptyl}spiro[naphthalene-2(1H),2'-piperidine], 3,4-Dihydro-4'-{4,4-diphenyl-7-{[3-(4-methoxyphenyl)propionyl]amino}heptyl}spiro[naphthalene-2(1H),3'-morpholine], 3,4-Dihydro-7-methoxy-4'-{4,4-diphenyl-7-{[3-(4-methoxyphenyl)propionyl]amino}heptyl}spiro[naphthalene-2(1H),3'-morpholine], 3,4-Dihydro-6,7-dimethoxy-4'-{4,4-diphenyl-7-{[3-(4-methoxyphenyl)propionyl]amino}heptyl}spiro[naphthalene-2(1H),3'-morpholine], or a salt thereof.

12. A process for producing the compound of claim 1, which comprises reacting a compound of the formula:

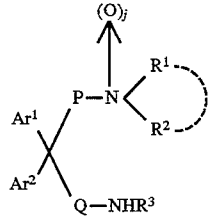

wherein all symbols are as defined in claim 1, or a salt thereof, with a compound of the formula:

R⁴—L wherein L represents a leaving group and $R^4$ is as defined in claim 1, or a salt thereof.

13. A gonadotropin-releasing hormone receptor antagonistic composition which comprises a compound of the formula:

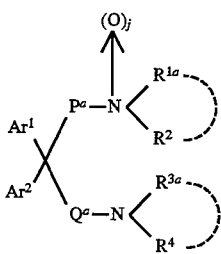

wherein

Ar¹ and Ar² independently represent an optionally substituted aromatic group;

$P^a$ and $Q^a$ independently represent a divalent aliphatic hydrocarbon group which may have either oxygen or sulfur within the carbon chain;

$R^{1a}$ and $R^{3a}$ independently represent an acyl group or an optionally substituted hydrocarbon group;

$R^2$ and $R^4$ independently represent hydrogen or an optionally substituted alkyl group;

$R^{1a}$ and $R^2$ or $R^{3a}$ and $R^4$, taken together with the adjacent nitrogen atom, may form an optionally substituted nitrogen-containing heterocyclic group; and j represents 0 or 1, or a salt thereof, and a pharmaceutically acceptable carrier.

14. A gonadotropin-releasing hormone receptor antagonistic composition which comprises the compound of claim 1 or a salt thereof, and a pharmaceutically acceptable carrier.

15. The composition of claim 13 which is a composition for treating a sex hormone-dependent disease.

16. The composition of claim 14 which is a composition for treating tumor, prostatic hypertrophy, endometriosis, precocious puberty or premenstrual syndrome.

17. A method for treating diseases related to gonadotropin-releasing hormone in mammals which comprises the steps of selecting a compound of the formula:

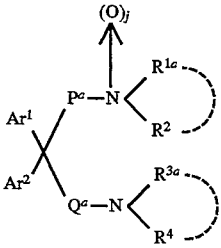

wherein Ar¹ and Ar² independently represent an optionally substituted aromatic group;

$P^a$ and $Q^a$ independently represent a divalent aliphatic hydrocarbon group which may have either oxygen or sulfur within the carbon chain;

$R^{1a}$ and $R^{3a}$ independently represent an acyl group or an optionally substituted hydrocarbon group;

$R^2$ and $R^4$ independently represent hydrogen or an optionally substituted alkyl group;

$R^{1a}$ and $R^2$ or $R^{3a}$ and $R^4$, taken together with the adjacent nitrogen atom, may form an optionally substituted nitrogen-containing heterocyclic group; and j represents 0 or 1, or a salt thereof, and administering to a subject a therapeutically effective amount of said compound.

18. A method of manufacturing a pharmaceutical composition for treating diseases related to gonadotropin-releasing hormone, comprising the steps of selecting a compound of the formula:

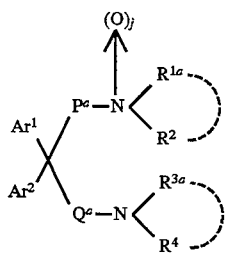

wherein

Ar¹ and Ar² independently represent an optionally substituted aromatic group;

$P^a$ and $Q^a$ independently represent a divalent aliphatic hydrocarbon group which may have either oxygen or sulfur within the carbon chain;

$R^{1a}$ and $R^{3a}$ independently represent an acyl group or an optionally substituted hydrocarbon group;

$R^2$ and $R^4$ independently represent hydrogen or an optionally substituted alkyl group;

$R^{1a}$ and $R^2$ or $R^{3a}$ and $R^4$, taken together with the adjacent nitrogen atom, may form an optionally substituted nitrogen-containing heterocyclic group; and j represents 0 or 1, or a salt thereof;

and admixing said compound with a pharmaceutically acceptable carrier.

* * * * *

UNITED STATES PATENT AND TRADEMARK OFFICE
CERTIFICATE OF CORRECTION

PATENT NO. : 5,633,248

DATED : May 27, 1997

INVENTOR(S): KANEYOSHI KATO, ET AL.  Page 1 of 5

It is certified that error appears in the above-identified patent and that said Letters Patent is hereby corrected as shown below:

COLUMN 1

Line 8, "gonadotropin releasing" should read
      --gonadotropin-releasing--.
    Line 34, "for it" should read --for instance, it--.
    Line 49, "research" should read --research on--.

COLUMN 2

Line 20, " 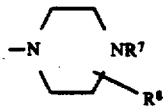 " should read -- 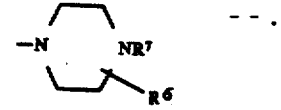 --.

COLUMN 9

Line 44, Insert: "iii)".

COLUMN 16

Line 20, Insert: "(i)".

COLUMN 17

Line 5, Insert: "(iii)".
    Line 17, "$C_{1-6}$alkyl" should read --$C_{1-6}$ alkyl--.

UNITED STATES PATENT AND TRADEMARK OFFICE
CERTIFICATE OF CORRECTION

PATENT NO. : 5,633,248

DATED : May 27, 1997

INVENTOR(S) : KANEYOSHI KATO, ET AL.

It is certified that error appears in the above-identified patent and that said Letters Patent is hereby corrected as shown below:

COLUMN 19

Line 37, "includes," should read --include,--.

COLUMN 22

Line 23, "$C_{1-6}$alkylcarbamoyl," should read
     --$C_{1-6}$ alkylcarbamoyl,--.

COLUMN 23

Line 42, "$Ar^{5'}$" should read --$Ar^5$--.

COLUMN 27

Line 20, "Process 2" should be deleted.
   Line 25, Insert: "Process 2".
   Line 60, Insert: "(wherein $R^5$ represents an N-protecting
     group of the acyl type; L represents a leaving group;
     the other symbols have the meaning defined
     hereinbefore)".

COLUMN 30

Line 53," hydrogencarbonates" should read
     --hydrogen carbonates--.

COLUMN 36

Line 40, "3" should read --3-3--.

UNITED STATES PATENT AND TRADEMARK OFFICE
CERTIFICATE OF CORRECTION

PATENT NO. : 5,633,248

DATED : May 27, 1997

INVENTOR(S) : KANEYOSHI KATO, ET AL.

It is certified that error appears in the above-identified patent and that said Letters Patent is hereby corrected as shown below:

COLUMN 37

Line 14, "(1-g)" should read --(1 g)--.

COLUMN 40

Line 48, "to" should be deleted.

COLUMN 55

Line 16, "which" should read --white--.

COLUMN 58

Line 6, "extracted" should read --extract--.

COLUMN 99

Table 28, under column "$^1$H-NMR ($\delta_{ppm}$, $CDCl_3$)", in row "II-62", "q)," should read --(2H, q),--.

COLUMN 103

Line 8, "-40°C." should read --at -40°C.--.
Line 23, "Hydrochloride" should read --hydrochloride--.

COLUMN 104

Line 7, "Hydrochloride" should read --hydrochloride--.
Line 45, "Hydrochloride" should read --hydrochloride--.

UNITED STATES PATENT AND TRADEMARK OFFICE
CERTIFICATE OF CORRECTION

PATENT NO. : 5,633,248

DATED : May 27, 1997

INVENTOR(S) : KANEYOSHI KATO, ET AL.

It is certified that error appears in the above-identified patent and that said Letters Patent is hereby corrected as shown below:

COLUMN 105

Line 7, "Hydrochloride" should read --hydrochloride--.
   Line 41, "Hydrochloride" should read --hydrochloride--.

COLUMN 112

Line 37, "3,4Dihydro-6," should read --3,4-Dihydro-6,--.

COLUMN 130

Line 44, "$C_1.3$" should read --$C_{1-3}$--.
   Line 50, "$C_{1-6}$alkoxy-carbonyl," should read
       --$C_{1-6}$ alkoxy-carbonyl,--.

COLUMN 131

Line 42, "$C_1.6$" should read --$C_{1-6}$--.
   Line 59, "$C_1.6$" should read --$C_{1-6}$--.

COLUMN 132

Line 17, "$C_1.6$" should read --$C_{1-6}$--.

UNITED STATES PATENT AND TRADEMARK OFFICE
CERTIFICATE OF CORRECTION

PATENT NO. : 5,633,248

DATED : May 27, 1997

INVENTOR(S) : KANEYOSHI KATO, ET AL.

It is certified that error appears in the above-identified patent and that said Letters Patent is hereby corrected as shown below:

<u>COLUMN 133</u>

Line 29, "$C_1.6$" should read --$C_{1-6}$--.
Line 53, "$C_1.3$" should read --$C_{1-3}$--.

Signed and Sealed this

Tenth Day of February, 1998

Attest:

BRUCE LEHMAN

*Attesting Officer*   *Commissioner of Patents and Trademarks*